United States Patent
Suzuki

(10) Patent No.: US 10,933,119 B2
(45) Date of Patent: Mar. 2, 2021

(54) AORTOPATHY

(71) Applicant: University of Leicester, Leicestershire (GB)

(72) Inventor: Toru Suzuki, Leicester (GB)

(73) Assignee: University of Leicester, Leicestershire (GB)

( * ) Notice: Subject to any disclaimer, the term of this patent is extended or adjusted under 35 U.S.C. 154(b) by 193 days.

(21) Appl. No.: 15/553,204

(22) PCT Filed: Feb. 19, 2016

(86) PCT No.: PCT/GB2016/050413
§ 371 (c)(1),
(2) Date: Aug. 24, 2017

(87) PCT Pub. No.: WO2016/135456
PCT Pub. Date: Sep. 1, 2016

(65) Prior Publication Data
US 2018/0028613 A1 Feb. 1, 2018

(30) Foreign Application Priority Data

Feb. 25, 2015 (GB) .................................. 1503139.6
Jul. 30, 2015 (GB) .................................. 1513390.3

(51) Int. Cl.
| | | |
|---|---|---|
| A61K 38/19 | (2006.01) | |
| A61K 39/395 | (2006.01) | |
| A61K 38/17 | (2006.01) | |
| A61K 45/06 | (2006.01) | |
| A61K 39/00 | (2006.01) | |

(52) U.S. Cl.
CPC ........ *A61K 38/193* (2013.01); *A61K 38/1741* (2013.01); *A61K 39/39541* (2013.01); *A61K 45/06* (2013.01); *A61K 2039/505* (2013.01)

(58) Field of Classification Search
None
See application file for complete search history.

(56) References Cited

U.S. PATENT DOCUMENTS 5,391,706 A * 2/1995 Trotta ................... C07K 14/535
435/69.5
2011/0045000 A1* 2/2011 Steidl ................... C07K 16/243
424/158.1

OTHER PUBLICATIONS

Seelig et al. (1994),JBC vol. 269, No. 8, pp. 5548-553 (Year: 1994).*
Eylenstein Molecular basis of in vitro affinity maturation and functional evolution of a neutralizing anti-human GM-CSF antibody, mAbs, 8:1, 176-186,DOI: 10.1080/19420862.2015.1099774 (Year: 2016).*
Weissen-Plenz et al. (J. of Cardiothoracic Surgery, 2010, vol. 5:66, p. 1-5) (Year: 2010).*
International Search Report and Written Opinion dated Sep. 22, 2016 issued in PCT/GB2016/050413.
Ping, YE et al., "GM-CSF contributes to 1-5,11, aortic aneurysms resulting from SMAD3 12 deficiency (includes supplemental material)", Journal of Clinical Investigation (May 1, 2013), vol. 123, No. 5, pp. 2317-2360.
Wagner, K. et al., "Inhibition of granulocyte-macrophage colony-stimulating factor receptor function by a splice variant of the common beta-receptor subunit", Blood (Nov. 1, 2001), vol. 98, No. 9, pp. 2689-2696.
Notarangelo, Luigi D. et al., "Out of breath: GM-CSFR[alpha] mutations disrupt surfactant homeostasis: Figure 1.", The Journal of Experimental Medicine (Nov. 24, 2008), vol. 163, No. 12, pp. 2674-2697.
Niu, Linghao et al., "High-affinity binding to the GM-CSF receptor requires intact N-glycosylation sites in the extracellular domain of the beta subunit", Blood (Jun. 1, 2000), vol. 95, No. 11, pp. 3357-3362.
Shaposhnik, Z. et al., "Granulocyte Macrophage Colony-Stimulating Factor Regulates Dendritic Cell Content of Atherosclerotic Lesions", Arteriosclerosis, Thrombosis, and Vascular Biology (Mar. 1, 2007) vol. 27, No. 3, pp. 621-627.
Subramanian, M. et al., "Identification of a Non-Growth Factor Role for GM-CSF in Advanced Atherosclerosis: Promotion of Macrophage Apoptosis and Plaque Necrosis Through IL-23 Signaling", Circulation Research (Oct. 27, 2014), vol. 116, No. 2, pp. e13-e24.
Haghighat, A. et al., "Granulocyte Colony-Stimulating Factor and Granulocyte Macrophage Colony-Stimulating Factor Exacerbate Atherosclerosis in Apolipoprotein E-Deficient Mice", Circulation (Apr. 17, 2007), vol. 115, No. 15, pp. 2049-2054.
Database Biosis [Online] Biosciences Information Service, Philadelphia, PA, US; Nov. 2012, Son Bo K et al: "KLF6 Modulates Aortic Aneurysm Formation by Balancing Between Inflarrmatory and TGF beta Signaling Pathways", Database accession No. PREV281400457153, abstract & Circulation, vol. 126, No. 21, Suppl. S, 17973, Nov. 2012 (Nov. 2012), American-Heart-Association Resuscitation Science Symposium; Los Angeles, CA, USA; Nov. 3-4, 2012.
Hiratzka, Loren, F., et al., ACC Guidelines, Journal of the American College of Cardiology, 55.14 (2010): e27-e129.

* cited by examiner

*Primary Examiner* — Gary B Nickol
*Assistant Examiner* — Jegatheesan Seharaseyon
(74) *Attorney, Agent, or Firm* — Scully Scott Murphy & Presser

(57) ABSTRACT

The invention relates to aortopathy, and in particular, to compositions and methods for the diagnosis and treatment of aortopathy.

Figures 1A, 1B:
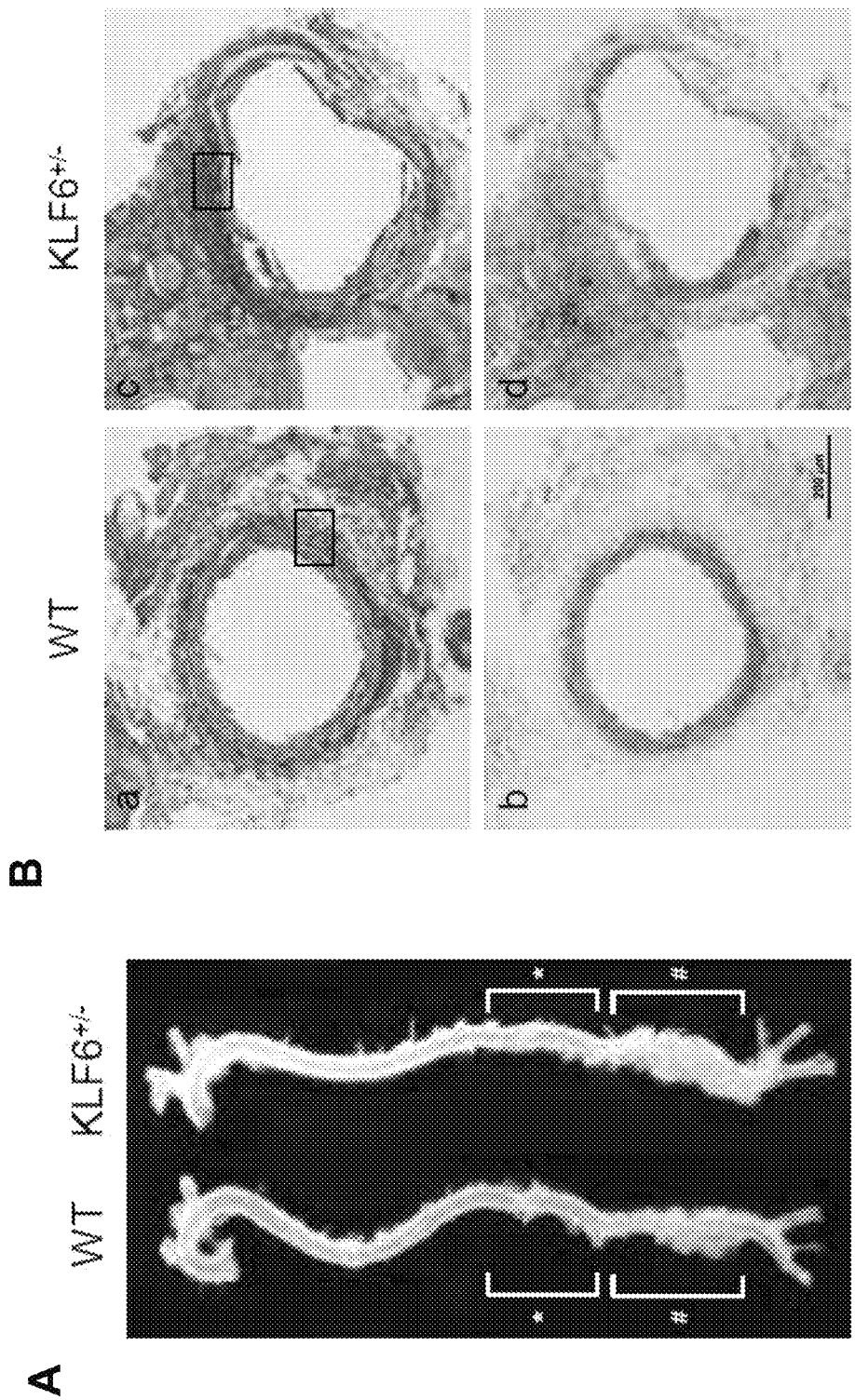
Figures 1C, 1D, 1E:
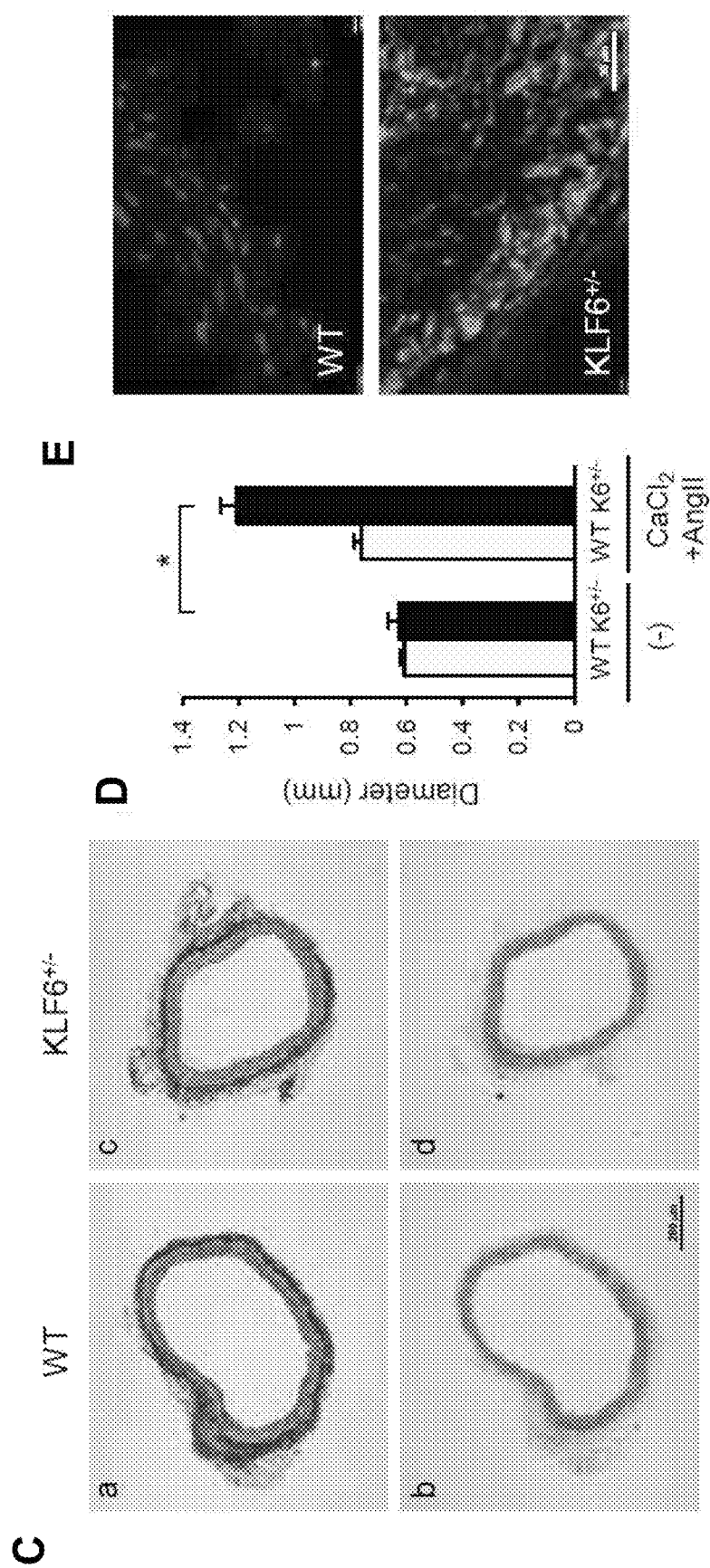

6 Claims, 34 Drawing Sheets
Specification includes a Sequence Listing.

A

*KLF6^{fl/fl};LysM Cre*

B

C

AORTOPATHY

The invention relates to aortopathy, and in particular, to compositions and methods for the diagnosis and treatment of aortopathy.

INCORPORATION BY REFERENCE OF SEQUENCE LISTING

The Sequence Listing in an ASCII text file, named as 35308_Sequence_Listing.txt of 11 KB, created on Aug. 22, 2017, and submitted to the United States Patent and Trademark Office via EFS-Web, is incorporated herein by reference.

Aortopathy relates to diseases of the aorta. Aortic dissection and intramural hematoma comprise a potentially life-threatening aortopathy involving separation of the aortic wall (1-6). The two conditions are distinguished by a tear in the aortic intima as present in the former classical form of aortic dissection which results in blood flow into the aortic wall and is absent in the latter form of intramural hematoma with bleeding confined within the aortic wall. This aortopathy is presently understood to be a continuum with the latter a variant and precursory condition of the former (7-9). Advances in the understanding of genetic underpinnings (e.g. ACTA2) (10,11), clinical/epidemiological aspects (e.g. IRAD) (4,5) as well as biochemical approaches (e.g. smooth muscle biomarkers) (5,6) have been made in the last decade, but underlying mechanisms have remained obscure owing much to lack of a reliable animal model.

Recent advances in understanding mechanisms of aortic disease have stemmed from hallmark studies in the genetically fragile Marfan aorta which have shown that TGFβ and its downstream intracellular kinase signaling pathways play a central role in the pathogenesis (12-14). In contrast, an inflammatory pathway is thought to be a major component of aortic conditions in the atherosclerotic/degenerative aorta seen in the typical elderly patient (15,16). Commonalities and differences in mechanisms as well as relative contributions of underlying processes in these different aortic conditions have only begun to be unraveled.

There is therefore a need to provide improved compositions and methods for diagnosis and treatment of aortopathy.

In the present study, the inventors sought to address the underlying mechanisms of aortic dissection/intramural hematoma, and to understand the triggering mechanism of the condition. Krüppel-like factor 6 (KLF6) is a transcription factor that has been shown to be robustly expressed in macrophages (17), and to regulate inflammatory fibrotic diseases of multiple organs including the liver (18), kidney (19) and heart (D.S., unpublished data). The inventors hypothesized that this factor might regulate pathogenic mechanisms underlying aortic disease, and observed that mice deficient for KLF6 in macrophages when subjected to aortic inflammation manifest aortic dissection/intramural hematoma.

Surprisingly, the inventors found that the inflammatory cytokine, granulocyte macrophage colony-stimulating factor (GM-CSF), plays a central role in the onset of this condition. Furthermore, administration of a neutralizing antibody against GM-CSF surprisingly prevented the condition in these mice. Conversely, administration of the cytokine in combination with aortic inflammation to wild-type mice was sufficient to induce the condition suggesting general effects. Clinically, patients with aortic dissection showed elevated circulating levels of the cytokine, which was also expressed in the dissected aorta. GM-CSF is therefore a key regulatory molecule causative of aortic dissection/intramural hematoma, and antagonism of this cytokine will result in therapeutic exploitation (e.g. aortic stabilization using GM-CSF antagonists). GM-CSF also acts as a diagnostic biomarker.

Therefore, according to a first aspect of the invention, there is provided a granulocyte macrophage colony-stimulating factor (GM-CSF) negative modulator, for use in treating, preventing or ameliorating aortopathy.

In a second aspect, there is provided a method of treating, preventing or ameliorating aortopathy in a subject, the method comprising administering, to a subject in need of such treatment, a therapeutically effective amount of a granulocyte macrophage colony-stimulating factor (GM-CSF) negative modulator.

Preferably, the GM-CSF negative modulator is for treating, preventing or ameliorating an aortopathic condition selected from a group consisting of: aortic dissection; aortic intramural hematoma progression or recurrence; aortic aneurysm expansion, inflammation and/or rupture; and aortitis (i.e. aortic inflammation). In one embodiment, the GM-CSF negative modulator may be used in maintenance treatment to prevent recurrent aortic dissection in subjects who have undergone primary surgical revision for acute aortic dissection. In another embodiment, the GM-CSF negative modulator may be used in maintenance treatment to prevent aortic dissection progression in subjects with chronic aortic dissection, i.e. abdominal dissection, where surgery is less favourable due to a higher risk of paraplegia.

Granulocyte macrophage colony-stimulating factor (GM-CSF) or colony stimulating factor 2 (CSF2) is a monomeric glycoprotein secreted by macrophages, T cells, mast cells, NK cells, endothelial cells and fibroblasts and functions as a cytokine. It is a white blood cell growth factor, and GM-CSF signals via the signal transducer and activator of transcription, STAT5 and STAT3. One embodiment of the DNA sequence of human GM-CSF (GenBank No: NC_000005.10) is provided herein as SEQ ID No:1, as follows:—

[SEQ ID No: 1]
ACACAGAGAGAAAGGCTAAAGTTCTCTGGAGGATGTGGCTGCAGAGCCTG

CTGCTCTTGGGCACTGTGGCCTGCAGCATCTCTGCACCCGCCCGCTCGCC

CAGCCCCAGCACGCAGCCCTGGGAGCATGTGAATGCCATCCAGGAGGCCC

GGCGTCTCCTGAACCTGAGTAGAGACACTGCTGCTGAGATGGTAAGTGAG

AGAATGTGGGCCTGTGCCTAGGCCACCCAGCTGGCCCCTGACTGGCCACG

CCTGTCAGCTTGATAACATGACATTTTCCTTTTCTACAGAATGAAACAGT

AGAAGTCATCTCAGAAATGTTTGACCTCCAGGTAAGATGCTTCTCTCTGA

CATAGCTTTCCAGAAGCCCCTGCCCTGGGGTGGAGGTGGGGACTCCATTT

TAGATGGCACCACACAGGGTTGTCCACTTTCTCTCCAGTCAGCTGGCTGC

AGGAGGAGGGGTAGCAACTGGGTGCTCAAGAGGCTGCTGGCCGTGCCCC

TATGGCAGTCACATGAGCTCCTTTATCAGCTGAGCGGCCATGGGCAGACC

TAGCATTCAATGGCCAGGAGTCACCAGGGGACAGGTGGTAAAGTGGGGGT

CACTTCATGAGACAGGAGCTGTGGGTTTGGGGCGCTCACTGTGCCCCGAG

ACCAAGTCCTGTTGAGACAGTGCTGACTACAGAGAGGCACAGAGGGGTTT

CAGGAACAACCCTTGCCCACCCAGCAGGTCCAGGTGAGGCCCCACCCCCC

TCTCCCTGAATGATGGGGTGAGAGTCACCTCCTTCCCTAAGGCTGGGCTC

-continued

```
CTCTCCAGGTGCCGCTGAGGGTGGCCTGGGCGGGGCAGTGAGAAGGGCAG

GTTCGTGCCTGCCATGGACAGGGCAGGGTCTATGACTGGACCCAGCCTGT

GCCCCTCCCAAGCCCTACTCCTGGGGGCTGGGGGCAGCAGCAAAAAGGAG

TGGTGGAGAGTTCTTGTACCACTGTGGGCACTTGGCCACTGCTCACCGAC

GAACGACATTTTCCACAGGAGCCGACCTGCCTACAGACCCGCCTGGAGCT

GTACAAGCAGGGCCTGCGGGGCAGCCTCACCAAGCTCAAGGGCCCCTTGA

CCATGATGGCCAGCCACTACAAGCAGCACTGCCCTCCAACCCCGGTGAGT

GCCTACGGCAGGGCCTCCAGCAGGAATGTCTTAATCTAGGGGGTGGGGTC

GACATGGGAGAGATCTATGGCTGTGGCTGTTCAGGACCCCAGGGGTTT

CTGTGCCAACAGTTATGTAATGATTAGCCCTCCAGAGAGGAGGCAGACAG

CCCATTTCATCCCAAGGAGTCAGAGCCACAGAGCGCTGAAGCCCACAGTG

CTCCCCAGCAGGAGCTGCTCCTATCCTGGTCATTATTGTCATTATGGTTA

ATGAGGTCAGAGGTGAGGGCAAACCCAAGGAAACTTGGGGCCTGCCCAAG

GCCCAGAGGAAGTGCCCAGGCCCAAGTGCCACCTTCTGGCAGGACTTTCC

TCTGGCCCCACATGGGGTGCTTGAATTGCAGAGGATCAAGGAAGGGAGGC

TACTTGGAATGGACAAGGACCTCAGGCACTCCTTCCTGCGGGAAGGGAGC

AAAGTTTGTGGCCTTGACTCCACTCCTTCTGGGTGCCCAGAGACGACCTC

AGCCCAGCTGCCCTGCTCTGCCCTGGGACCAAAAAGGCAGGCGTTTGACT

GCCCAGAAGGCCAACCTCAGGCTGGCACTTAAGTCAGGCCCTTGACTCTG

GCTGCCACTGGCAGAGCTATGCACTCCTTGGGGAACACGTGGGTGGCAGC

AGCGTCACCTGACCCAGGTCAGTGGGTGTGTCCTGGAGTGGGCCTCCTGG

CCTCTGAGTTCTAAGAGGCAGTAGAGAAACATGCTGGTGCTTCCTTCCCC

CACGTTACCCACTTGCCTGGACTCAAGTGTTTTTTATTTTTCTTTTTTA

AAGGAAACTTCCTGTGCAACCCAGATTATCACCTTTGAAAGTTTCAAAGA

GAACCTGAAGGACTTTCTGCTTGTCATCCCCTTTGACTGCTGGGAGCCAG

TCCAGGAGTGAGACCGGCCAGATGAGGCTGGCCAAGCCGGGAGCTGCTC

TCTCATGAAACAAGAGCTAGAAACTCAGGATGGTCATCTTGGAGGGACCA

AGGGGTGGGCCACAGCCATGGTGGGAGTGGCCTGGACCTGCCCTGGGCCA

CACTGACCCTGATACAGGCATGGCAGAAGAATGGGAATATTTTATACTGA

CAGAAATCAGTAATATTTATATATTTATATTTTTAAAATATTTATTTATT

TATTTATTTAAGTTCATATTCCATATTTATTCAAGATGTTTTACCGTAAT

AATTATTATTAAAAATATGCTTCTACTTG
```

One embodiment of the protein sequence (GenBank No: AAA52578.1; 144 amino acids) of human GM-CSF, is provided herein as SEQ ID No:2, as follows:—

[SEQ ID No: 2]
MWLQSLLLLGTVACSISAPARSPSPSTQPWEHVNAIQEARRLLNLSRDTA

AEMNETVEVISEMFDLQEPTCLQTRLELYKQGLRGSLTKLKGPLTMMASH

YKQHCPPTPETSCATQIITFESFKENLKDFLLVIPFDCWEPVQE

Figure 3A:
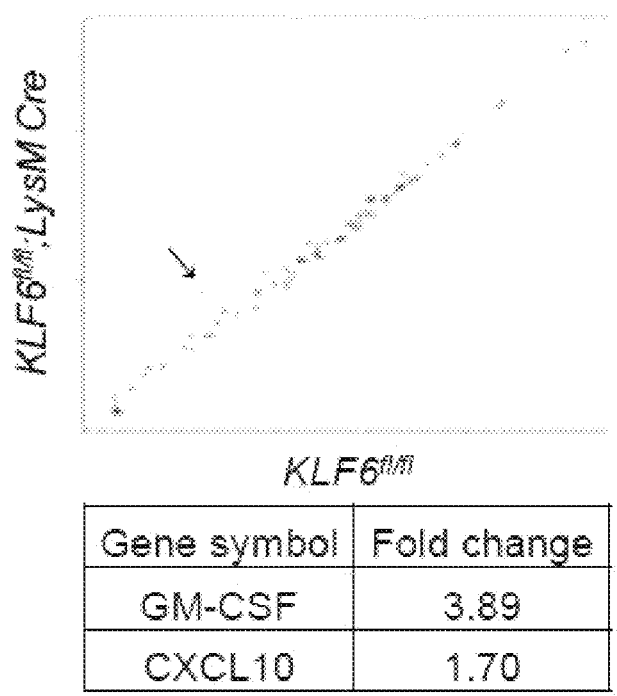
Figure 3B:
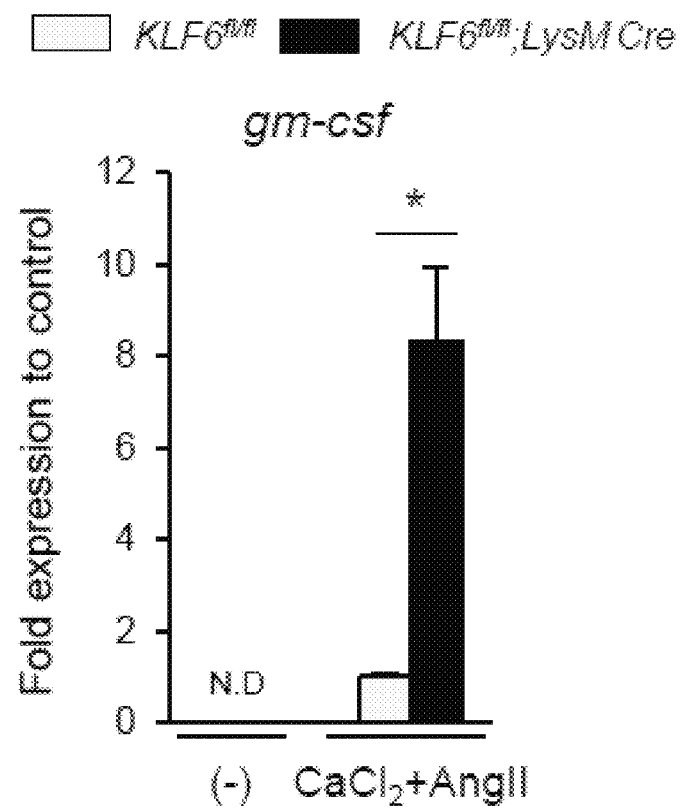

As described in Example 3, and as shown in FIGS. 3a, 3b, and boa, GM-CSF levels showed the greatest increase in macrophages derived from bone marrow of KLF6fl/fl;LysM Cre mice in response to AngII stimulation, as compared to control macrophages. Macrophages obtained from aorta of KLF6fl/fl;LysM Cre mice showed markedly increased expression of GM-CSF under experimental conditions of CaCl2 application and AngII infusion, and in macrophages derived from bone marrow of these mice. In addition, as described in Example 4, and as shown in FIG. 4, the actions of GM-CSF were blocked using a neutralizing antibody which abrogated aortic dissection/intramural hematoma (FIG. 4A, B ), as well as expression of GM-CSF receptor α, MMP9, F4/80 and IL-6 in addition to serum levels of IL-6. GM-CSF is therefore required for the aortic phenotype in KLF6fl/fl;LysM Cre mice. As shown in Table 4, the number of circulating granulocytes and lymphocytes was not affected when GM-CSF was depleted by neutralizing antibody. Hence, based on these results, manipulation of GM-CSF did not affect the number of circulating leukocytes in the present model, at least during the observation period (14 days).

Thus, in one embodiment, the GM-CSF negative modulator may be configured to:—

(i) alter the conformational state of the GM-CSF receptor or signal transduction molecule through which GM-CSF signalling is achieved, for example by destabilizing the active conformation of that macrophage receptor and/or maintaining the receptor in its inactive conformation to thereby prevent it from binding its natural ligand, i.e. GM-CSF;

(ii) bind to the GM-CSF receptor through which GM-CSF signalling is achieved, and prevent, decrease or attenuate transmission at that receptor;

(iii) down-regulate or de-activate the downstream signalling pathways activated by the negative modulator binding to the GM-CSF receptor, or to GM-CSF itself;

(iv) decrease, prevent or attenuate transcription, translation or expression of GM-CSF;

(v) inhibit synthesis or release, from intracellular stores, of GM-CSF; and/or (vi) increase the rate of degradation of GM-CSF.

It will be appreciated that each of mechanisms (i) to (vi) results in a reduction in the transmission at the receptor/signal transduction molecule through which GM-CSF is directed, and the activity thereof, to thereby negatively modulate GM-CSF signalling. The receptor through which of GM-CSF signalling is also known as Cluster of Differentiation 116, i.e. CD116. It is a heterodimer composed of an alpha and a beta chain. The alpha subunit contains a binding site for GM-CSF, and the beta chain is involved in signal transduction. Association of the two subunits results in receptor activation.

In a preferred embodiment, the negative modulator comprises an anti-GM-CSF antibody or antigen-binding fragment thereof. It will be appreciated that anti-GM-CSF antibodies are well-known to the skilled person, and commercially available, for example from R&D Systems or Santa Cruz Biotechnology, Inc. In one embodiment, the anti-GM-CSF antibody (as used in the Examples) is a mouse GM-CSF antibody (monoclonal rat IgG2A Clone #MP122 E9; catalogue number: MAB415 available from R&D Systems). In another embodiment, the anti-GM-CSF antibody is catalogue number: sc-377039 (from Santa Cruz Biotechnology, Inc.). Although anti-GM-CSF antibodies are known, and are used for treatment of rheumatoid arthritis, it was totally unexpected that such anti-GM-CSF antibodies could also have utility in the treatment of aortopathy, and related diseases described herein.

Preferably, the anti-GM-CSF antibody or antigen-binding fragment thereof specifically binds to SEQ ID No:2, or a variant or fragment thereof.

The epitope recognized by GM-CSF antibody from R&D Systems is unknown. However, the GM-CSF antibody from Santa Cruz (catalogue number: se-377039) binds to an epitope mapping between amino acids 115-144 (TQIIT-FESFKENLKDFLLVIPFDCWEPVQE—SEQ ID No:3) at the C-terminus of GM-CSF of human origin. Hence, preferably the anti-GM-CSF antibody or antigen-binding fragment thereof specifically binds to SEQ ID No:3, or a variant or fragment thereof.

The antibody or antigen-binding fragment thereof may be monovalent, divalent or polyvalent. Preferably, the antibody or antigen-binding fragment thereof is isolated or purified.

In one preferred embodiment, the antibody or antigen-binding fragment thereof comprises a polyclonal antibody, or an antigen-binding fragment thereof. The antibody or antigen-binding fragment thereof may be generated in a rabbit, mouse or rat.

In another preferred embodiment, the antibody or antigen-binding fragment thereof comprises a monoclonal antibody or an antigen-binding fragment thereof. Preferably, the antibody of the invention is a human or humanised antibody.

As used herein, the term "human antibody" can mean an antibody, such as a monoclonal antibody, which comprises substantially the same heavy and light chain CDR amino acid sequences as found in a particular human antibody exhibiting immunospecificity for SEQ ID No:2, or a variant or fragment thereof. An amino acid sequence, which is substantially the same as a heavy or light chain CDR, exhibits a considerable amount of sequence identity when compared to a reference sequence. Such identity is definitively known or recognizable as representing the amino acid sequence of the particular human antibody. Substantially the same heavy and light chain CDR amino acid sequence can have, for example, minor modifications or conservative substitutions of amino acids. Such a human antibody maintains its function of selectively binding to SEQ ID No:2 or a variant or fragment thereof.

The term "human monoclonal antibody" can include a monoclonal antibody with substantially or entirely human CDR amino acid sequences produced, for example by recombinant methods such as production by a phage library, by lymphocytes or by hybridoma cells.

The term "humanised antibody" can mean an antibody from a non-human species (e.g. mouse or rabbit) whose protein sequences have been modified to increase their similarity to antibodies produced naturally in humans.

The antibody may be a recombinant antibody, i.e. a human antibody produced using recombinant DNA technology.

The term "antigen-binding region" can mean a region of the antibody having specific binding affinity for its target antigen, for example, the peptide of SEQ ID No:2, or a variant or fragment thereof. Preferably, the fragment is an epitope, preferably SEQ ID No:3 or a variant or fragment thereof. The binding region may be a hypervariable CDR or a functional portion thereof. The term "functional portion" of a CDR can mean a sequence within the CDR which shows specific affinity for the target antigen. The functional portion of a CDR may comprise a ligand which specifically binds to SEQ ID No:2 or a fragment thereof.

It will be appreciated that negative modulators according to the invention (collectively referred to herein as "agents") may be used in a monotherapy (e.g. the use of an antibody or antigen binding fragment thereof alone), for treating, ameliorating or preventing aortopathy. Alternatively, agents according to the invention may be used as an adjunct to, or in combination with, known therapies for treating, ameliorating, or preventing aortopathy, such as anti-hypertensives (beta blockers) and analgesia.

The agents according to the invention may be combined in compositions having a number of different forms depending, in particular, on the manner in which the composition is to be used. Thus, for example, the composition may be in the form of a powder, tablet, capsule, liquid, ointment, cream, gel, hydrogel, aerosol, spray, micellar solution, transdermal patch, liposome suspension or any other suitable form that may be administered to a person or animal in need of treatment. It will be appreciated that the vehicle of medicaments according to the invention should be one which is well-tolerated by the subject to whom it is given, and preferably enables delivery of the agents to the heart.

Medicaments comprising agents of the invention may be used in a number of ways. For instance, oral administration may be required, in which case the agents may be contained within a composition that may, for example, be ingested orally in the form of a tablet, capsule or liquid. Compositions comprising agents and medicaments of the invention may be administered by inhalation (e.g. intranasally). Compositions may also be formulated for topical use. For instance, creams or ointments may be applied to the skin, for example adjacent to the heart.

Agents and medicaments according to the invention may also be incorporated within a slow- or delayed-release device. Such devices may, for example, be inserted on or under the skin, and the medicament may be released over weeks or even months. The device may be located at least adjacent the treatment site, i.e. the heart. Such devices may be particularly advantageous when long-term treatment with agents used according to the invention is required and which would normally require frequent administration (e.g. at least daily injection).

In a preferred embodiment, agents and medicaments according to the invention may be administered to a subject by injection into the blood stream or directly into a site requiring treatment. For example, the medicament may be injected at least adjacent the heart. Injections may be intravenous (bolus or infusion) or subcutaneous (bolus or infusion), or intradermal (bolus or infusion).

It will be appreciated that the amount of the agent (e.g. anti-GM-CSF antibody) that is required is determined by its biological activity and bioavailability, which in turn depends on the mode of administration, the physiochemical properties of the agent, and whether it is being used as a monotherapy or in a combined therapy. The frequency of administration will also be influenced by the half-life of the agent within the subject being treated. Optimal dosages to be administered may be determined by those skilled in the art, and will vary with the particular agent in use, the strength of the pharmaceutical composition, the mode of administration, and the advancement of the aortopathy. Additional factors depending on the particular subject being treated will result in a need to adjust dosages, including subject age, weight, gender, diet, and time of administration.

Generally, a daily dose of between 0.001 µg/kg of body weight and 10 mg/kg of body weight of agent according to the invention may be used for treating, ameliorating, or preventing aortopathy, depending upon which agent is used. More preferably, the daily dose of agent is between 0.01 µg/kg of body weight and 1 mg/kg of body weight, more preferably between 0.1 µg/kg and 100 µg/kg body weight, and most preferably between approximately 0.1 µg/kg and 10 µg/kg body weight.

The agent may be administered before, during or after onset of aortopathy. Daily doses may be given as a single administration (e.g. a single daily injection). Alternatively, the agent may require administration twice or more times during a day. As an example, agents may be administered as two (or more depending upon the severity of the aortopathy being treated) daily doses of between 0.07 µg and 700 mg (i.e. assuming a body weight of 70 kg). A patient receiving treatment may take a first dose upon waking and then a second dose in the evening (if on a two dose regime) or at 3- or 4-hourly intervals thereafter. Alternatively, a slow release device may be used to provide optimal doses of agents according to the invention to a patient without the need to administer repeated doses.

The dosage used for mice was 300 micrograms/mouse or 12 mg/kg every other day for 2 weeks by intra-peritoneal injection. Based on successful studies done in humans with intravenous MOR103 (1.0 or 1.5 mg/kg) once a week for 4 weeks and with subcutaneous mavrilimumab (100 mg) every other week for 12 weeks, intravenous or subcutaneous administration of 75 mg-100 mg once a week or every other week is preferred.

Known procedures, such as those conventionally employed by the pharmaceutical industry (e.g. in vivo experimentation, clinical trials, etc.), may be used to form specific formulations of the agents according to the invention and precise therapeutic regimes (such as daily doses of the agents and the frequency of administration).

Thus, in a third aspect of the invention, there is provided an aortopathy treatment pharmaceutical composition comprising a granulocyte macrophage colony-stimulating factor (GM-CSF) negative modulator; and optionally a pharmaceutically acceptable vehicle.

The invention also provides in a fourth aspect, a process for making the pharmaceutical composition according to the third aspect, the process comprising combining a therapeutically effective amount of a GM-CSF negative modulator with a pharmaceutically acceptable vehicle.

The negative modulator is preferably an antibody or antigen-binding fragment thereof, preferably an anti-GM-CSF antibody.

A "subject" may be a vertebrate, mammal, or domestic animal. Hence, medicaments according to the invention may be used to treat any mammal, for example livestock (e.g. a horse), pets, or may be used in other veterinary applications. Most preferably, the subject is a human being.

A "therapeutically effective amount" of the negative modulator is any amount which, when administered to a subject, is the amount of agent that is needed to treat the aortopathy disease, or produce the desired effect.

For example, the therapeutically effective amount of negative modulator used may be from about 0.001 ng to about 1 mg, and preferably from about 0.01 ng to about 100 ng. It is preferred that the amount of negative modulator is an amount from about 0.1 ng to about 10 ng, and most preferably from about 0.5 ng to about 5 ng.

A "pharmaceutically acceptable vehicle" as referred to herein, is any known compound or combination of known compounds that are known to those skilled in the art to be useful in formulating pharmaceutical compositions.

In one embodiment, the pharmaceutically acceptable vehicle may be a solid, and the composition may be in the form of a powder or tablet. A solid pharmaceutically acceptable vehicle may include one or more substances which may also act as flavouring agents, lubricants, solubilisers, suspending agents, dyes, fillers, glidants, compression aids, inert binders, sweeteners, preservatives, dyes, coatings, or tablet-disintegrating agents. The vehicle may also be an encapsulating material. In powders, the vehicle is a finely divided solid that is in admixture with the finely divided active agents according to the invention. In tablets, the active agent may be mixed with a vehicle having the necessary compression properties in suitable proportions and compacted in the shape and size desired. The powders and tablets preferably contain up to 99% of the active agents. Suitable solid vehicles include, for example calcium phosphate, magnesium stearate, talc, sugars, lactose, dextrin, starch, gelatin, cellulose, polyvinylpyrrolidine, low melting waxes and ion exchange resins. In another embodiment, the pharmaceutical vehicle may be a gel and the composition may be in the form of a cream or the like.

However, the pharmaceutical vehicle may be a liquid, and the pharmaceutical composition is in the form of a solution. Liquid vehicles are used in preparing solutions, suspensions, emulsions, syrups, elixirs and pressurized compositions. The active agent according to the invention may be dissolved or suspended in a pharmaceutically acceptable liquid vehicle such as water, an organic solvent, a mixture of both or pharmaceutically acceptable oils or fats. The liquid vehicle can contain other suitable pharmaceutical additives such as solubilisers, emulsifiers, buffers, preservatives, sweeteners, flavouring agents, suspending agents, thickening agents, colours, viscosity regulators, stabilizers or osmo-regulators. Suitable examples of liquid vehicles for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the vehicle can also be an oily ester such as ethyl oleate and isopropyl myristate. Sterile liquid vehicles are useful in sterile liquid form compositions for parenteral administration. The liquid vehicle for pressurized compositions can be a halogenated hydrocarbon or other pharmaceutically acceptable propellant.

Liquid pharmaceutical compositions, which are sterile solutions or suspensions, can be utilized by, for example, intramuscular, intrathecal, epidural, intraperitoneal, intravenous and particularly subcutaneous injection. The agent may be prepared as a sterile solid composition that may be dissolved or suspended at the time of administration using sterile water, saline, or other appropriate sterile injectable medium.

The agents and compositions of the invention may be administered orally in the form of a sterile solution or suspension containing other solutes or suspending agents (for example, enough saline or glucose to make the solution isotonic), bile salts, acacia, gelatin, sorbitan monoleate, polysorbate 80 (oleate esters of sorbitol and its anhydrides copolymerized with ethylene oxide) and the like. The agents used according to the invention can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

As discussed herein, the GM-CSF is elevated in subject's suffering from aortopathy conditions. These findings suggest that it can be used as a diagnostic tool or biomarker.

Hence, in a fifth aspect, there is provided use of granulocyte macrophage colony-stimulating factor (GM-CSF), or a variant or fragment thereof, as a biomarker for detecting or diagnosing aortopathy.

Preferably, SEQ ID No:2, or a variant or fragment thereof acts as a suitable biomarker, which may be detected. Preferably, SEQ ID No:2, or a variant or fragment thereof acts as an epitope which may be bound by an antibody or antigen-binding fragment, preferably the antibody or antigen-binding fragment used in accordance with the first aspect.

The invention also provides a kit for diagnosing patients suffering from aortopathy.

Hence, according to a sixth aspect of the invention, there is provided a kit for diagnosing a subject suffering from aortopathy, or a pre-disposition thereto, or for providing a prognosis of the subject's condition, the kit comprising:—
(i) detection means for detecting, in a sample obtained from a test subject, the concentration of granulocyte macrophage colony-stimulating factor (GM-CSF), or a variant or fragment thereof, and
(ii) a reference for the concentration of GM-CSF in a sample from an individual who does not suffer from aortopathy,
wherein the kit is configured to identify a difference in the concentration of GM-CSF in the bodily sample from the test subject compared to the reference, thereby suggesting that the test subject is suffering from aortopathy, or has a pre-disposition thereto, or providing a negative prognosis of the subject's condition.

According to a seventh aspect, there is provided a method for diagnosing a subject suffering from aortopathy, or a pre-disposition thereto, or for providing a prognosis of the subject's condition, the method comprising analysing the concentration of granulocyte macrophage colony-stimulating factor (GM-CSF), or a variant or fragment thereof, in a bodily sample obtained from a subject, and comparing this concentration with a reference for the concentration of GM-CSF in an individual who does not suffer from aortopathy, wherein a difference in the concentration of GM-CSF in the bodily sample from the test subject compared to the reference suggests that the subject is suffering from aortopathy, or has a pre-disposition thereto, or provides a negative prognosis of the subject's condition.

The subject may be any animal of veterinary interest, for instance, a cat, dog, horse etc. However, it is preferred that the subject is a mammal, such as a human, either male or female.

Preferably, a sample is taken from the subject, and the concentration of granulocyte macrophage colony-stimulating factor (GM-CSF), or a variant or fragment thereof may be measured in an assay. The kit may comprise sample extraction means for obtaining the sample from the test subject. The sample extraction means may comprise a needle or syringe or the like.

It has been demonstrated that GM-CSF occur in body and organ fluids. However, the sample may be any bodily sample into which GM-CSF is secreted, e.g. it may be lymph or interstitial fluid. The sample may be a urine sample or a blood sample. The blood sample may be venous or arterial.

The kit may comprise a sample collection container for receiving the extracted sample. It will be appreciated that "fresh" bodily samples, such as blood, may be analysed for GM-CSF levels immediately after they have been taken from a subject. Alternatively, the blood may be stored at low temperatures, for example in a fridge or even frozen before the GM-CSF assay is conducted. The sample may then be de-frosted and analysed at a later date.

Measurement of GM-CSF may be made on whole blood. However, the blood may be further processed before the assay is performed. For instance, an anticoagulant, such as citrate (such as sodium citrate), hirudin, heparin, PPACK, or sodium fluoride may be added. Thus, the sample collection container may contain an anticoagulant in order to prevent the blood sample from clotting. Alternatively, the blood sample may be centrifuged or filtered to prepare a plasma or serum fraction, which may be used for analysis. Hence, it is preferred that the GM-CSF or variant or fragment is analysed or assayed in a blood plasma or a blood serum sample. It is preferred that GM-CSF concentration is measured in vitro from a blood serum sample or a plasma sample taken from the subject.

As described in the examples, the inventors monitored the concentration of GM-CSF in KLF6fl/fl;LysM Cre mice under AngII infusion to induce aortic inflammation, and compared it to the GM-CSF concentration in control macrophages. They demonstrated that there was a statistically significant increase in the concentration of GM-CSF in the mice suffering from aortopathy induced by AngII infusion. Thus, the difference in concentration is preferably an increase compared to the reference control value, which is indicative of aortopathy.

It will be appreciated that the concentration of GM-CSF in aortopathy patients is highly dependent on a number of factors, for example how far the disease has progressed, and the age and gender of the subject. It will also be appreciated that the concentration of GM-CSF in individuals who do not suffer from aortopathy may fluctuate to some degree, but that on average over a given period of time, the concentration tends to be substantially constant. In addition, it should be appreciated that the concentration of GM-CSF in one group of individuals who do not suffer from aortopathy may be different to the concentration of GM-CSF in another group of individuals who do not suffer from the disease. However, the skilled technician will know how to determine the average concentration of GM-CSF in individuals who do not suffer from aotopathy, and this is referred to as the 'normal' concentration of GM-CSF. The normal concentration corresponds to the reference values discussed above.

The GM-CSF may be extracted from the bodily sample by a variety of techniques, and then detected. Detection may be achieved by an immunoassay (e.g. ELISA), for example using a monoclonal antibody specific for GM-CSF which has been pre-coated onto a substrate, such as a microplate. Standards and samples may be applied into the wells and any GM-CSF present is bound by the immobilised antibody. After washing away any unbound substances, an enzyme-linked monoclonal antibody for human GM-CSF may then be applied to the wells. Following a wash to remove any unbound antibody-enzyme reagent, a substrate solution may be applied to the wells and colour develops in proportion to the amount of GM-CSF bound in the initial step. The colour development may then be stopped, and the intensity of colour measured. A suitable assay for detecting GM-CSF may be as supplied by R&D systems.

The kit according to the invention comprises means for determining the concentration of GM-CSF in the bodily sample. The kit may comprise a container in which the means for determining the concentration of GM-CSF in the sample from a test subject may be contained. The kit may also comprise instructions for use.

Thus, the kit may comprise detection means for determining the concentration of the GM-CSF in the sample once this has been obtained from the subject.

The reference values may be obtained by assaying a statistically significant number of control samples (i.e. samples from subjects who do not suffer from aortopathy). Accordingly, the reference according to the kit of the invention may be a control sample for assaying purposes.

The detection means may comprise an assay adapted to determine the concentration of GM-CSF in the sample. The kit or method may comprise the use of a positive control and/or a negative control against which the assay may be compared. For example, the kit may comprise a reference for the concentration of GM-CSF in a sample from an individual who does (i.e. positive control) or does not (i.e. a negative control) suffer from aortopathy.

The kit may further comprise a label which may be detected. The term "label" can mean a moiety that can be attached to the antibody, or antigen binding fragment thereof. Moieties can be used, for example, for therapeutic or diagnostic procedures. Labels include, for example, moieties that can be attached to an anti-GM-CSF antibody or fragment thereof and used to monitor the binding of the antibody to GM-CSF or a fragment thereof. As described herein the antibody or antigen-binding fragment thereof binds specifically to SEQ ID No:2, or a variant or fragment thereof.

Diagnostic labels include, for example, moieties which can be detected by analytical methods. Analytical methods include, for example, qualitative and quantitative procedures. Qualitative analytical methods include, for example, immunohistochemistry and indirect immunofluorescence. Quantitative analytical methods include, for example, immunoaffinity procedures such as radioimmunoassay, ELISA or FACS analysis. Analytical methods also include both in vitro and in vivo imaging procedures. Specific examples of diagnostic labels that can be detected by analytical means include enzymes, radioisotopes, fluorochromes, chemiluminescent markers, and biotin.

A label can be attached directly to an anti-GM-CSF antibody, or antigen binding fragment thereof, or be attached to a secondary binding agent that specifically binds a molecule of the invention. Such a secondary binding agent can be, for example, a secondary antibody. A secondary antibody can be either polyclonal or monoclonal, and of human, rodent or chimeric origin.

In a further aspect, there is provided an anti-GM-CSF antibody for use in the treatment of a patient suffering from aortic dissection, wherein said antibody is administered to said patient in a manner to achieve a therapeutically effective antibody level in the blood of said patient.

In another aspect, there is provided a method of treating aortic dissection in a patient by measuring the presence of an increased level of GM-CSF in the blood compared to normal and then treating said patient with an anti-GM-CSF antibody.

The patient may have been diagnosed with aortic dissection and requires ongoing treatment to prevent further progression of the disease. The patient may have undergone surgical treatment for aortic dissection and requires ongoing treatment to prevent recurrence of the disease.

In a further aspect, there is provided a method of diagnosing patients suffering from or at risk of suffering from aortic dissection, comprising analysing the concentration of GM-CSF in a patient sample and comparing this concentration with a reference concentration of GM-CSF known to represent an elevated risk of aortic dissection.

The patient may have been diagnosed with aortic dissection and requires ongoing treatment to prevent further progression of the disease. The patient may have undergone surgical treatment for aortic dissection and requires ongoing treatment to prevent recurrence of the disease. The patient sample may comprise a blood sample.

It will be appreciated that the invention extends to any nucleic acid or peptide or variant, derivative or analogue thereof, which comprises or consists of substantially the amino acid or nucleic acid sequences of any of the sequences referred to herein, including variants or fragments thereof. The terms "substantially the amino acid/nucleotide/peptide sequence", "variant" and "fragment", can be a sequence that has at least 40% sequence identity with the amino acid/nucleotide/peptide sequences of any one of the sequences referred to herein, for example 40% identity with the sequence identified as SEQ ID No: 2 (i.e. GM-CSF protein), and so on.

Amino acid/polynucleotide/polypeptide sequences with a sequence identity which is greater than 50%, more preferably greater than 65%, 70%, 75%, and still more preferably greater than 80% sequence identity to any of the sequences referred to are also envisaged. Preferably, the amino acid/polynucleotide/polypeptide sequence has at least 85% identity with any of the sequences referred to, more preferably at least 90%, 92%, 95%, 97%, 98%, and most preferably at least 99% identity with any of the sequences referred to herein.

The skilled technician will appreciate how to calculate the percentage identity between two amino acid/polynucleotide/polypeptide sequences. In order to calculate the percentage identity between two amino acid/polynucleotide/polypeptide sequences, an alignment of the two sequences must first be prepared, followed by calculation of the sequence identity value. The percentage identity for two sequences may take different values depending on: —(i) the method used to align the sequences, for example, ClustalW, BLAST, FASTA, Smith-Waterman (implemented in different programs), or structural alignment from 3D comparison; and (ii) the parameters used by the alignment method, for example, local vs global alignment, the pair-score matrix used (e.g. blosum62, pam250, gonnet etc.), and gap-penalty, e.g. functional form and constants.

Having made the alignment, there are many different ways of calculating percentage identity between the two sequences. For example, one may divide the number of identities by: (i) the length of shortest sequence; (ii) the length of alignment; (iii) the mean length of sequence; (iv) the number of non-gap positions; or (iv) the number of equivalenced positions excluding overhangs. Furthermore, it will be appreciated that percentage identity is also strongly length dependent. Therefore, the shorter a pair of sequences is, the higher the sequence identity one may expect to occur by chance.

Hence, it will be appreciated that the accurate alignment of protein or DNA sequences is a complex process. The popular multiple alignment program ClustalW (Thompson et al., 1994, Nucleic Acids Research, 22, 4673-4680; Thompson et al., 1997, Nucleic Acids Research, 24, 4876-4882) is a preferred way for generating multiple alignments of proteins or DNA in accordance with the invention. Suitable parameters for ClustalW may be as follows: For DNA alignments: Gap Open Penalty=15.0, Gap Extension Penalty=6.66, and Matrix=Identity. For protein alignments: Gap Open Penalty=10.0, Gap Extension Penalty=0.2, and Matrix=Gonnet. For DNA and Protein alignments: END-GAP=−1, and GAPDIST=4. Those skilled in the art will be aware that it may be necessary to vary these and other parameters for optimal sequence alignment.

Preferably, calculation of percentage identities between two amino acid/polynucleotide/polypeptide sequences may then be calculated from such an alignment as (N/T)*100, where N is the number of positions at which the sequences share an identical residue, and T is the total number of positions compared including gaps but excluding overhangs. hence, a most preferred method for calculating percentage identity between two sequences comprises (i) preparing a sequence alignment using the clustalw program using a suitable set of parameters, for example, as set out above; and (ii) inserting the values of n and t into the following formula: —sequence identity=(N/T)*100.

Alternative methods for identifying similar sequences will be known to those skilled in the art. For example, a substantially similar nucleotide sequence will be encoded by a sequence which hybridizes to any of the nucleic acid sequences shown herein, or their complements under stringent conditions. By stringent conditions, we mean the nucleotide hybridises to filter-bound DNA or RNA in 3× sodium chloride/sodium citrate (SSC) at approximately 45° C. followed by at least one wash in 0.2×ssc/0.1% SDS at approximately 20-65° c. Alternatively, a substantially similar polypeptide may differ by at least 1, but less than 5, 10, 20, 50 or 100 amino acids from the sequences shown herein.

Due to the degeneracy of the genetic code, it is clear that any nucleic acid sequence described herein could be varied or changed without substantially affecting the sequence of the protein encoded thereby, to provide a functional variant thereof. Suitable nucleotide variants are those having a sequence altered by the substitution of different codons that encode the same amino acid within the sequence, thus producing a silent change. Other suitable variants are those having homologous nucleotide sequences but comprising all, or portions of, sequence, which are altered by the substitution of different codons that encode an amino acid with a side chain of similar biophysical properties to the amino acid it substitutes, to produce a conservative change. For example small non-polar, hydrophobic amino acids include glycine, alanine, leucine, isoleucine, valine, proline, and methionine. Large non-polar, hydrophobic amino acids include phenylalanine, tryptophan and tyrosine. The polar neutral amino acids include serine, threonine, cysteine, asparagine and glutamine. The positively charged (basic) amino acids include lysine, arginine and histidine. The negatively charged (acidic) amino acids include aspartic acid and glutamic acid. It will therefore be appreciated which amino acids may be replaced with an amino acid having similar biophysical properties, and the skilled technician will know the nucleotide sequences encoding these amino acids.

All of the features described herein (including any accompanying claims, abstract and drawings), and/or all of the steps of any method or process so disclosed, may be combined with any of the above aspects in any combination, except combinations where at least some of such features and/or steps are mutually exclusive.

For a better understanding of the invention, and to show how embodiments of the same may be carried into effect, reference will now be made, by way of example, to the accompanying Figures, in which:—

Figure 5A:
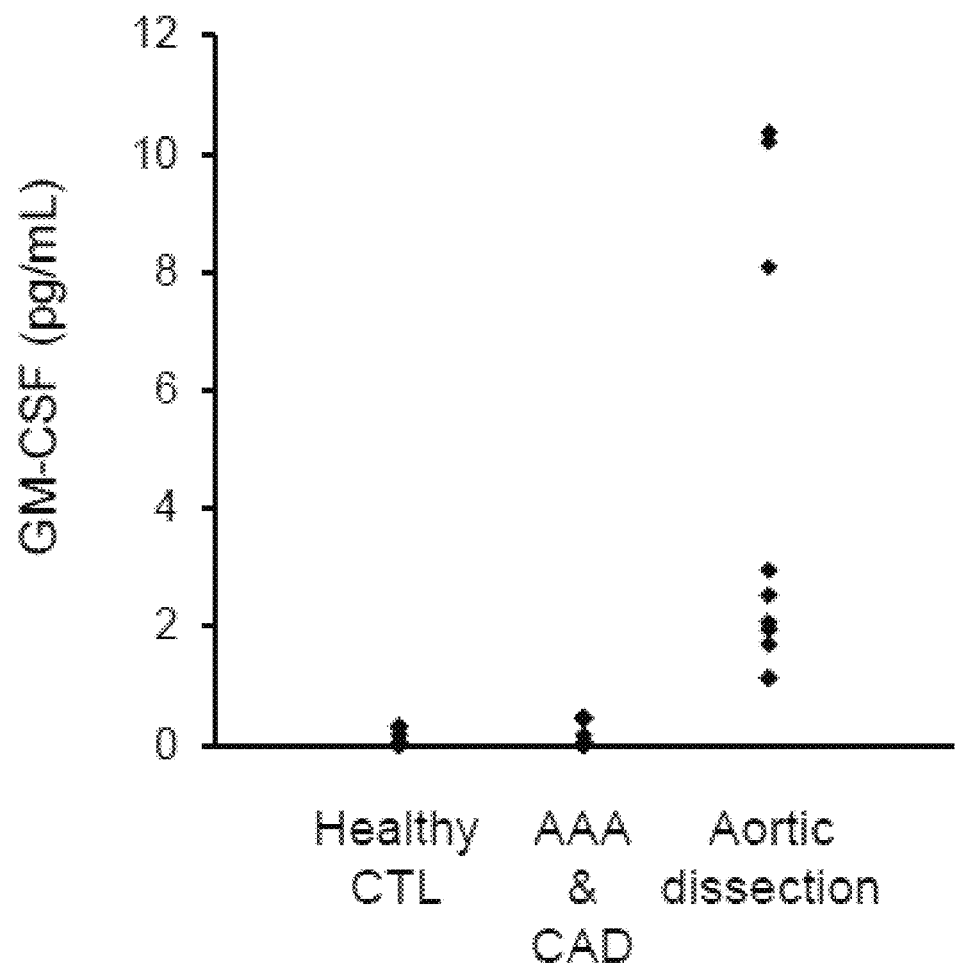
Figure 5B:
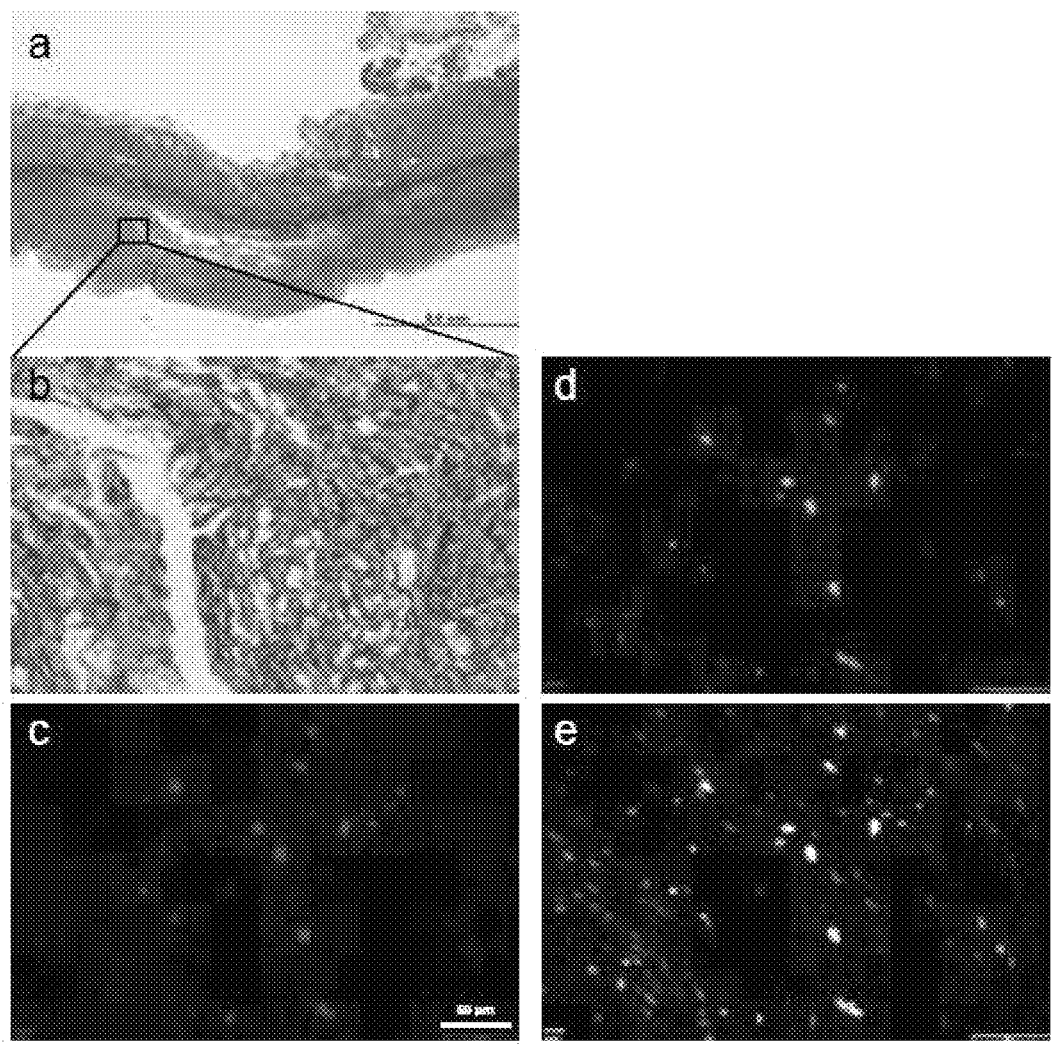
Figure 6A:
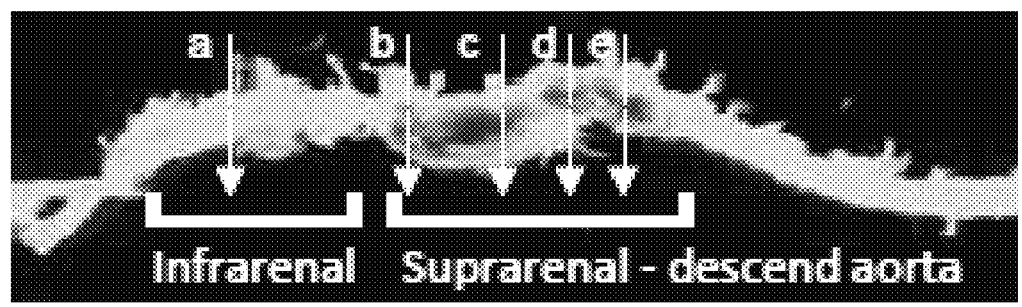
Figure 6B:
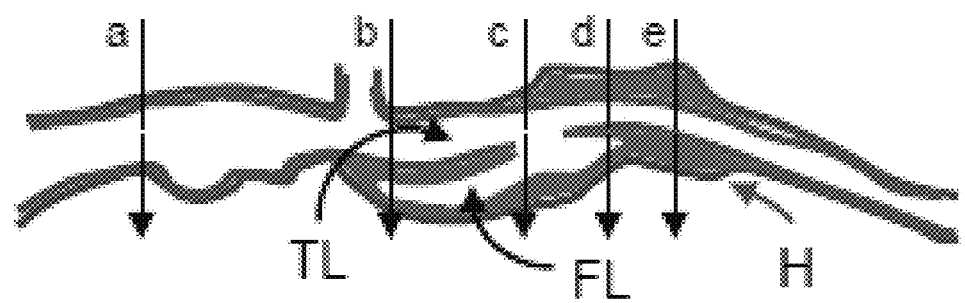
Figure 6D:
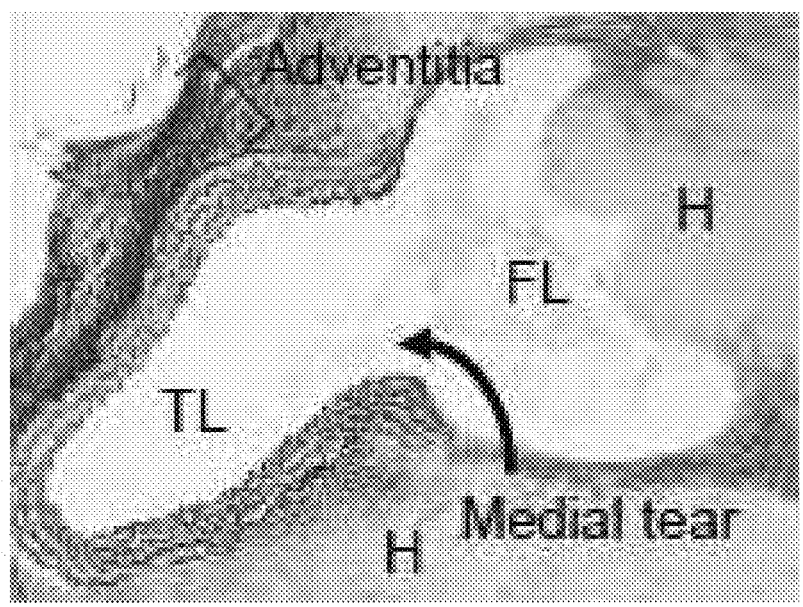
Figure 6C:
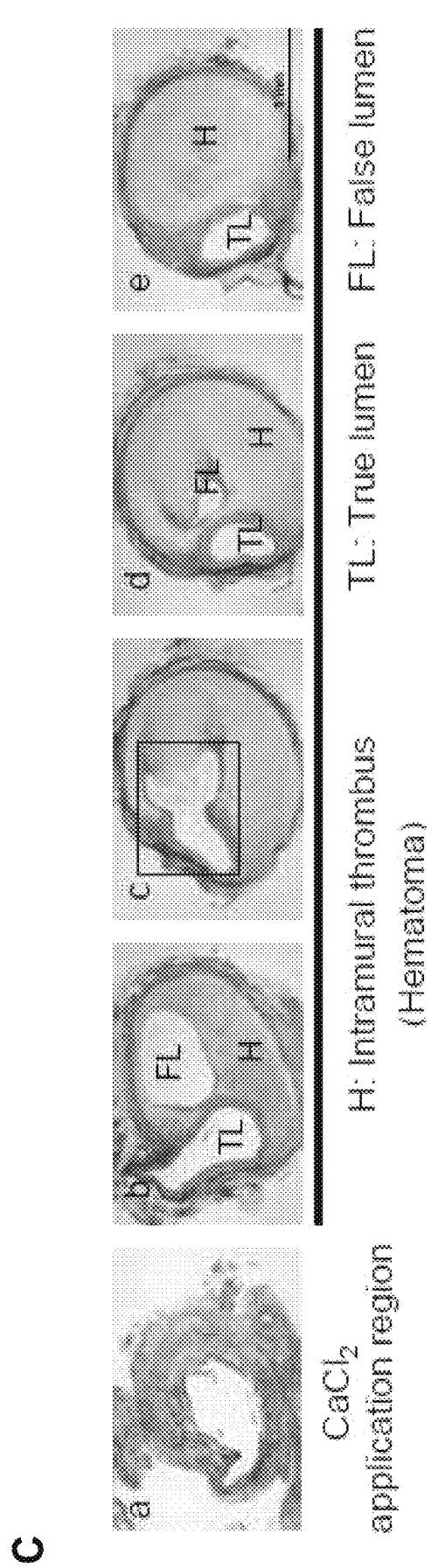
Figure 7A:
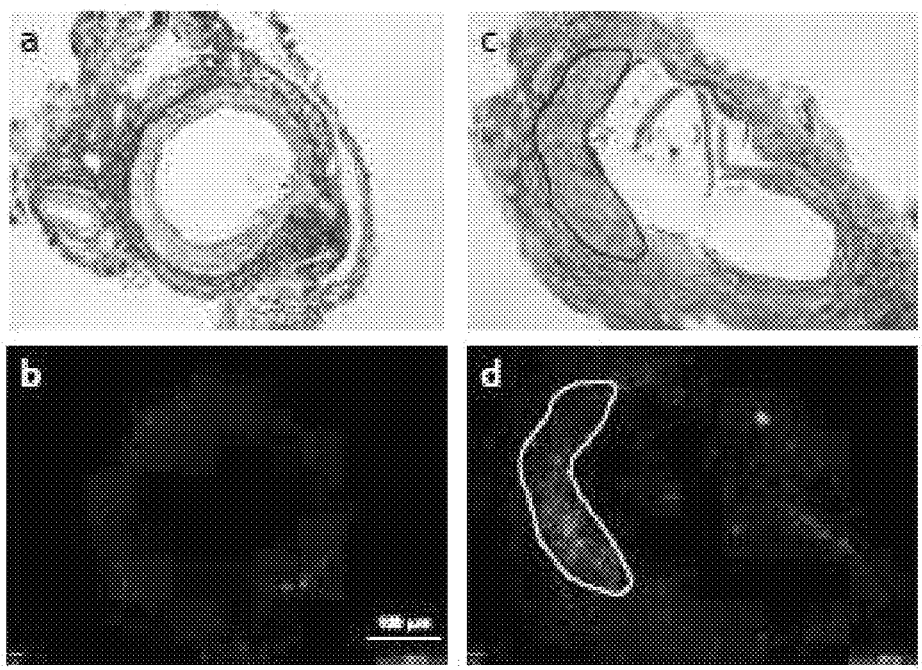
Figure 7B:
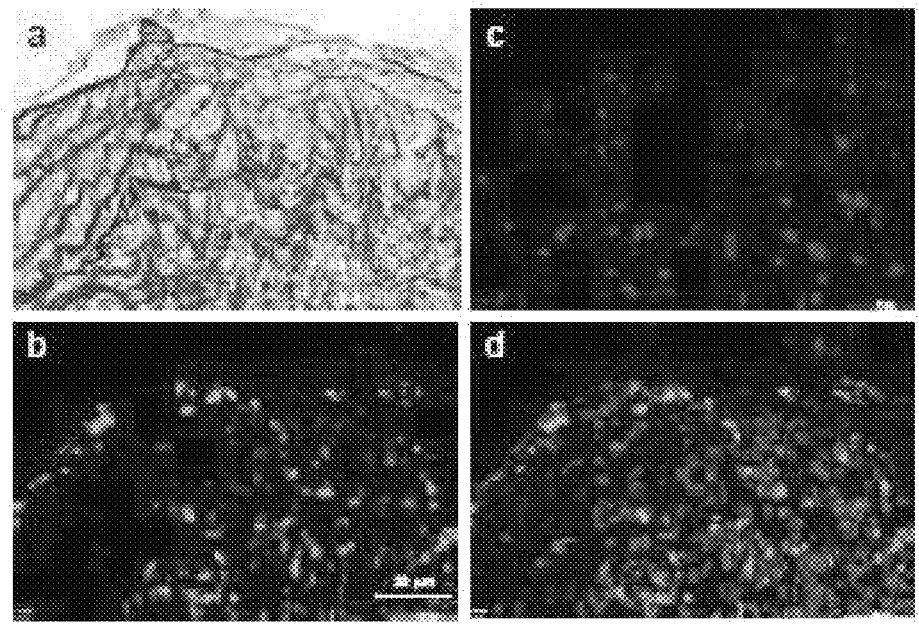
Figure 11A:
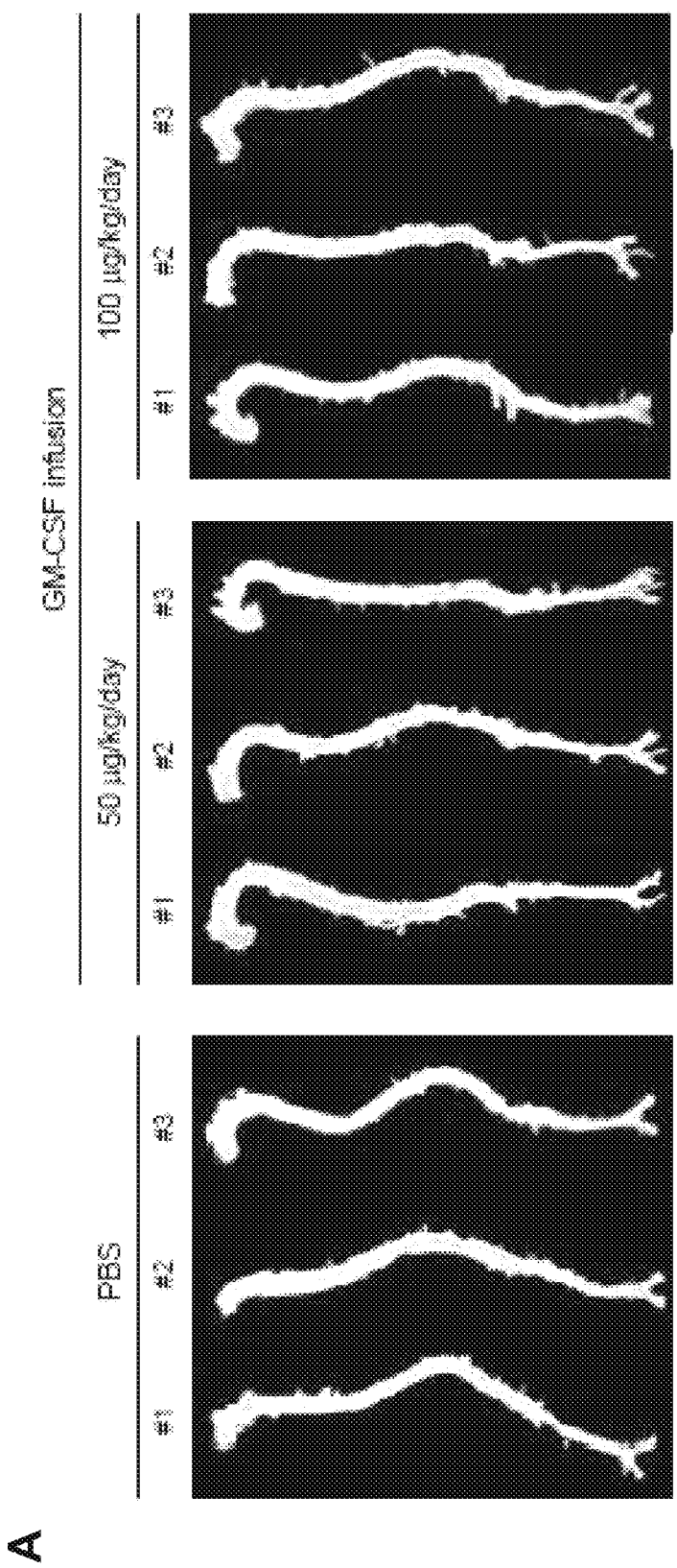
Figure 11B:
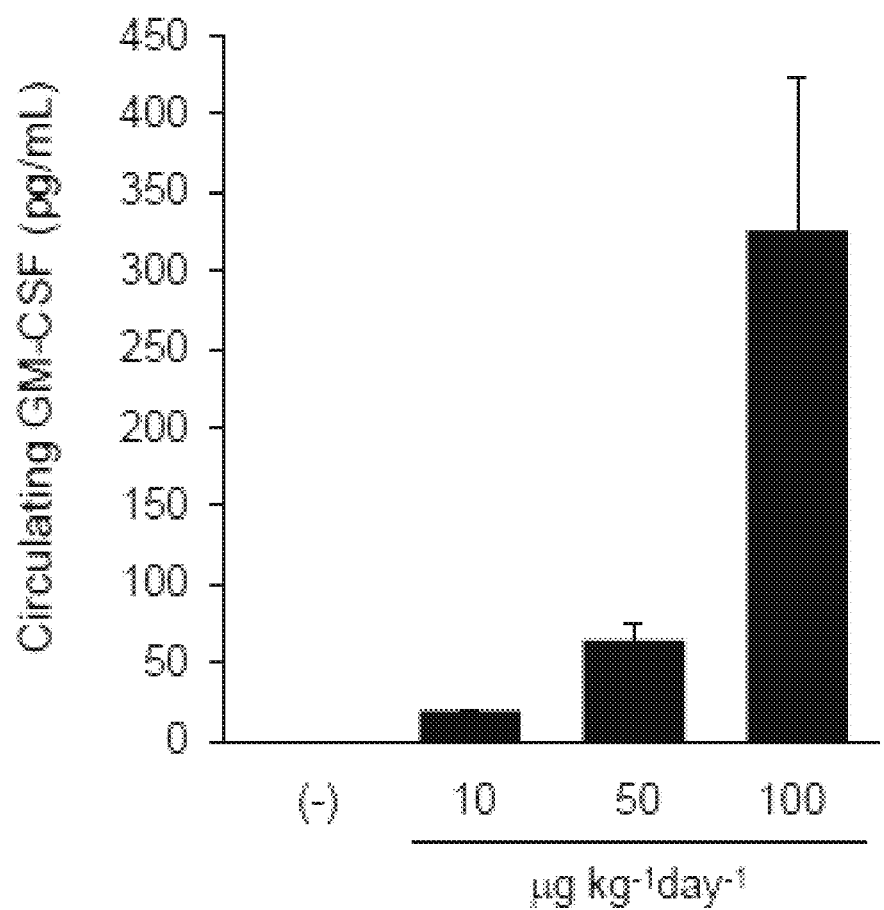
Figure 12A:
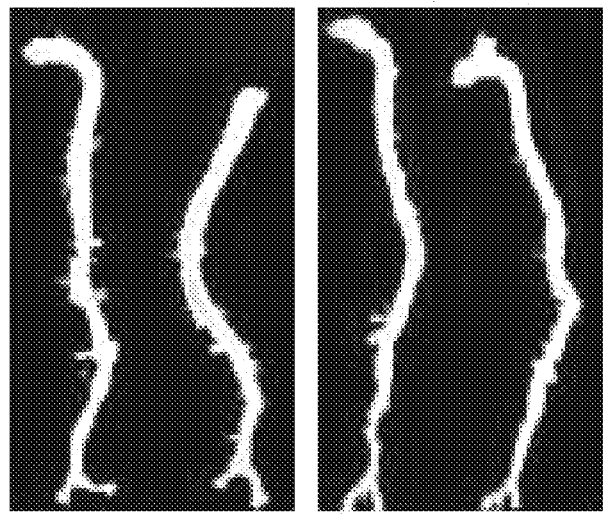
Figure 12A:
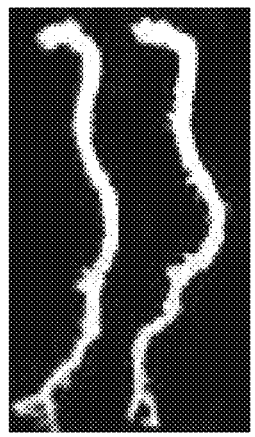
Figure 12A:
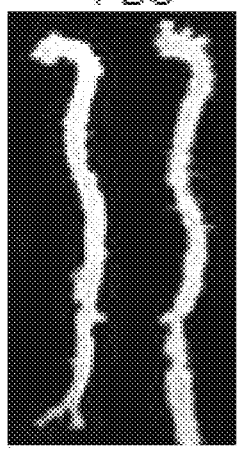
Figure 12A:
Figure 12B:
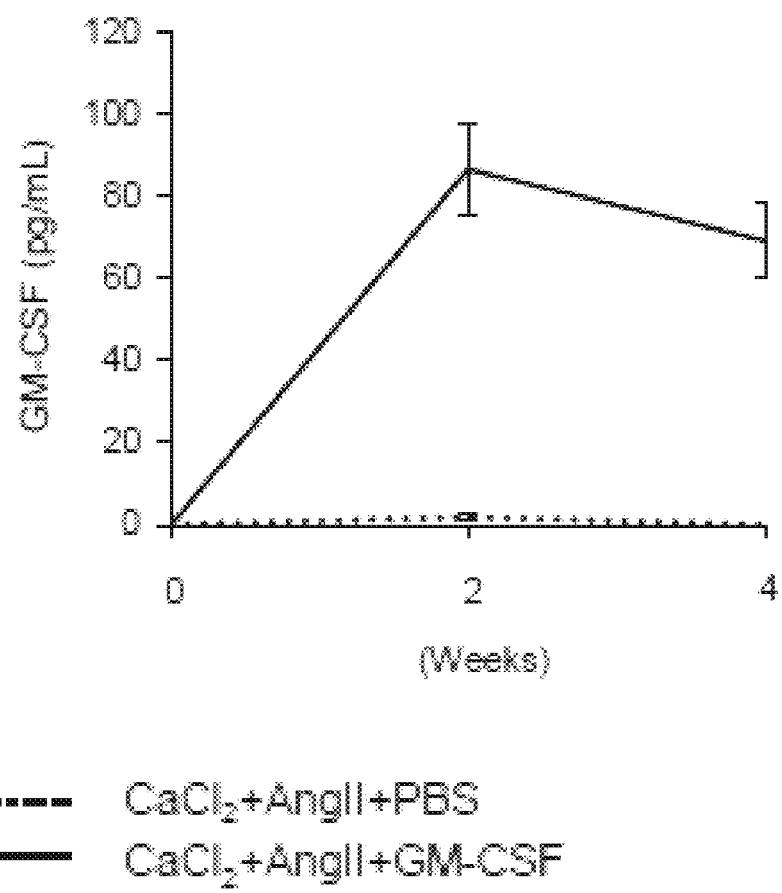
Figure 13A:
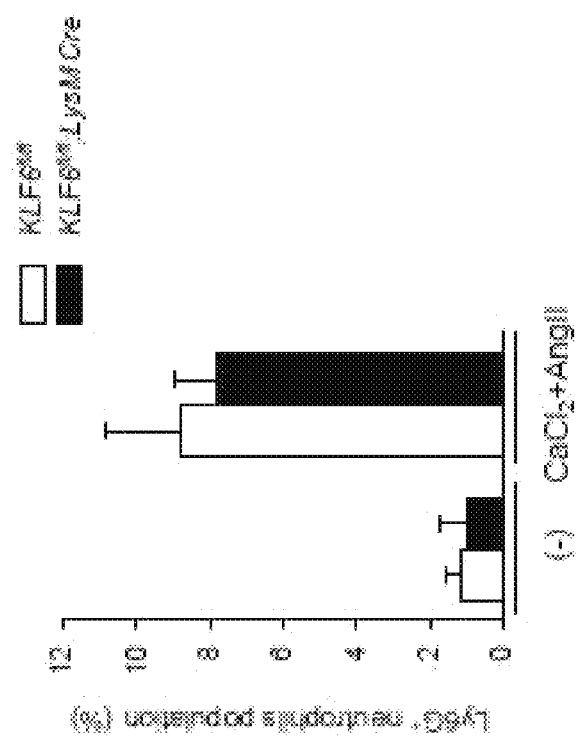
Figure 13A:
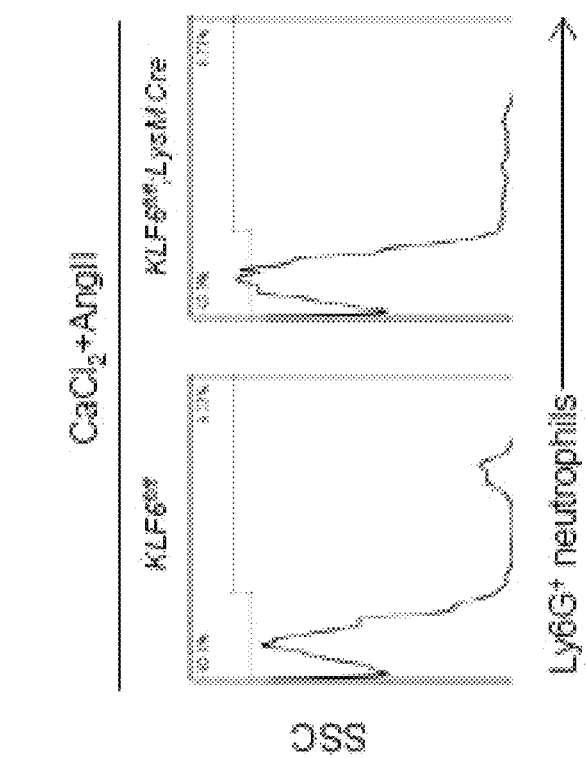
Figure 13B:
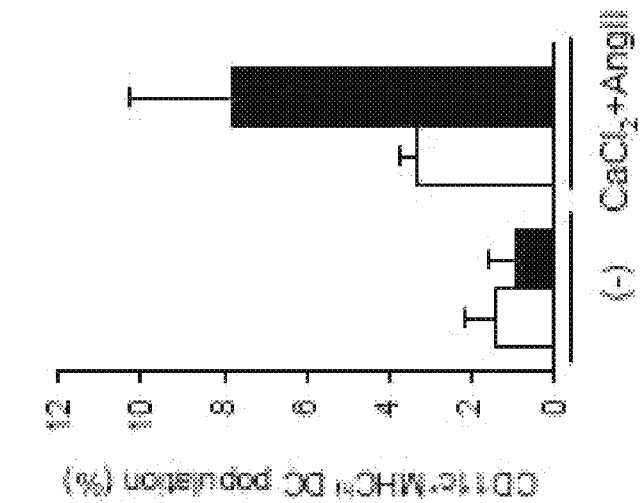
Figure 13B:
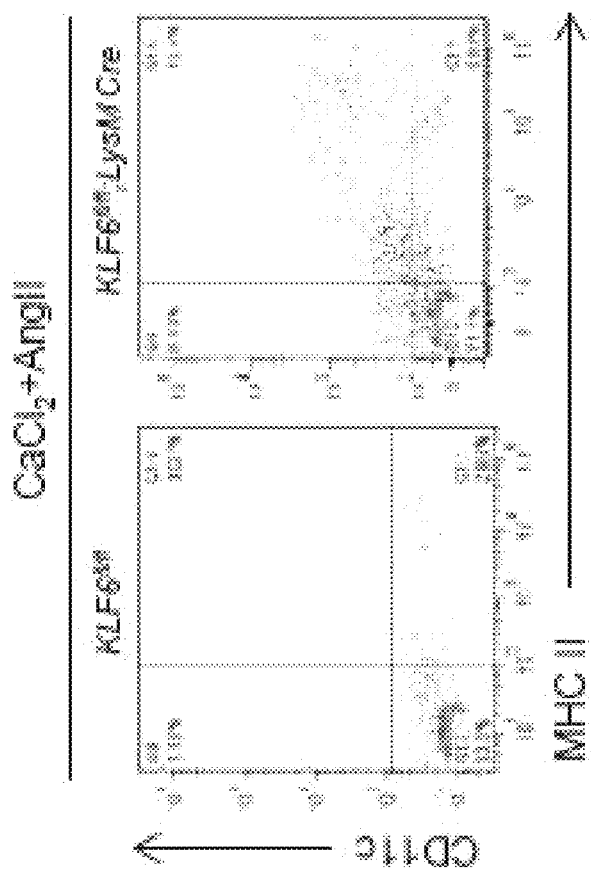

FIGS. 1A-1H show aortic aneurysm and inflammation in KLF6 heterozygous knockout mice. (A) Representative aorta (infrarenal aorta:hash, suprarenal aorta:asterisk) induced by 2 weeks of AngII infusion with CaCl2 application in wild-type (WT) littermates (n=11) and KLF6 heterozygous knockout (KLF6+/−, n=10) mice. Histopathological analysis of infrarenal (B) and suprarenal aorta (C) by EVG (upper panels, a and c) and H&E staining (lower panels, b and d). (D) Quantification of infrarenal aortic diameters between wild-type (WT) littermates and KLF6 heterozygous knockout (K6+/−) mice before [(−), n=3] and after 2 weeks of AngII infusion with CaCl2 application (CaCl2+AngII, WT; n=10, K6+/−; n=8). *P<0.05, Student's t-test. (E) Immunofluoresent staining for macrophages (green; Mac3, blue; DAPI) in boxed area of EVG-stained aorta (b) of wild-type littermates and KLF6 heterozygous knockout mice. (F) Expression of RNA levels of MMP9, F4/80 and IL-6 in aorta from wild-type (WT) littermates and KLF6 heterozygous knockout (K6+/−) mice before [(−), n=3] and after AngII infusion with CaCl2 application (CaCl2+AngII, n=5) as examined using real-time PCR and normalized by GAPDH mRNA. *P<0.05, Mann-Whitney test. (G) Inhibitory effect of clodronate-liposomes on aortic phenotype (n=4) compared with PBS-liposome administered mice (n=$_5$) by EVG (left panels, a and b); H&E (middle panels, c and d); and F4/80 staining (right panels, e and f, immunohistochemistry). (H) Quantification of infrarenal aortic diameters from clodronate-liposome- or PBS-liposome-administered mice (*P<0.05, Student's t-test, n=4 or 5 mice per group). Results are from three independent experiments. All values are presented as means±s.e.m;

FIGS. 2A-2I show myeloid deficiency of KLF6 shows a phenotype of aortic dissection/intramural hematoma and inflammation. (A) Survival curve between KLF6fl/fl control mice (n=19) and KLF6fl/fl;LysMCre mice (n=22) with CaCl2 application and AngII infusion. (B) Representative aorta of KLF6fl/fl control mice (A) and KLF6fl/fl;LysMCre mice (n=19) after 2 weeks of AngII infusion with CaCl2 application (infrarenal aorta:hash, suprarenal aorta:asterisk). Representative histopathological analysis of infrarenal (C) and suprarenal aorta (D) observed in KLF6fl/fl;LysMCre mice by EVG (upper panels, a and c) and H&E staining (lower panels, b and d) after 2 weeks of AngII infusion with CaCl2 application as compared with KLF6fl/fl control mice. (E) Quantification of infrarenal aortic diameters before [(−), n=3] and after 2 weeks of AngII infusion with CaCl2 application (CaCl2+AngII, n=5). (F) Plasma concentration of IL-6 in KLF6fl/fl mice (n=$_7$) and KLF6fl/fl;LysMCre mice (n=9) after 2 weeks of AngII infusion with CaCl2 application. *P<0.05, Student's t-test (e, f) (G) Expression of RNA levels of IL-6 were examined in aorta from KLF6fl/fl mice and KLF6fl/fl;LysMCre mice before [(−), n=3] and after 2 weeks of AngII infusion with CaCl2 application (CaCl2+AngII, n=5) using real-time PCR and normalized by GAPDH mRNA. (H) Expression of RNA levels of IL-6, CCR2, TNFα, IL-1β, iNOS and MCP-1 were examined in bone marrow-derived macrophages subjected to AngII stimulation (10 μM) for 3 h (n=3 mice per group). (I) Population of CD11b+Ly6Chi-cells in aorta, peripheral blood, spleen and bone marrow in KLF6fl/fl mice and KLF6fl/fl;LysMCre mice after 2 weeks of AngII infusion with CaCl2 application. Results represent three independent experiments. All values are presented as means± s.e.m. *P<0.05, Mann-Whitney test (g, h);

FIGS. 3A-3E show GM-CSF is a direct target of KLF6 in macrophages. (A) RT2 profiler PCR array analysis of genes related to IL-6/STAT3 inflammatory pathway between bone marrow (BM)-derived macrophages from KLF6fl/fl mice and KLF6fl/fl;LysMCre mice with AngII stimulation (10 μM) for 3 h. Arrow indicates GM-CSF. List of genes that showed consistent changes between BM-derived macrophages from KLF6fl/fl mice and KLF6fl/fl;LysMCre mice stimulated with AngII (10 μM) for 3 h. (B) mRNA expression of GM-CSF in aortic macrophages obtained from KLF6fl/fl mice [sham; (−), n=3; CaCl2+AngII; n=3] and KLF6fl/fl;LysMCre mice [sham; (−), n=3; CaCl2+AngII; n=6]. N.D. indicates not detected. (C) mRNA expression of GM-CSF in aorta of KLF6fl/fl mice and KLF6fl/fl;LysMCre mice at 0 (n=3), 3 (n=3), 7 (n=3) and 14 (n=4) days. (D) Immunohistochemistry for macrophages (red; F4/80, b), GM-CSF (green, c) and nucleus (blue; DAPI, d) in aorta of KLF6fl/fl;LysMCre mice with EVG stained infrarenal aorta (a). (E) Plasma GM-CSF concentration between KLF6fl/fl mice (n=8) and KLF6fl/fl;LysMCre mice (n=4) after 2 weeks of AngII infusion with CaCl2 application. Results represent three independent experiments. All values are presented as means±s.e.m. *P<0.05, Mann-Whitney test;

FIGS. 4A-4J show GM-CSF is required for aortic dissection/intramural hematoma. (A) Representative aortas of KLF6fl/fl;LysMCre mice with administration of anti-GM-CSF neutralizing antibody (B, anti-GM-CSF, n=8) or control IgG antibody (a, n=10) after 2 weeks of AngII infusion with CaCl2 application. Quantification of infrarenal aortic diameters (b, anti-GM-SCF; n=$_7$, anti-control IgG; n=9) and plasma concentration of IL-6 (C, n=$_5$ or 6) between anti-GM-CSF antibody-administered and anti-control IgG-administered mice. *P<0.05, Student's t-test. (D) Expression levels of RNA of GM-CSFRα, MMP9, F4/80 and IL-6 were examined in aorta of anti-GM-CSF antibody-administered mice or anti-control IgG administered mice using real-time PCR then normalized by GAPDH mRNA (n=$_5$ mice per group). (E) Survival curve of mice with administration of recombinant GM-CSF (n=26) or PBS (n=19) with CaCl2 application and AngII infusion in wild-type mice. (F) Representative aorta of wild-type mice with administration of recombinant GM-CSF (b) or PBS (a) with CaCl2 application and AngII infusion (infrarenal aorta:hash, suprarenal aorta: asterisk) for 4 weeks. (G) Histopathological analysis of infrarenal aorta (upper panels, a and c) and suprarenal aorta (lower panels, b and d) by EVG staining (H) Quantification of infrarenal aortic diameters between recombinant GM-CSF-administered mice or PBS-administered mice [sham; (−) n=3, CaCl2+AngII; n=5]. (I) Plasma GM-CSF concentration after 2 weeks infusion of recombinant GM-CSF or PBS with or without CaCl2 application and AngII infusion (n=3-5 mice per group). (J) Expression levels of RNA of F4/80 and IL-6 were examined in aorta from mice administered recombinant GM-CSF or PBS using real-time PCR then normalized with GAPDH mRNA [sham; (−) n=3, CaCl2+AngII n=5]. Results are from three independent experiments. All values are presented as means±s.e.m. *P<0.05, Mann-Whitney test (d, h, j) and one-way ANOVA with Dunn's post test (i);

FIGS. 5A-5B show increased GM-CSF in patients with acute aortic dissection. (A) Plasma GM-CSF concentration in healthy volunteers (healthy CTL, n=12) and patients with aortic aneurysm (AAA, n=3), coronary artery disease (CAD, n=ii) or aortic dissection (n=10). (B) Immunofluorescent staining for CD68 (red, c), GM-CSF (green, d) and DAPI (blue, e) in descending dissected aorta (boxed area, a) with EVG staining (b);

FIGS. 6A-6C show aortic dissection/intramural hematoma on aneurysm in the present model. (A) Appearance of the excised thoracic-abdominal aorta subjected to CaCl2 application and AngII infusion. Note that intramural thrombus formation is present in the suprarenal region. (B) Schematic illustration of the diseased aorta. (C) Cross-sectional histological sections stained by Elastica van Gieson. Note that a-e in correspond to the same levels of the aorta (a). a; Cross section of the infrarenal abdominal aorta (CaCl2 application level). b; at the level of the renal arteries. c; suprarenal level where the intima-medial layer shows a tear. d and e; suprarenal descending thoracic aorta beyond the intimamedial tear. (D) High-magnification cross section at the suprarenal level (c). Intima-medial tear and false lumen/mural thrombus formation are present;

FIGS. 7A-7B show marked infiltration of macrophages in the aneurysmal aorta. (A) Infiltrated macrophages were visualized by immunofluorescent staining (dotted line, green, Mac3) in aorta of KLF6fl/fl;LysMCre mice (right panels, c and d) compared to KLF6fl/fl mice (left panels, a and b). (B) Immunofluorescent staining for macrophages (b, green, Mac3), pSTAT3 (c, red) and nuclei (d, DAPI, blue) in diseased aorta (a) of KLF6fl/fl;LysMCre mice;

FIGS. 8A-8D show involvement of TGFβ-mediated pathways. Expression of mRNA levels of TGFβ1-related factors in aorta from wild-type (WT) littermates and KLF6+/−mice (A), and in KLF6fl/fl and KLF6fl/fl;LysM Cre mice (C) using real-time PCR normalized by GAPDH mRNA. n=$_5$ per group. All values are presented as mean±s.e.m. Western blot analysis for pSmad2, Smad2, pERK1/2, EMU/2, pSTAT3, STAT3 or GAPDH in aorta before (−) and after 2 weeks of AngII infusion with CaCl2 application (CaCl2+AngII) in wild-type (WT) littermates and KLF6+/−mice (B) and in KLF6fl/fl and KLF6fl/fl;LysM Cre mice (D);

FIGS. 9A-9E show effects of LysM Cre on neutrophils and dendritic cells in peripheral blood. Population and quantification of Ly6G+ neutrophils (A, C) and Lineage-CD11c+ dendritic cells (DC) (B, D) in peripheral blood of KLF6fl/fl mice and KLF6fl/fl;LysMCre mice after sham (−) or 2 weeks of AngII infusion with CaCl2 application (CaCl2+AngII). (E) Expression levels of RNA of IL-1β, TNFα, IL-6 and IL-8 were examined in neutrophils isolated from bone-marrow of KLF6fl/fl mice and KLF6fl/fl; LysM-Cre mice after sham (−) or 2 weeks of AngII infusion with CaCl2 application (CaCl2+AngII). n=5 per group. All values are presented as means±s.e.m;

FIGS. 10A-10D show GM-CSF is regulated by KLF6 in macrophages. mRNA expression (A) and concentration of GM-CSF in medium (B) of bone marrow-derived macrophages from KLF6fl/fl mice (n=4) and KLF6fl/fl;LysMCre mice (n=4) stimulated with AngII mM), TNFα (10 ng ml−1) and IL-1β (20 ng ml−1) for the indicated period. (C) Macrophages from KLF6fl/fl mice were infected with empty (E) or KLF6 (KLF6)-expressing retrovirus construct. Total RNA was harvested 3 h after stimulation with AngII mM), TNFα ng ml−1) and IL-1β (20 ng ml−1). (D) ChIP assay was performed using antibody against KLF6 or control (CTL) IgG with chromatin extract with or without AngII mM), TNFα (10 ng ml−1) and IL-1β (20 ng ml−1) treatment for 3 h in macrophages from KLF6fl/fl mice (n=3). The results represent three independent experiments. All values are presented as means±s.e.m. *p<0.05 vs. KLF6fl/fl mice. P-value was calculated by Mann-Whitney test (a, b, d) and by one-way ANOVA with Dunn's post test (c);

FIGS. 11A-11B show concentration-dependent effects of GM-CSF administration on aortic dissection in wild-type mice. (A) Aorta after 2 weeks infusion of indicated concentrations of recombinant GM-CSF or PBS. (B) Plasma GM-CSF concentration after 2 weeks infusion of indicated concentrations of recombinant GM-CSF or PBS. n=3-5 per group. All values are presented as means±s.e.m;

FIGS. 12A-12B show long-term effect of GM-CSF administration on aortic dissection in wildtype mice. (A) Representative aorta with 2 weeks- or 4 weeks-administration of recombinant GM-CSF (10 mg kg−1 per day) or PBS with CaCl2 application and AngII infusion in wild-type mice. (B) Plasma GMCSF concentration after 2 weeks- or 4 weeks-infusion of recombinant GM-CSF (10 mg kg−1 per day) or PBS with CaCl2 application and AngII infusion in wild-type mice. n=4-5 per group. All values are presented as mean±s.e.m.; and FIGS. 13A-13B show effects of LysM Cre on neutrophils and dendritic cells in the aorta. Population and quantification of Ly6G+ neutrophils (A) and CD11c+MHC+ dendritic cells (DC) (B) in the aorta of KLF6fl/fl and KLF6fl/fl; LysMCre mice after sham (−) or 2 weeks of AngII infusion with CaCl2 application (CaCl2+AngII). n=3-4 per group. All values are presented as means±s.e.m.

EXAMPLES

Materials and Methods

Mice

Heterozygous KLF6+/− mice (C57BL/6) were originally generated by Tarocchi et al (50). To generate macrophage-specific KLF6-knockout mice, KLF6fl/fl mice (C57BL/6; 129Sv) were cross-bred with LysM Cre mice (C57BL/6, Jackson laboratory) (51). Only male mice 10- to 13-weeks of age and C57BL/6 as wild-type mouse (CLEA Japan) were used. All animal experiments were approved by the University of Tokyo ethics committee for animal experiments and strictly adhered to the guidelines for animal experiments of the University of Tokyo.

Murine Aortic Dissection/Intramural Hematoma Model

To induce aortic dissection/intramural hematoma, periaortic application of CaCl2 was done to the abdominal aorta, followed by two-week infusion of AngII (2000 ng kg−1 min−1) (40). In detail, mice were anesthetized and underwent laparotomy at 10- to 13-weeks of age. The abdominal aorta between the renal arteries and bifurcation of the iliac arteries was isolated from the surrounding retroperitoneal structure, and 0.5 M CaCl2 was applied to the external surface of the infrarenal aorta. NaCl (0.9%) was substituted for CaCl2 in sham control mice. The aorta was rinsed with 0.9% sterile saline after 15 min and the incision was closed.

Macrophage Depletion and Manipulation of GM-CSF

Wild-type mice were injected intraperitoneally with 110 mg kg−1 of clodronate liposomes or equal volume of PBS liposomes 2 days prior and 7 days after induction of aortic dissection. Neutralizing antibody against GM-CSF (300 μg, R&D systems) or control anti-rat IgG antibody (Equitech Bio) was administered every other day by intraperitoneal injection. Recombinant murine GM-CSF (10, 50, 100 μg kg−1 day−1, PeproTech) was administered for two weeks or four weeks after induction of aortic dissection.

Histological Analysis and Immunohistochemistry

Aortas from mice were embedded in paraffin then 5-μm-thick serial sections were prepared for Elastic Von Gienson (EVG) and hematoxylin/eosin (HE) staining. Digital images of EVG-stained aortas with reference scale were used for absolute measurement of diameter. Human aortic tissue was obtained from patients undergoing surgical aortic repair with informed consent under a protocol approved by the University of Tokyo hospital research ethics committee. Paraffin-embedded sections were taken from the aorta for EVG staining and immunohistochemistry. For immunohistochemistry, after deparaffinization and blocking, serial sections were incubated with the following antibodies; Mac-3 (dilution 1:200; rat; BD Pharmingen) or F4/80 (1:100; rat; Serotec) for macrophages in mice and CD68 (1:50; mouse; DAKO) in humans, and GM-CSF (1:100; rabbit; Abcam for mouse and 1:50; rabbit; Acris for humans) or p-STAT3 (1:200; rabbit; Cell Signaling Technology), then followed by biotinylated secondary antibodies (1:200; DAKO). For detection, anti-streptavidin-conjugated AlexFluor 488 or AlexFluor 594 (1:200; Invitrogen) was used. The nuclei were stained with 4', 6-diamidino-2-phenylindole (1:5,000; Sigma-Aldrich) after the final series of washes.

Cells Preparation from Aorta, Spleen, Bone Marrow and Blood

Aortas were minced into 3- to 4-mm pieces and placed in 1 ml digestion solution containing collagenase type II (1.25 mg ml−1, Worthington) and porcine pancreatic elastase (50 μg ml−1, Worthington) in base solution of Accumax (Innovative Cell Technologies). Aortic tissue was digested at room temperature with agitation for 1 h. After digestion, cells were washed in FACS buffer (5% FCS in PBS) at 2000 rpm for 5 min. Aortic macrophages were isolated using CD11b microbeads according to the manufacturer's instructions (Miltenyi Biotec). Spleen was homogenized and passed through a cell strainer to obtain single-cell suspensions. Bone marrow-derived cells were taken from the femur and tibia of 5- to 6-week-old mice. Blood was collected in heparin-coated vials and then 1.2% dextran was added for 45 min at room temperature. Counting of peripheral leukocytes was done by automated hematology analyzer (XT-2000i, Sysmex). Neutrophils were isolated from bone marrow using a neurophil isolation kit according to the manufacturer's instructions (Miltenyi Biotec). From single-cell suspensions of spleen, bone marrow and blood, erythrocytes were lysed using ACK lysis buffer for 5, 3 and 2 min on ice, respectively. Cells were centrifuged at 2000 rpm for 5 min to remove the ACK lysis buffer, then the single-cell suspensions were resuspended and washed in FACS buffer, followed by centrifugation at 2000 rpm for 5 min.

Cell Cultures

Bone marrow-derived cells were prepared from femur and tibia of KLF6fl/fl mice or KLF6fl/fl;LysM Cre mice to assess the role of GM-CSF in macrophages. KLF6 overexpression was induced by retrovirus construct for KLF6 (pMXs-KLF6) in the presence of RetroNectin (5 μg/cm2, Takara Bio.).

Flow Cytometry

Murine Fc receptors were blocked using antibodies against murine CD16/32 antigens (eBioscience) for 15 min on ice after which cells were washed and then resuspended in 100 l FACS buffer. Fluorochrome-conjugated antibodies (all from BioLegend) for APC-CD11b[M1/70], PerCP-Cy5.5-Ly-6c[HK1.4], APC-Cy7-Ly6G[1A8] or APC-CD11c[N418] were added for 30-45 min at room temperature. FITC-CD3e[145-2C11], FITC-Ly6G[RB6-8C5], FITC-CD11b[M1/70], FITC-CD45R/B220[RA3-6B2] and FITC-Ly76 [Ter-119] (erythroid lineage marker) were used as lineage markers. Corresponding isotype control antibodies were added to samples at the same concentrations as the antibodies of interest. After incubation, samples were washed three times and analyzed by FACSverse (BD Pharmingen). Compensation was done using positive samples containing single color-stained aortic macrophages. Debris and dead cells, as defined by low forward scatter, were excluded from analysis. Data were analyzed with FlowJo (Tree Star).

Chromatin Immunoprecipitation

ChIP analysis was performed using a Chromatin Immunoprecipitation Kit (Active Motif) according to the manufacturer's instructions. Briefly, bone marrow-derived macrophages were stimulated with or without AngII (10 μM), TNFα (10 ng ml−1) and IL-1β (20ng ml−1) for 3 h prior to crosslinking for 10 min with 1% formaldehyde. Chromatin was sheared by sonication to an average size of 200-1000 base pairs (Covaris). Immunoprecipitation was performed using anti-KLF6 antibody (Santa Cruz Biotechnology) and rabbit IgG antibody (Santa Cruz Biotechnology). PCR amplification of the GM-CSF promoter region spanning KLF-binding elements was performed using the following primers: forward: 5'-AAGC CCTTCCAAGAACTGGC-3' (SEQ ID NO: 4) and reverse 5'-GGCCCCT-CAAAAAGGAGAGG-3' (SEQ ID NO: 5).

KLF6 recruitment was normalized by input DNA and compared to control group with KLF6 antibody.

RNA Isolation and Quantitative Real-Time PCR

Total RNA from cultured cells, aortic macrophages, bone marrow-derived neutrophils or murine aortic samples was extracted using either RNeasy minikit (Qiagen) or RNAlater (Qiagen) according to the manufacturer's instructions. 0.5 µg-1 µg RNA was reverse-transcribed using Superscript III (Invitrogen) according to the manufacturer's instructions. Real-time PCR reactions were performed using 2 µl of resulting cDNA per 20 µl reaction volume containing SYBR green I master (Roche). GAPDH was used as an internal control. Using bone marrow-derived macrophages with AngII (10 µM, 3 h) stimulation, RT2 profiler PCR array (Qiagen) was performed with 84-related genes for the IL-6/STAT inflammatory pathway. PCR was performed on a LightCycler 480 Real-time PCR system (Roche) in accordance with the manufacturer's recommended procedure. Real-time PCR primers are shown in Table 5.

Western Blot Analysis

Mouse aortic specimens were homogenized with lysis buffer (T-PER, Thermo Scientific) containing protease inhibitors complex (Roche) and phosphatase inhibitors (Roche). Protein concentration was assayed using BCA protein assay kit (Pierce), and five micrograms of the protein were resolved by 10% NuPAGE (Invitrogen) then transferred to polyvinylidene difluoride membrane. The blot was probed with primary antibodies; pSmad2 (dilution 1:400), pERK1/2 (1:3,000), pSTAT3 (1:3,000), Smad2 (1:1,000), ERK1/2 (1:3,000) or pSTAT3 (1:3,000) (all rabbit antibodies obtained from Cell Signaling Technology) and anti-GAPDH antibody (Ambion). Membranes were washed and incubated with the corresponding horseradish peroxidase-conjugated secondary antibody (Cell Signaling Technology). Protein bands were detected by ECLplus (Thermo scientific) and GAPDH served as an internal control for protein loading.

Enzyme-Linked Immunosorbent Assay

Plasma levels of IL-6, MCP-1 and GM-CSF in mice or in humans with or without aortic dissection/intramural hematoma were assayed with commercially available quantikine ELISA kits (R&D systems) according to the manufacturer's instructions. Sera of healthy volunteers and of patients with aortic aneurysm, coronary artery disease or with aortic dissection were obtained with informed consent under a protocol approved by the University of Tokyo hospital research ethics committee. Baseline characteristics of human subjects are shown in Table 6.

Statistical Analyses

All data are presented as means±s.e.m. Statistical difference between two groups was determined with Student's t-test (two-tailed) for parametric data or Mann-Whitney test for non-parametric data after testing for normality by F-test analysis. For data containing multiple time points, two group comparisons at the same time point were done. When comparing multiple groups, data were analyzed by the Kruskal-Wallis non-parametric one-way ANOVA with Dunn's post test. Survival curves were created using the Kaplan-Meier method and compared by a log-rank test. Statistical power for mouse experiments was calculated using Biomath (biomath.info/power). All samples sizes were equal to or greater than the recommended minimum group size. All data were analyzed using Prism 6.0 (GraphPad Software). A P value of less than 0.05 was considered significant.

Results

Example 1—Aortic Aneurysm with Inflammation in KLF6 Heterozygous Knockout Mice

Figure 1F:
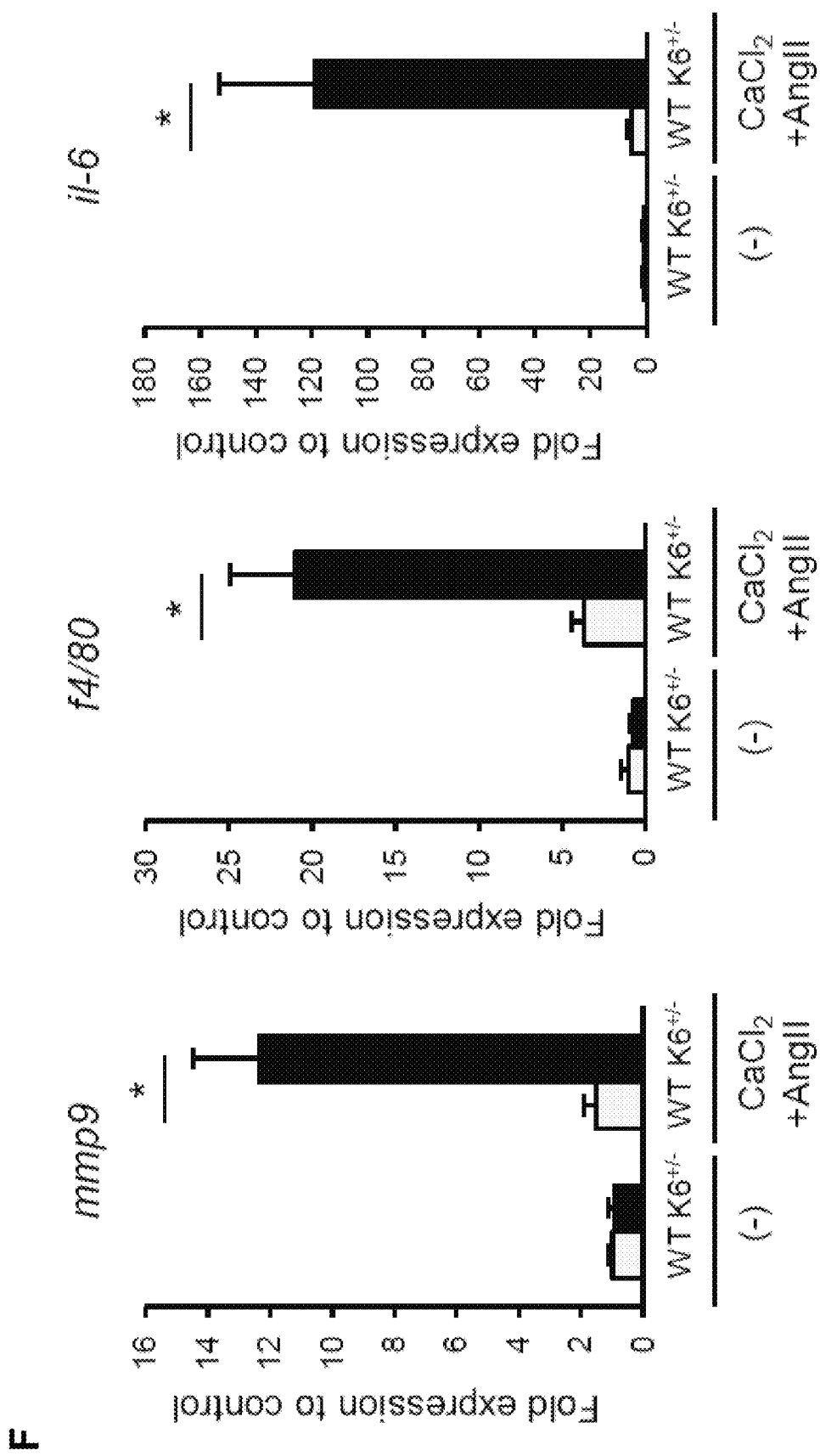

The inventors initially found that mice heterozygously depleted for KLF6 manifest a phenotype of exacerbated aortic aneurysm (defined as greater than 50% increase in external aortic diameter with conserved aortic wall) (21,22) when subjected to aortic inflammation [two weeks-infusion of angiotensin II (AngII) with local application of calcium chloride (CaCl2)]. Histological findings showed enlargement of the aortic lumen with fragile aortic wall and further fibrotic tissue deposition compounded with marked infiltration of macrophages (Mac3-positive cells) (FIG. 1A-E). Mechanistically, increased expression of matrix metalloprotease-9 (MMP9, as a marker of vascular remodeling) (23), F4/80 (as a marker of macrophages) (24,25) and IL-6 (as a marker of inflammation) (16,26-30) were seen in the aorta (FIG. 1F).

Figures 1G, 1H:
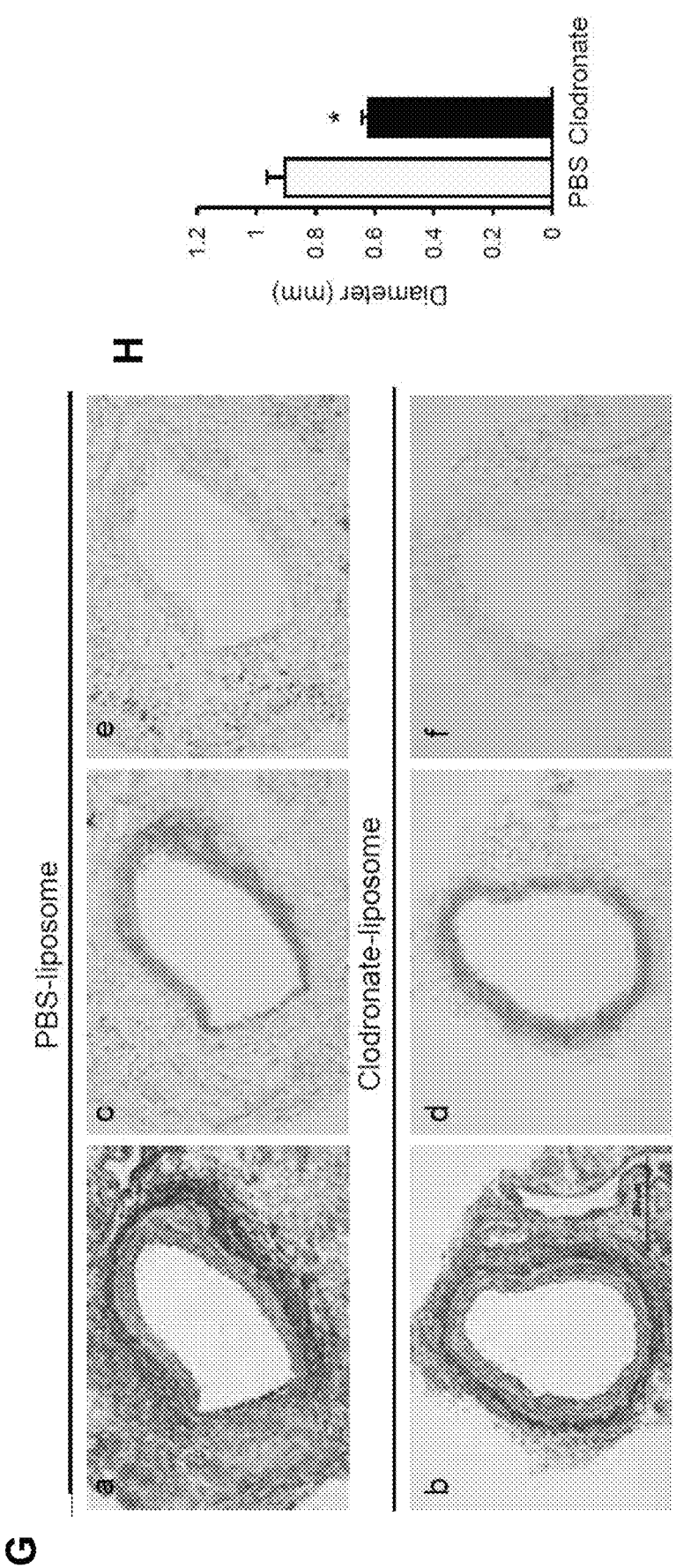

As marked infiltration of immune cells was seen in the diseased aorta of these mice, macrophages were depleted using clodronate, which abrogated the aortic phenotype with near absence of macrophage infiltration (FIG. 1G, H). Thus, immune cells including macrophages were important for aortic remodeling in this model.

Example 2—KLF6fl/fl;LysM Cre Mice Exhibit Aortic Dissection/Hematoma

Figures 2A, 2B:
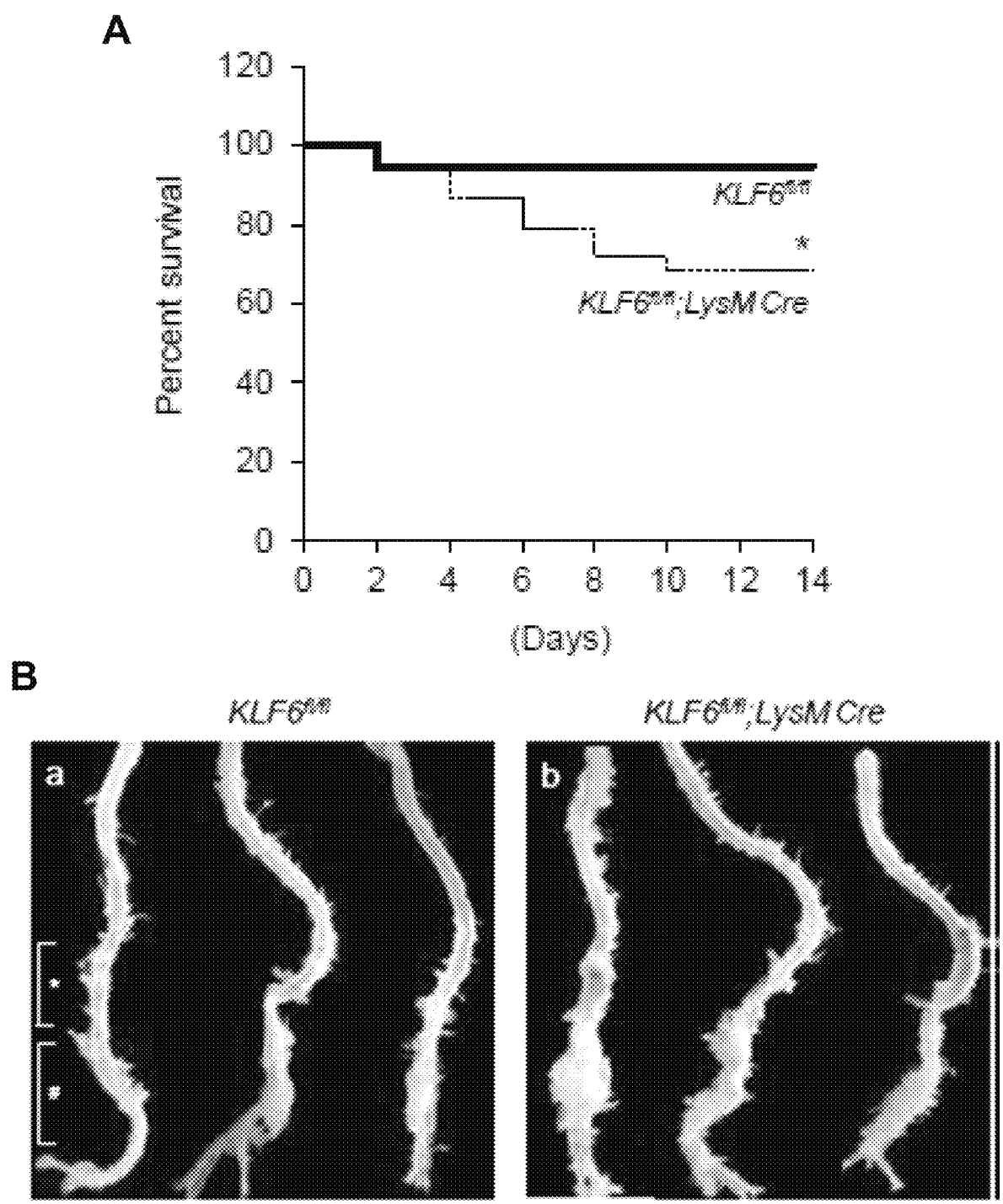
Figures 2C, 2D:
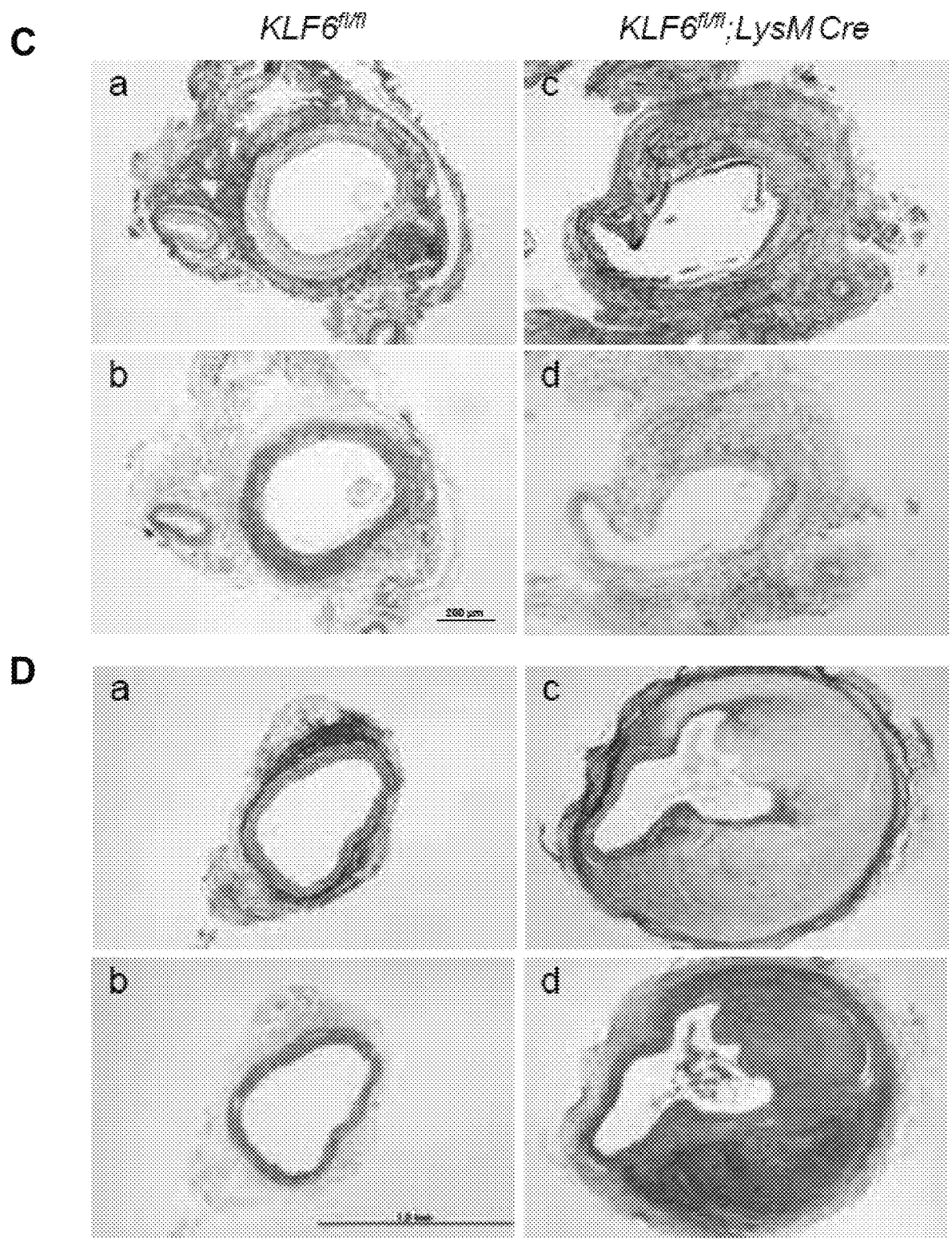

As the aortic condition in KLF6-deficient mice appeared to involve a dysregulated inflammatory response by macrophages, myeloid-specific KLF6-deficient mice (KLF6fl/fl; LysM Cre mice) were further generated which showed specific reduction of KLF6 expression in the myeloid lineage by 70% as compared to control mice. KLF6fl/fl;LysM Cre mice subjected to aortic inflammation showed a similar phenotype of exacerbated abdominal aortic aneurysm to that seen in heterozygous knockout mice, but intriguingly, further showed supra-renal aortic dissection/intramural hematoma as defined as separation of the intra-aortic wall with hematoma formation accompanied by intimal tear for dissection 3 (FIG. 6). This lesion also showed fibrotic tissue deposition with infiltration of Mac3-positive macrophages (FIG. 2B-E and FIG. 7A,B), thus confirming that the aortic phenotype in KLF6-deficiency was associated with perturbation of the inflammatory response. Mice that died were from aortic rupture most likely secondary to aortic dissection/intramural hematoma (FIG. 2A).

Figures 2E, 2F, 2G:
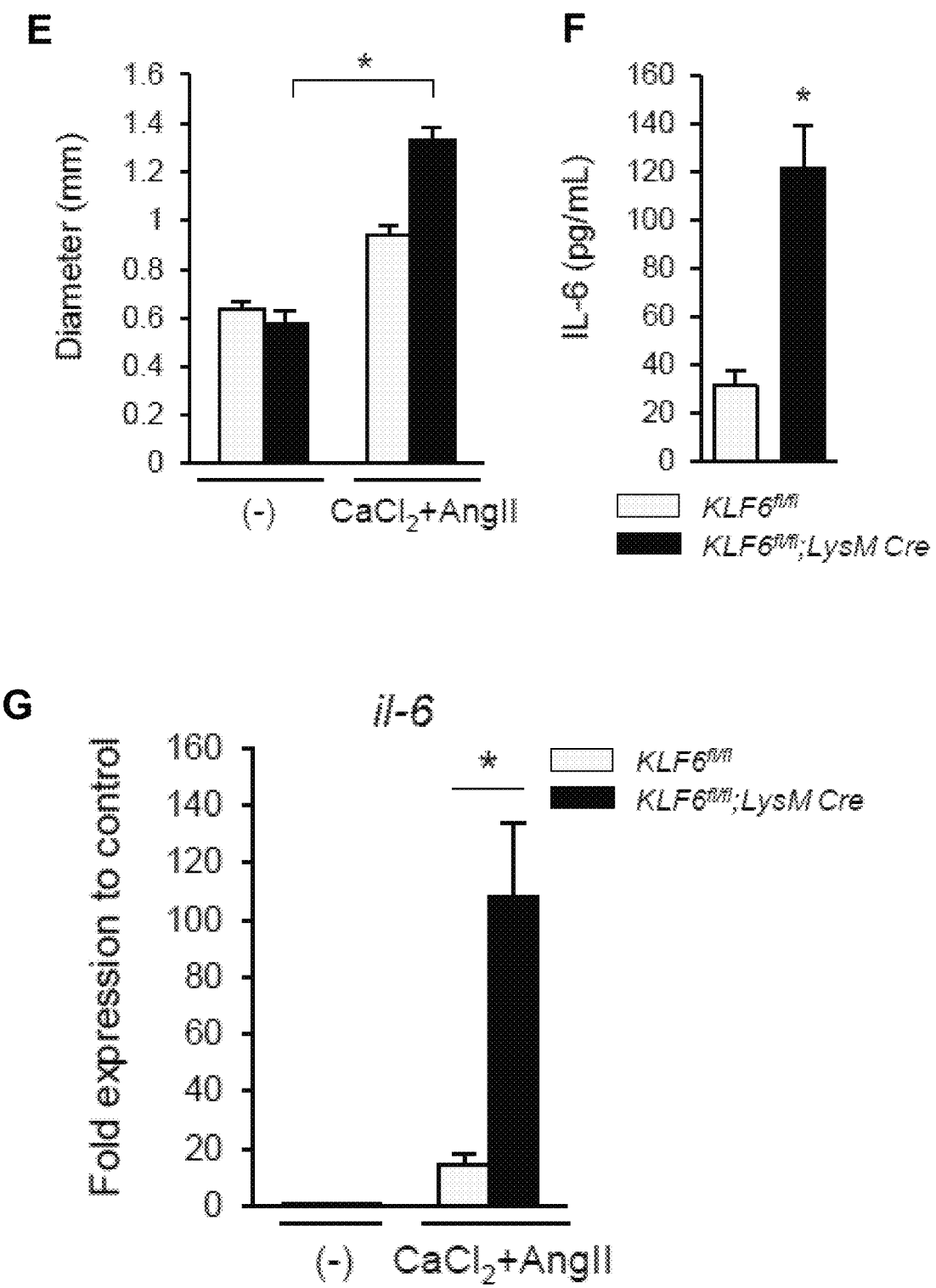
Figure 2H:
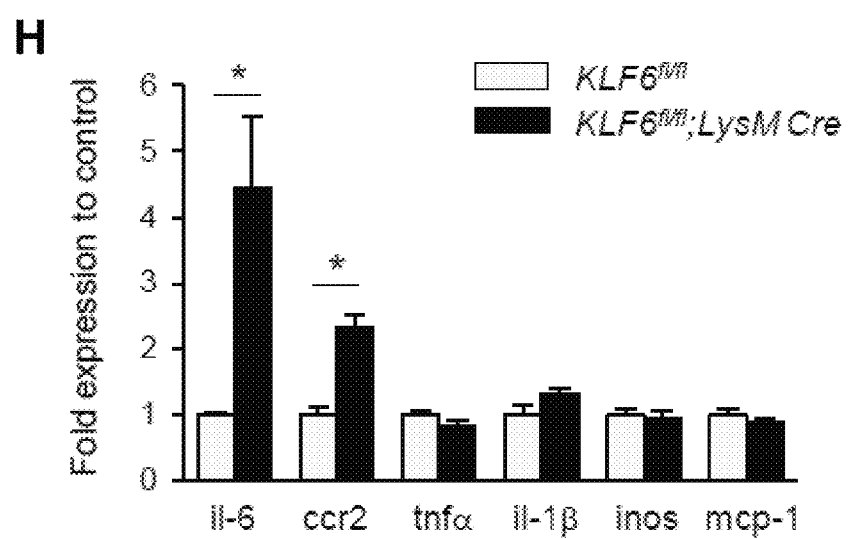
Figure 2I:
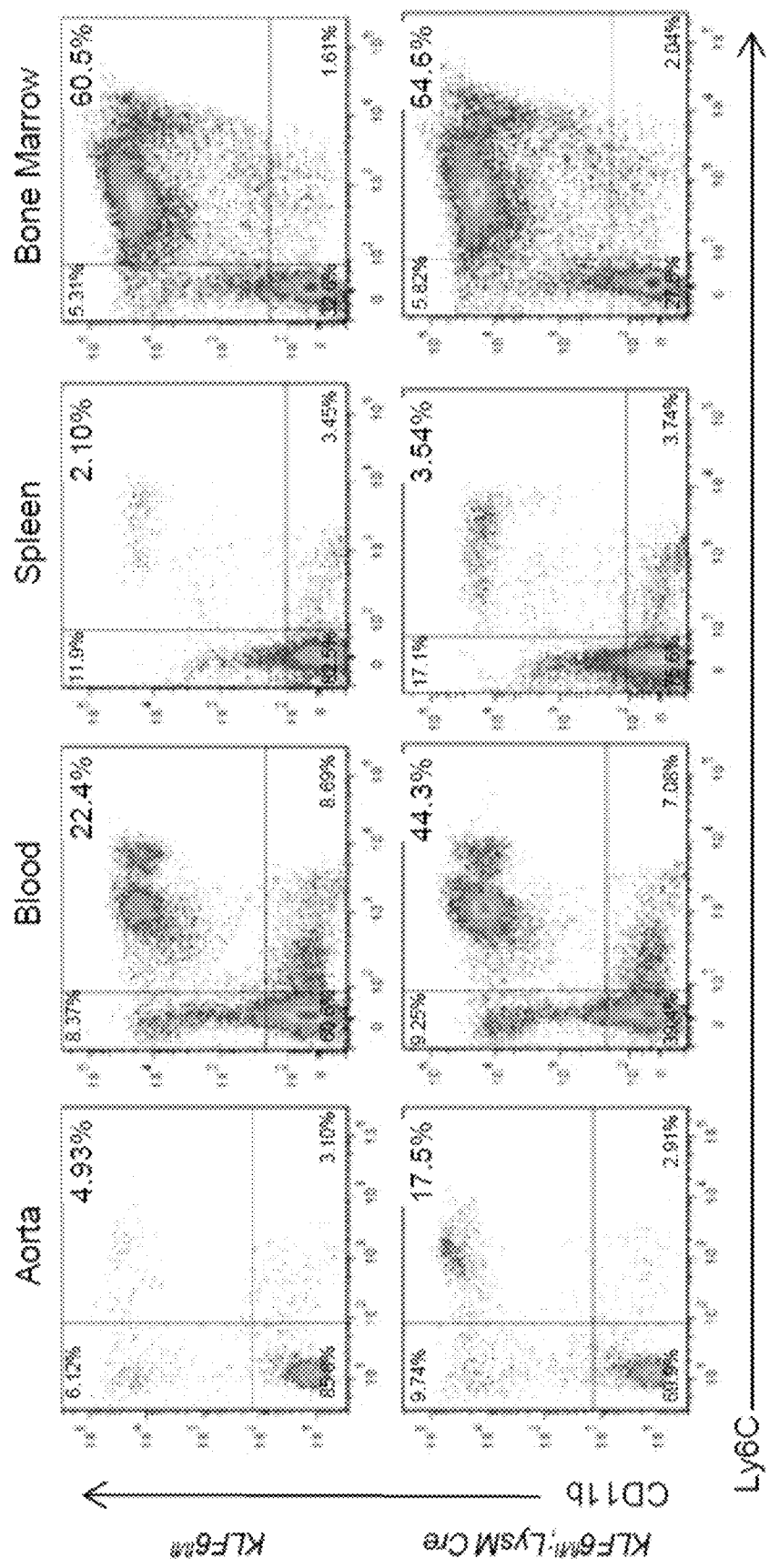
Figure 8A:
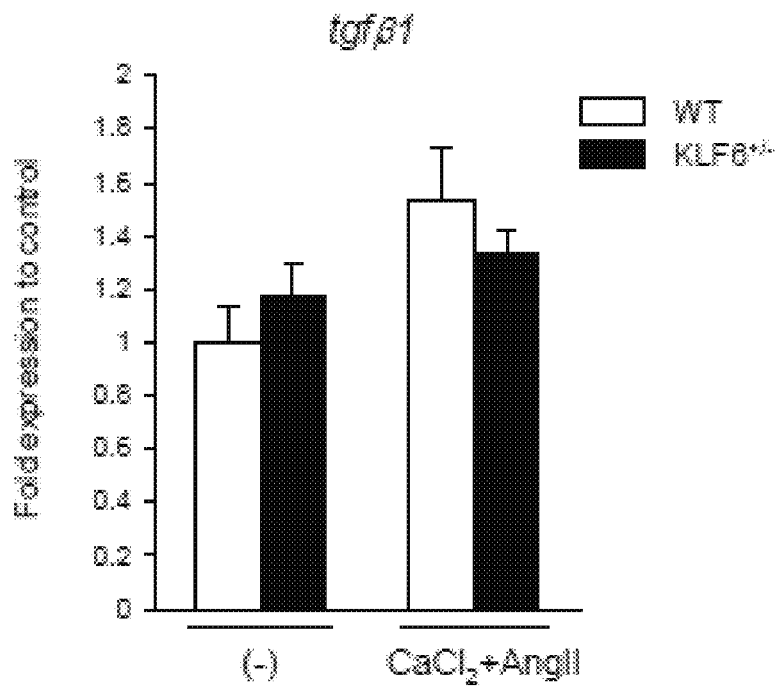
Figure 8B:
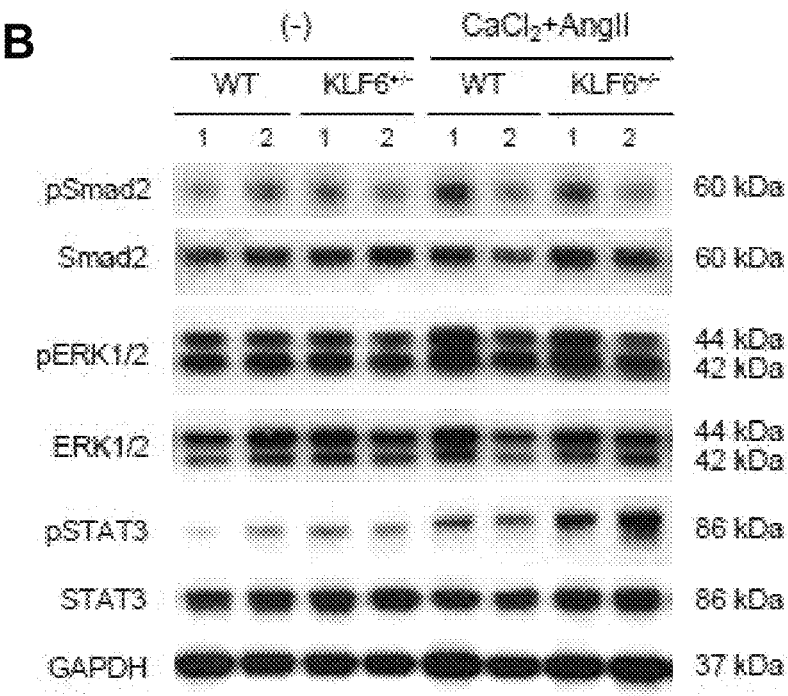
Figure 8C:
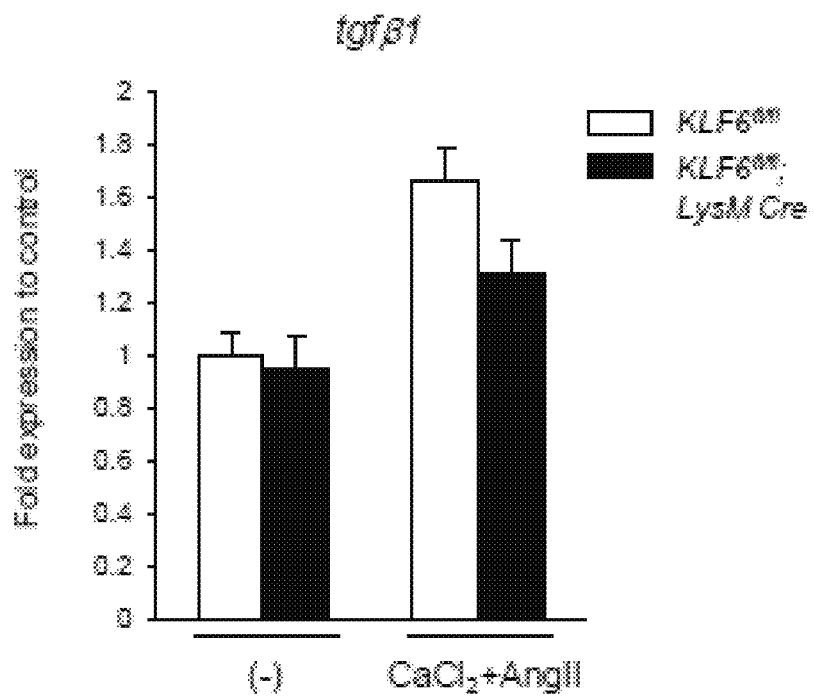
Figure 8D:
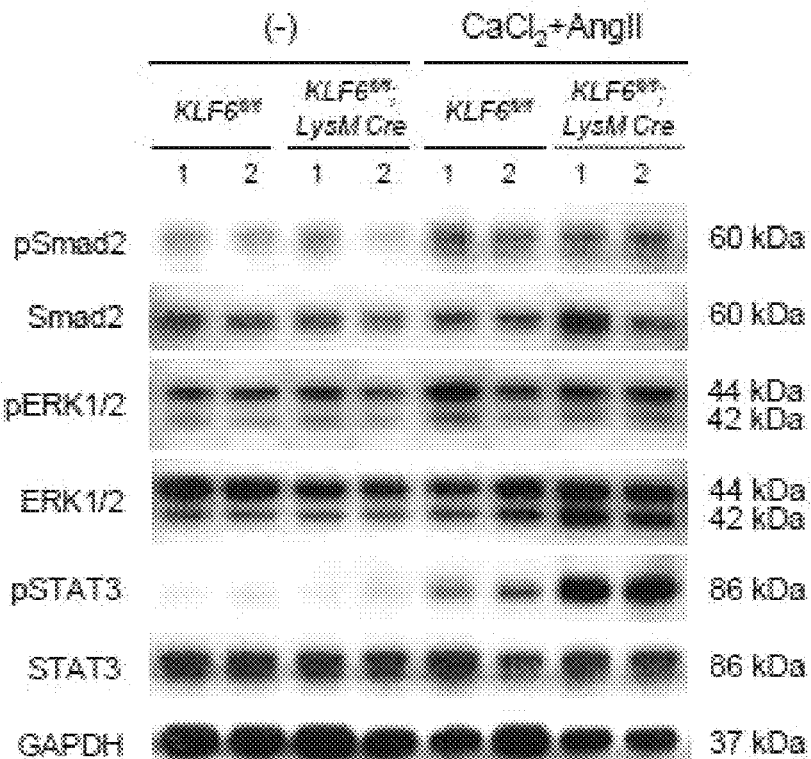
Figure 9A:
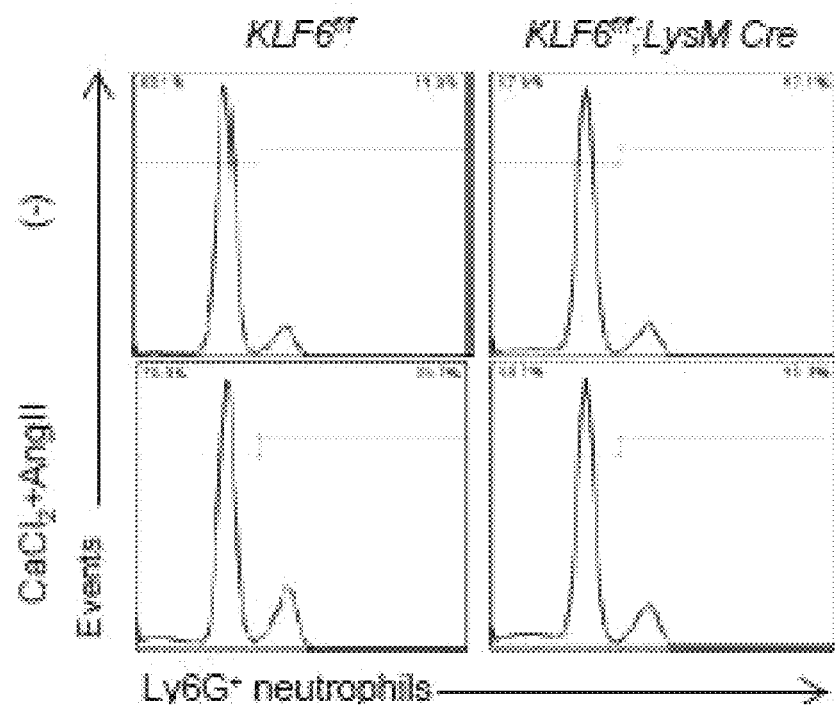
Figure 9B:
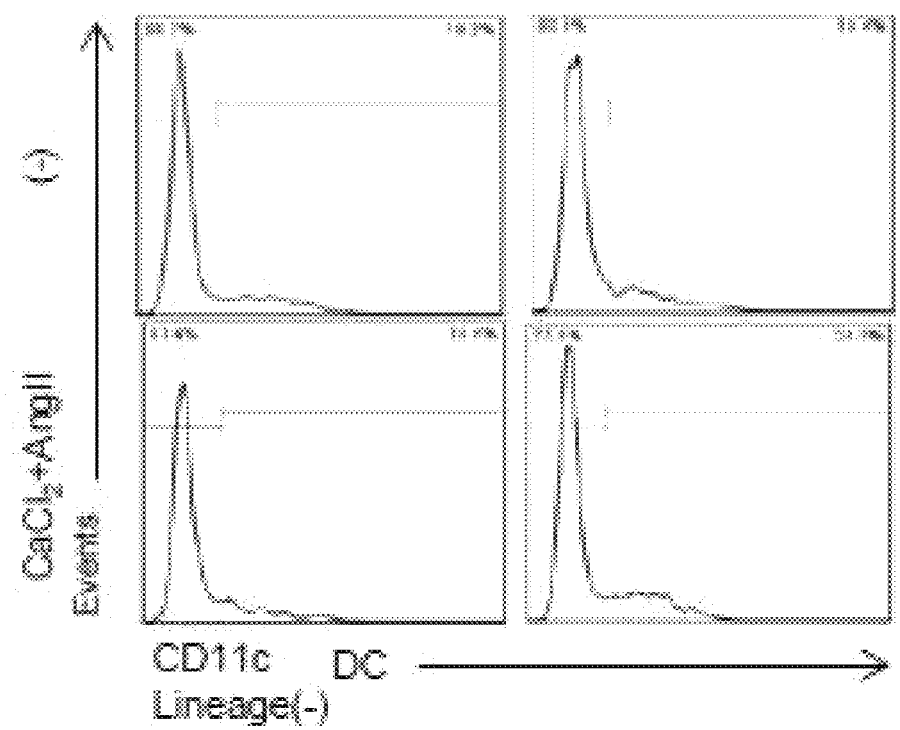
Figures 9C, 9D:
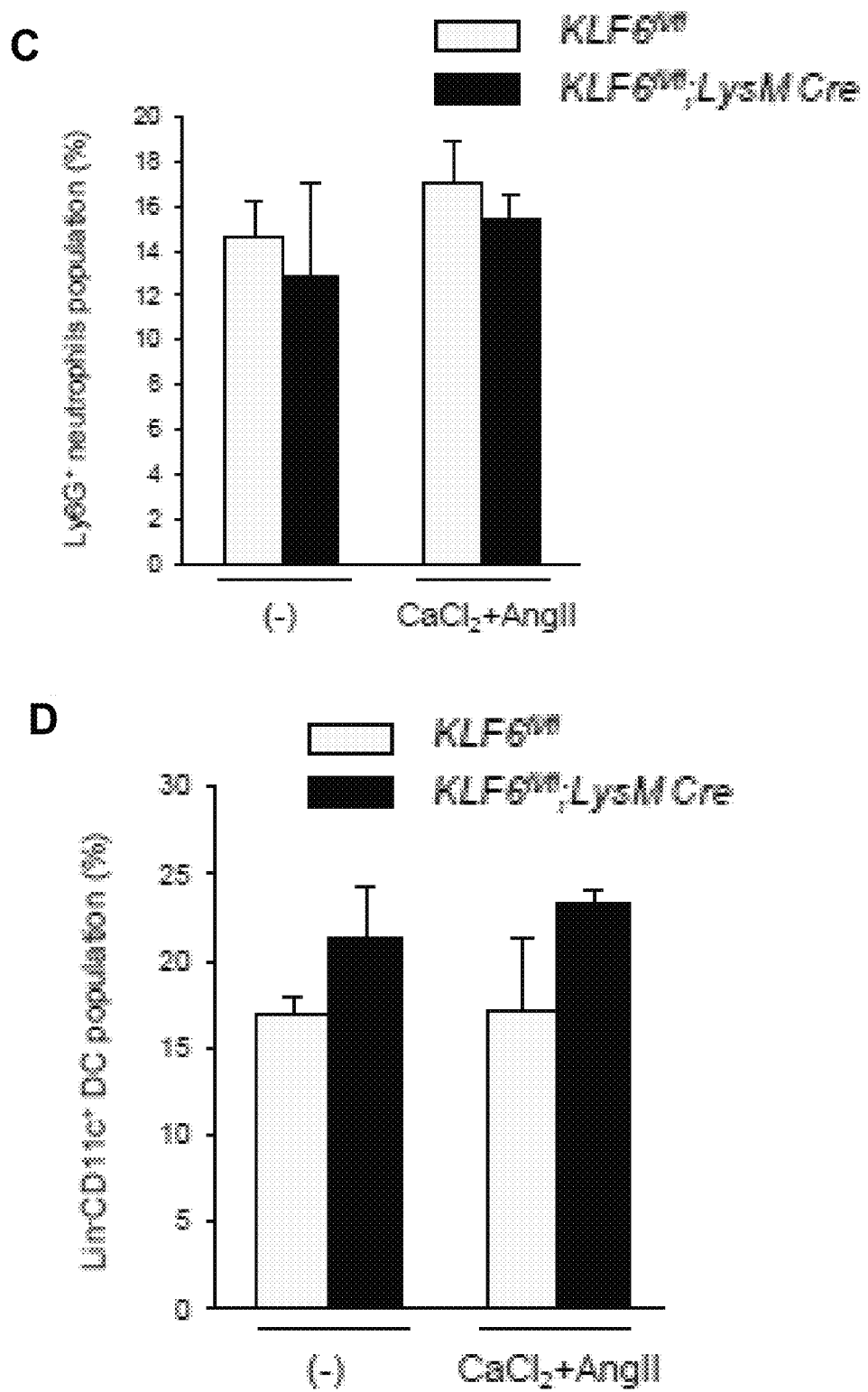
Figure 9E:
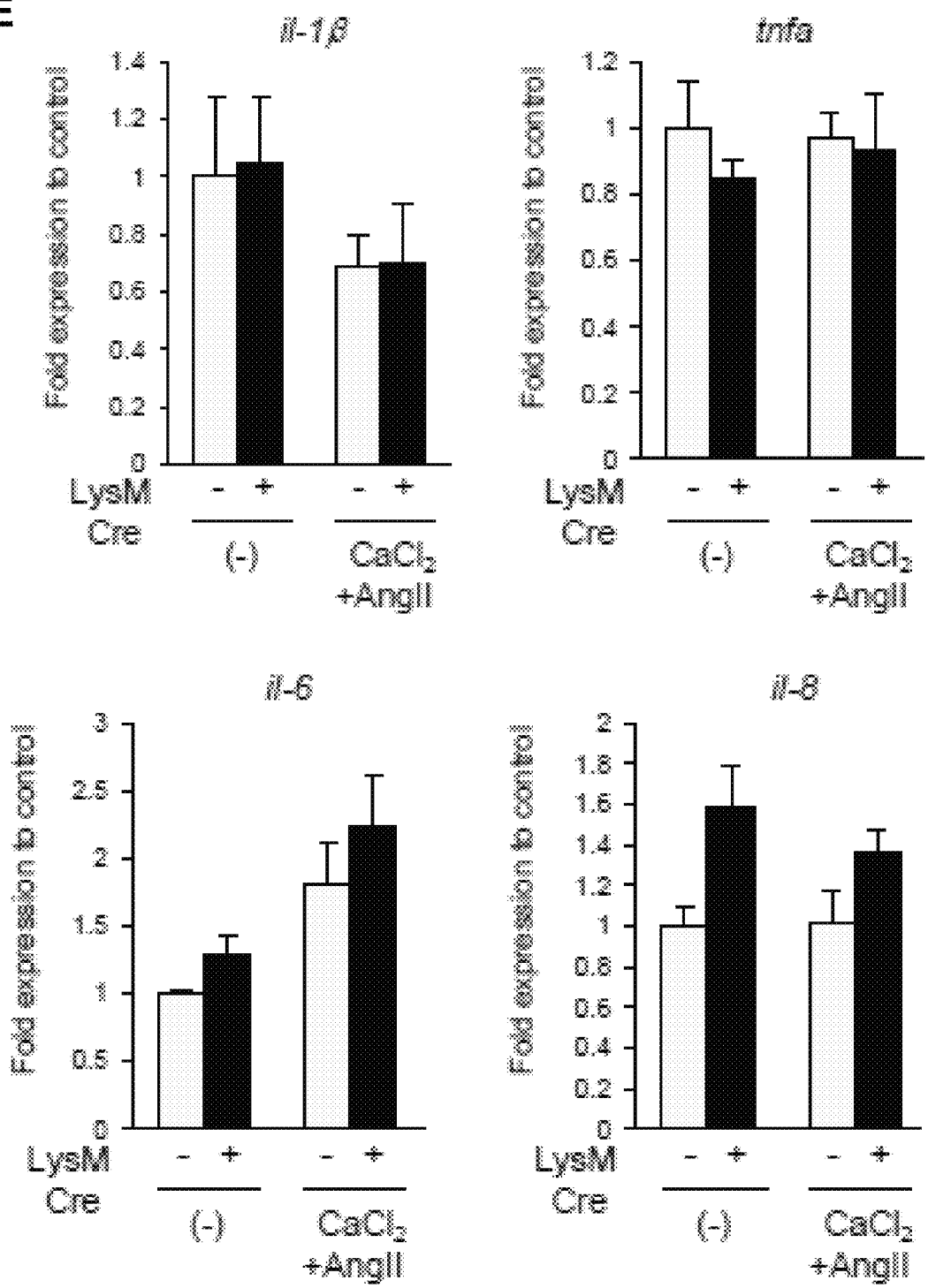

Mechanistically, KLF6fl/fl;LysM Cre mice showed elevated expression of IL-6 in the aortic lesion (FIG. 2G) and elevated circulating levels (FIG. 2F). Further, macrophages obtained from bone marrow of KLF6fl/fl;LysM Cre mice exhibited increased IL-6 expression (FIG. 2H) with activation of IL-6-downstream STAT3 (FIG. 8D). Differences in expression were not seen in other major pro-inflammatory cytokines such as IL-1β, MCP-1 or TNFα between macrophages from KLF6fl/fl and KLF6fl/fl;LysM mice (FIG. 2H). Immune cells in the diseased aorta of these mice were characterized by flow cytometry analysis which showed a markedly increased population of CD11b+Ly6Chi inflammatory monocytes and this increase was also seen in the peripheral blood (FIG. 2I). Granulocytes (e.g. neutrophils; Ly6G+ cells) were not affected in number or (sub-) population under basal conditions or in the setting of CaCl2 and AngII infusion (Table 1 and FIG. 9A,C) nor was the functional activity of neutrophils as examined by inflammatory cytokine expression such as IL-8 or TNFα (FIG. 9E) or that of population of dendritic cells (Lineage-CD11c+ cells) (FIG. 9A, C) affected under these conditions. Taken together, expansion of inflammatory monocytes in the aorta and circulation was selectively associated with the present experimental model and conditions.

TGFβ, a central molecule in the pathogenesis of Marfan aortopathy (12, 14, 32-34), and its downstream signaling pathways (canonical pSmad-235 and non-canonical pERK1/212) were not affected in either KLF6fl/fl;LysM Cre mice or heterozygous knockout mice (FIG. 8A-D), suggesting that the TGFβ-mediated pathway was not critically involved in the underlying phenotype.

Example 3—GM-CSF is a Downstream Target of KLF6

Delineation of target molecules and mechanisms of regulation of immune cells was next addressed using RNA profiling array analysis. Remarkably, GM-CSF levels showed the greatest increase in macrophages derived from bone marrow of KLF6fl/fl;LysM Cre mice in response to AngII stimulation (3.89-fold) as compared to control macrophages (FIG. 3A).

Figure 3C:
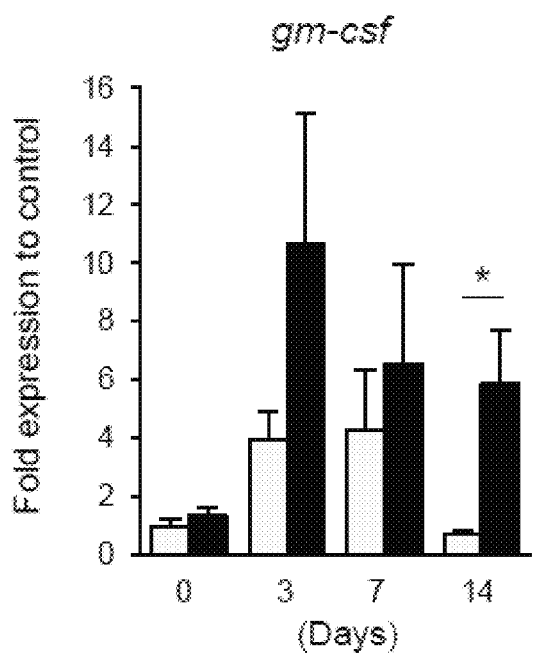
Figure 3D:
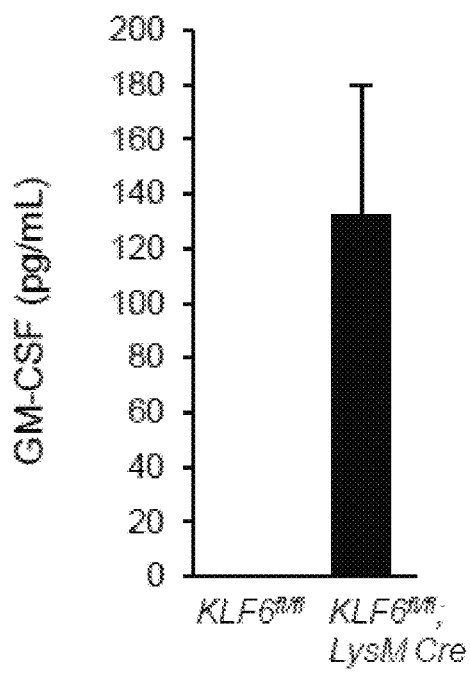
Figure 3E:
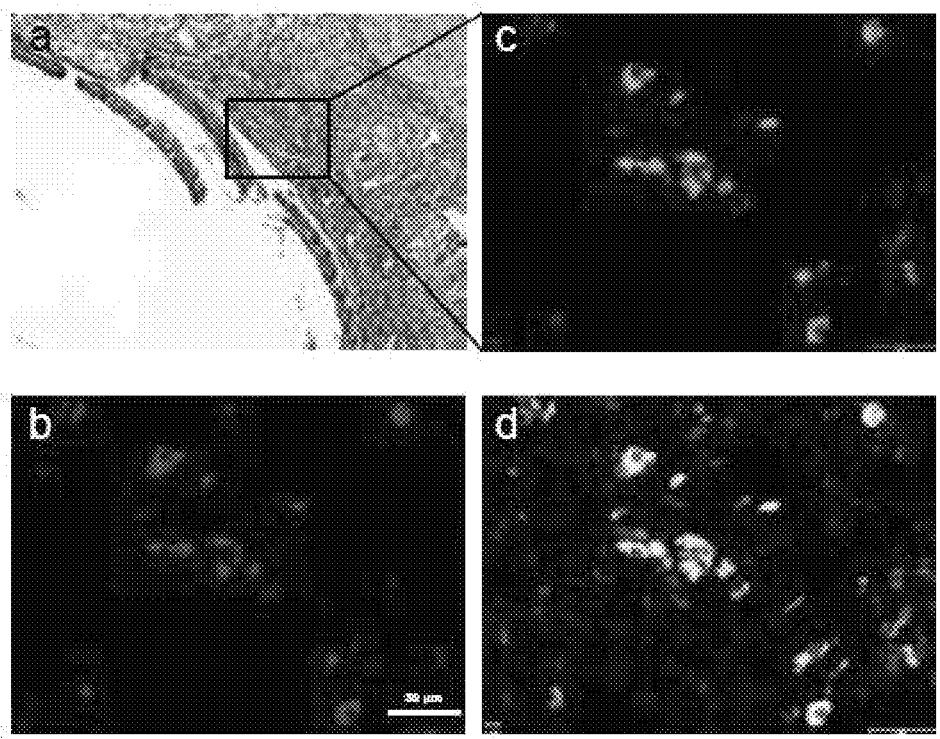
Figures 10A, 10B:
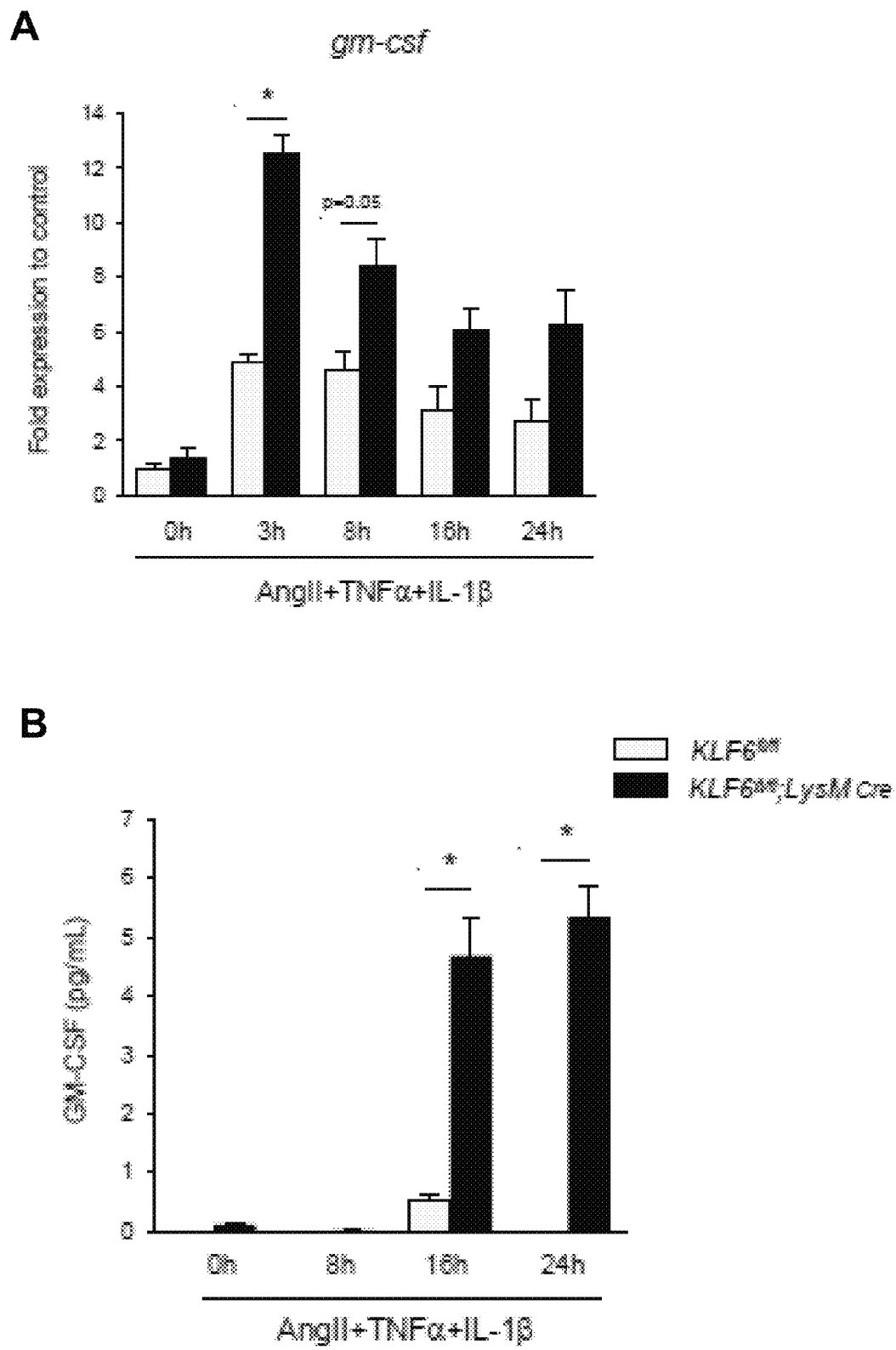

Surprisingly, macrophages obtained from aorta of KLF6fl/fl;LysM Cre mice showed markedly increased expression of GM-CSF under experimental conditions of CaCl2 application and AngII infusion (FIG. 3B), and in macrophages derived from bone marrow of these mice (FIG. 10A). Expression of GM-CSF in the aorta was elevated from three days after treatment (before onset of aortic dissection) of KLF6fl/fl;LysM Cre mice (FIG. 3C). Whether deletion of KLF6 in macrophages affects secretion of GM-CSF and further systemic circulating levels was next studied. Macrophages and GM-CSF co-localized in the aorta of KLF6fl/fl;LysM Cre mice, and GM-CSF was markedly produced by macrophages in response to pro-inflammatory stimuli (FIG. 3D and FIG. 10B). Circulating levels of GM-CSF were at least 73.3-fold higher in KLF6-deleted mice (FIG. 3E). It therefore seems that a markedly increased response in GM-CSF is a surprising hallmark feature of the aorta in KLF6fl/fl;LysM Cre mice.

Figure 10C:
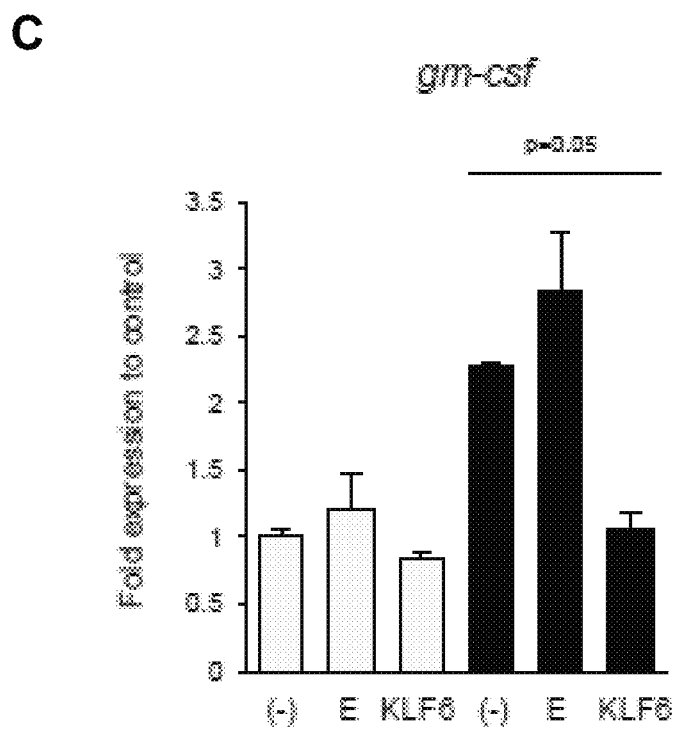
Figure 10D:
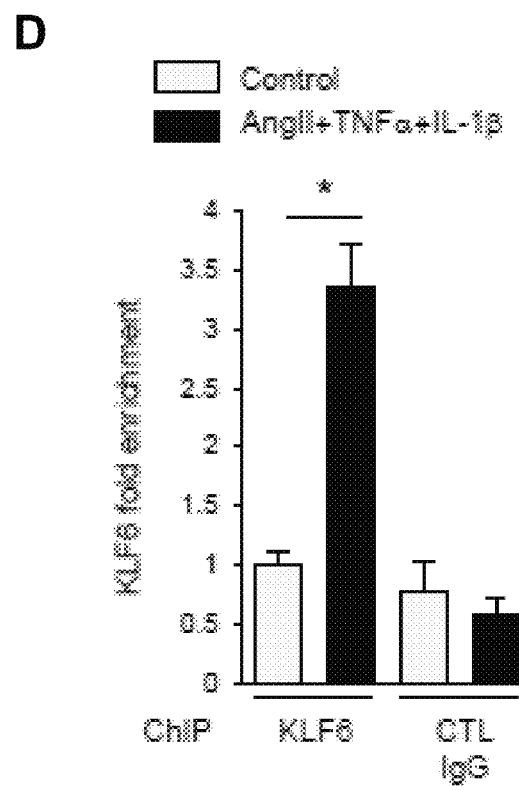

The inventors next sought to understand mechanisms underlying regulation of GM-CSF expression and secretion by KLF6. Over-expression of KLF6 significantly attenuated GM-CSF expression induced by pro-inflammatory stimuli in macrophages (FIG. 10C). Transcriptionally, several KLF-binding sites were present in the promoter region of GM-CSF to which KLF6 was recruited by agonistic stimuli treatment in macrophages (FIG. 10D). These results demonstrated that, mechanistically, GM-CSF is a direct target of KLF6 and that KLF6 represses expression of GM-CSF.

Example 4—GM-CSF Manipulation Regulates Aortic Dissection/Hematoma

Figure 4A:
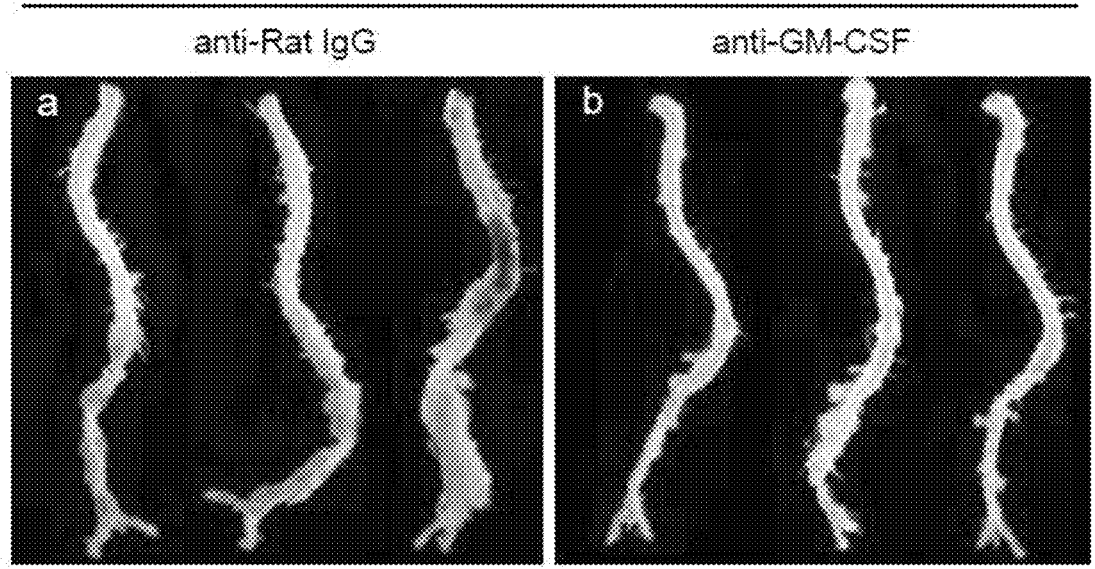
Figure 4B:
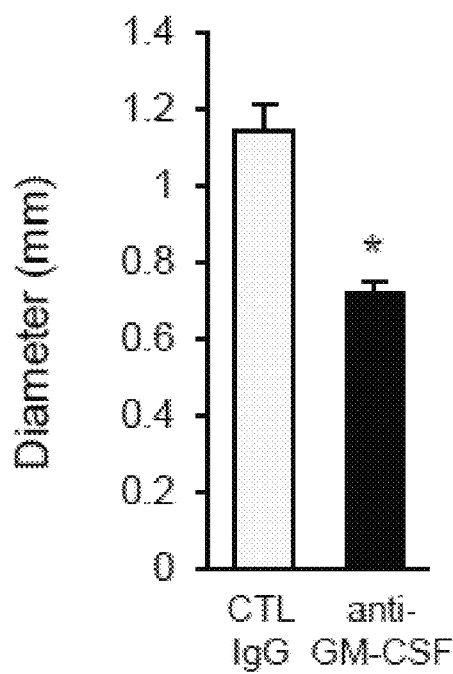
Figure 4C:
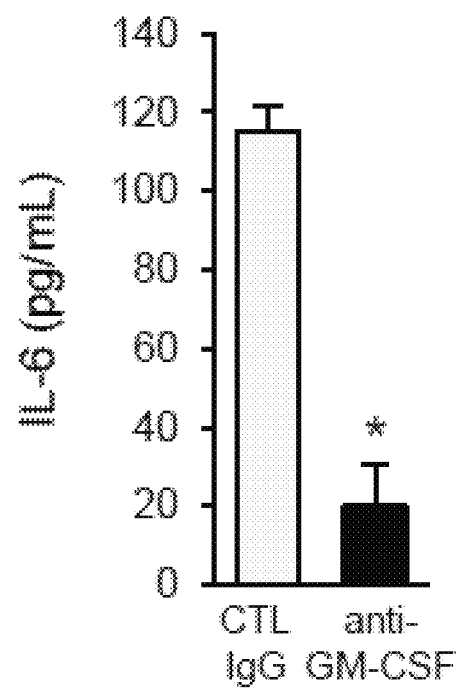
Figure 4D:
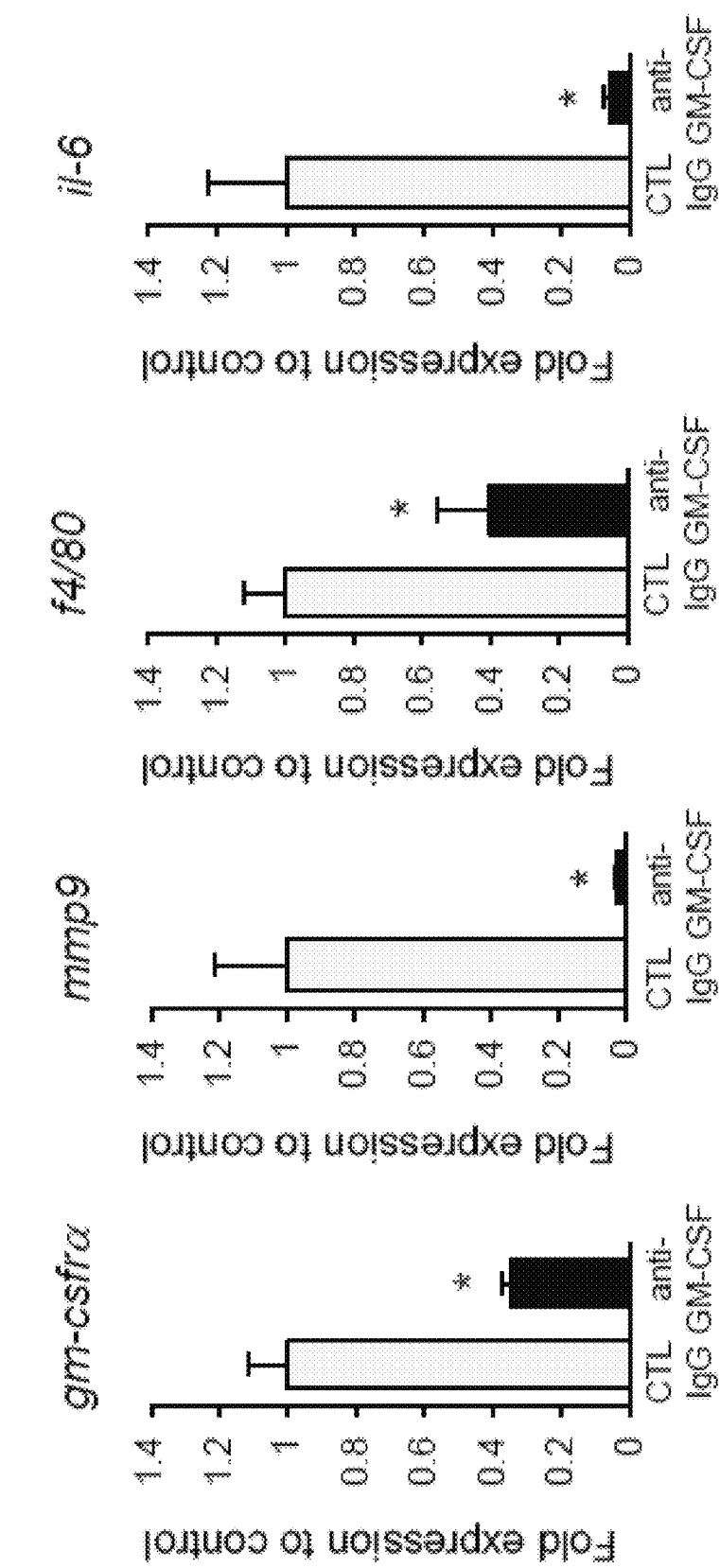
Figure 4E:
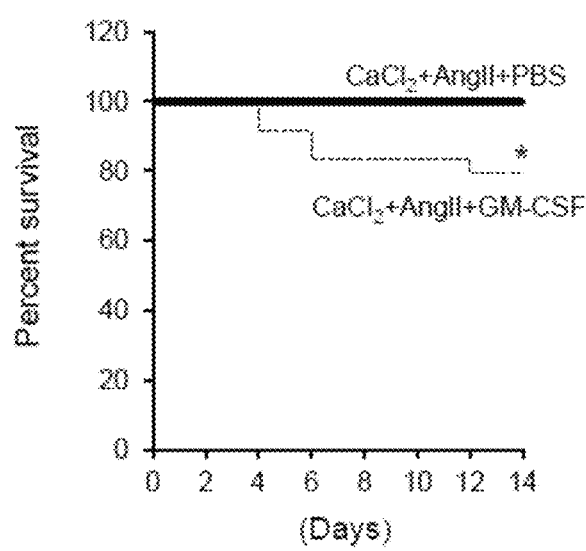
Figure 4F:
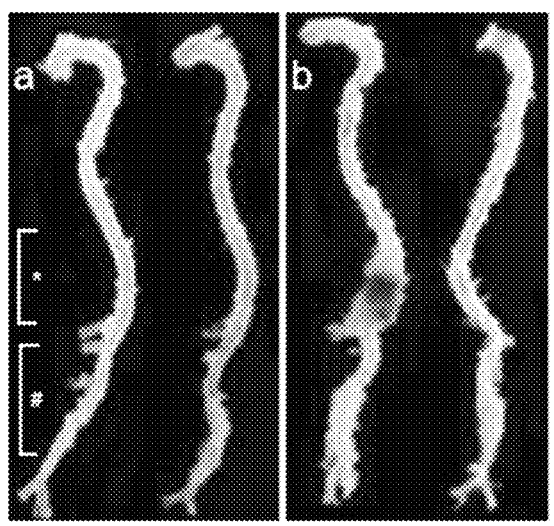
Figure 4G:
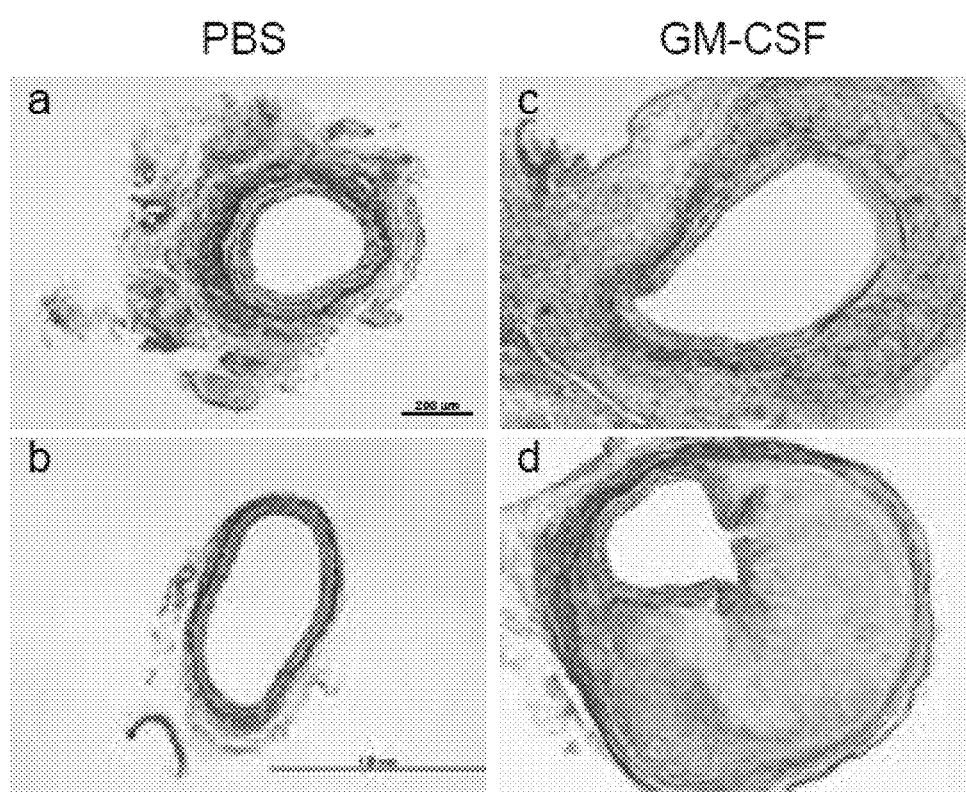

To next test the requirement of GM-CSF in aortic dissection in these mice, the actions of GM-CSF were blocked using a neutralizing antibody which abrogated aortic dissection/intramural hematoma (FIG. 4A, B), as well as expression of GM-CSF receptor α, MMP9, F4/80 and IL-6 (FIG. 4D) in addition to serum levels of IL-6 (FIG. 4C). GM-CSF was therefore required for the aortic phenotype in KLF6fl/fl;LysM Cre mice.

Figures 4H, 4I, 4J:
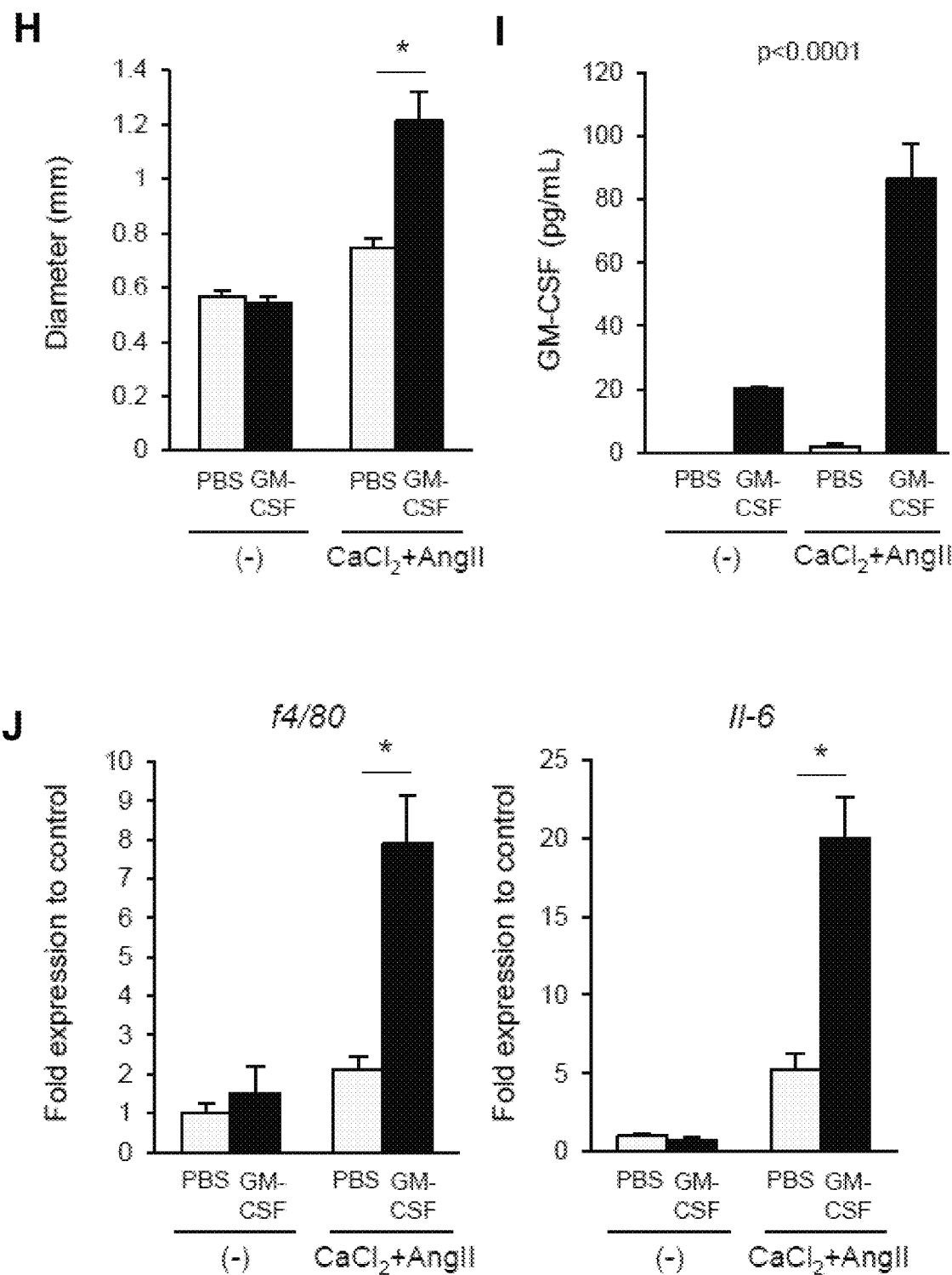

The inventors further investigated whether GM-CSF is sufficient to induce the aortopathy. Administration of GM-CSF in wild-type mice subjected to aortic inflammation (CaCl2+AngII) caused aortic dissection/intramural hematoma confirming the generality of the role of GM-CSF in the pathogenesis of the condition. Mice died from aortic rupture due to the aortic lesion and showed pathological features of the condition (e.g. fragile aorta, intimal tear with hematoma) (FIG. 4E-H). However, aortic dissection/intramural hematoma did not develop by administration of GM-CSF alone, even with abnormally increased circulating levels (at least 180.9 fold) of GM-CSF (FIG. 11A, B). As AngII, CaCl2 or GM-CSF alone was not sufficient to induce the condition, it seems that combination of aortic inflammation with GM-CSF infusion is necessary for the phenotype (FIG. 12A, B). Consistent with this, circulating levels of GM-CSF in mice were only markedly elevated when treated with combination of measures as compared to each alone (FIG. 4I). Note that these elevated levels were comparable to those in KLF6fl/fl;LysM Cre mice suggesting that highly elevated levels of GM-CSF are required but not sufficient to cause aortic dissection/intramural hematoma (FIG. 3E).

Finally, whether manipulation of GM-CSF affects the number of peripheral leukocytes was examined. With GM-CSF administration, the number of circulating lymphocytes did not change in either the early phase (5 days) or developed phase (14 days) of the model (Tables 2 and 3). With respect to neutrophils, the number in peripheral blood was markedly increased in the early phase but no difference was observed at 14 days of GM-CSF administration. This was similarly seen in the group in which GM-CSF alone was administered which did not result in the aortic phenotype. While these changes might be due to acute effects by exogenous GM-CSF treatment, this alone had no bearing on the phenotype. Moreover, the number of circulating granulocytes and lymphocytes was not affected when GM-CSF was depleted by neutralizing antibody (Table 4). Based on these results, manipulation of GM-CSF did not affect the number of circulating leukocytes in the present model, at least during the observation period (14 days).

Example 5—Up-Regulation of GM-CSF in Patients with Aortic Dissection

To confirm the clinical relevance of these findings, circulating levels of GM-CSF were measured in sera of patients with acute aortic dissection which showed marked increases in contrast to patients with coronary artery disease, aortic aneurysm or healthy volunteers which showed markedly lower if not negligible levels (FIG. 5A). Furthermore, inflammatory infiltration (CD68+ monocytes/macrophage) and GM-CSF expression were up-regulated and co-localized in dissected aorta (FIG. 5B). Thus, GM-CSF is associated with aortic acute dissection not only in mice but also in human conditions.

Discussion

The present findings show that GM-CSF is a key regulatory molecule causative of aortic dissection/intramural hematoma in a murine model of the condition and to also be associated with the condition in humans. In mice, modulation of GM-CSF by a neutralizing antibody or exogenous administration respectively prevented or induced onset of this phenotype. In humans, elevated serum GM-CSF levels and expression of the cytokine in aortic tissue were seen in patients with aortic dissection.

GM-CSF was a central component of the aortic dissection/intramural hematoma phenotype in the inventors' murine model. Previous studies had suggested a limited role of GM-CSF in the pathogenesis of aortic disease (36-39). For example, mice that lack smad3 manifested a phenotype of aortic aneurysm formation (39) and GM-CSF was shown to play a pivotal role in the pathogenesis; however, it was assumed that because smad3 is a downstream target of TGFβ which is a central molecule associated in Marfan aortopathy, that the pathogenic mechanism was limited to this genetic aortopathy. The findings show that activation of the GM-CSF pathway in a manner independent of the TGFβ-SMAD pathway is sufficient to trigger this condition in a model of inflammation and degenerative aorta (calcium chloride treatment causes stiffening of the aorta to mimic the condition as seen in atherosclerotic human aortas (40)) as reflective of aortic dissection/intramural hematoma seen in the elderly adult in humans and should be differentiated from the genetic aortopathy in young patients with Marfan syndrome. GM-CSF tissue expression had also been shown to be increased in a patient presenting with aortic dissection in Cogan's disease (41), an apparently auto-immune condition which is characterized by recurrent corneal inflammation (42) that was thought to be an isolated finding.

Effects on other non-macrophage myeloid cells were investigated which showed that dendritic cells (CD11c+ MHCII+ cells) were increased in the diseased aorta but not in the circulation under KLF6-deficient conditions, and lack of effects on neutrophils (Ly6G+ cells) either in the circulation or in the aortic tissue (FIG. 9 and FIG. 8).

Macrophage colony-stimulating factor (M-CSF) has been also suggested to be an important regulator of vascular remodelling (43,44). Although the precise molecular mechanisms of the actions of M-CSF are still unclear, different actions as compared to GM-CSF are envisioned given different expression patterns in the vascular wall. Whereas M-CSF is constitutively expressed under physiological conditions in endothelial cells, fibroblasts, macrophages and smooth muscle cells, GM-CSF, by contrast, is expressed only in minute amounts in these cells under basal conditions but instead is induced by inflammatory stimuli (e.g. TNF) (45) or oxidized-low density lipoprotein (LDL) cholesterol stimulation (46). In murine and human lesions, M-CSF is detected both in healthy arteries and in atherosclerotic lesions associated with macrophage and foam cell content, and is correlated with plaque progression in the latter. By contrast, only minute levels of GM-CSF are seen in smooth muscle cells and endothelial cells of healthy human arteries but are elevated upon atherosclerotic development and macrophage accumulation (47). Based on these observations, collectively, while M-CSF is a constitutively expressed cytokine in the vasculature, GM-CSF is markedly induced in diseased vessels to regulate pathological conditions including the described aortopathy.

On the experimental model, most previous studies have used AngII infusion alone as an intervention to induce a dissection phenotype (16,48). However, the limitation of this procedure for mechanistic investigations including on inflammation was the low reproducibility (less than 30%), need for long-term infusion of AngII (more than 4 weeks) and incidence/expression of phenotype only in aged mice (over 7 to 10 months age) with specific genetic background (ApoE−/− or LDLR−/− mice). Most noteworthy is that the present model could induce aortic dissection/intramural hematoma within 2 weeks with high reproducibility (at least 70%) even in young wild-type mice.

Mechanistically, this model might involve hemodynamic stress on the supra-renal dissection site due to loss of Windkessel effect (49) because of increased stiffening in the infra-renal aorta (e.g. downward shift of pressure-diameter curve after CaCl2 application with continuous AngII infusion) (40) that showed aneurysmal formation which when exposed to inflammatory effects of GM-CSF triggered dissection/intramural hematoma formation in the weak and fragile supra-renal aorta. As aortic aneurysm is commonly co-present in patients with dissection (4), the described animal model and findings closely resemble the condition seen in patients.

Taken together, the findings described herein suggest that GM-CSF is a central regulator of aortic dissection/intramural hematoma in the atherosclerotic and inflammatory aorta which is typically seen in the elderly patient with this condition, and may serve as a potential target for diagnostic and therapeutic exploitation (e.g. aortic stabilization using GM-CSF antagonists) as well as a diagnostic biomarker.

SUMMARY

Aortic dissection and intramural hematoma comprise an aortopathy involving separation of the aortic wall. Underlying mechanisms of the condition remain unclear. Here, the inventors show that granulocyte macrophage colony-stimulating factor (GM-CSF) is a triggering molecule for this condition. Transcription factor Krüppel-like factor 6 (KLF6)-myeloid-specific conditional deficient mice exhibited this aortic phenotype when subjected to aortic inflammation. Mechanistically, KLF6 down-regulated expression and secretion of GM-CSF. Administration of a neutralizing antibody against GM-CSF prevented the condition in these mice. Conversely, administration of GM-CSF in combination with aortic inflammation to wild-type mice was sufficient to induce the phenotype suggesting the general nature of effects. Moreover, patients with this condition showed highly increased circulating levels of GM-CSF, which was also locally expressed in the dissected aorta. GM-CSF is therefore a key regulatory molecule causative of this aortopathy, and modulation of this cytokine is an exploitable treatment strategy for the condition.

TABLE 1

Effect of number of leukocytes in peripheral blood (14 days).

| #/mL | KLF6$^{fl/fl}$ mice | | KLF6$^{fl/fl}$;LysM Cre mice | | |
|---|---|---|---|---|---|
| | Sham (n = 3) | CaCl$_2$ + AngII (n = 3) | Sham (n = 3) | CaCl$_2$ + AngII (n = 3) | P value |
| Lymphocytes | 3452.3 ± 792.9 | 1730.0 ± 92.7 | 3830.0 ± 107.1 | 2288.7 ± 996.7 | 0.414 |
| Neutrophils | 1867.0 ± 351.4 | 2253.3 ± 606.8 | 1340.0 ± 238.0 | 1308.3 ± 639.6 | 0.546 |
| Monocytes | 28.3 ± 13.0 | 96.7 ± 9.8 | 20.0 ± 9.4 | 1610 ± 81.5 | 0.002 |

Data are expressed as mean ± s.e.m.

TABLE 2

Effect of GM-CSF administration on number leukocytes in peripheral blood (5 days).

| | Wild type mice | | | | |
|---|---|---|---|---|---|
| | Sham | | CaCl$_2$ + AngII | | |
| #/mL | PBS (n = 3) | GM-CSF (n = 3) | PBS (n = 3) | GM-CSF (n = 3) | P value |
| Lymphocytes | 3586.7 ± 149.3 | 3150.0 ± 234.5 | 1646.7 ± 426.7 | 1803.3 ± 124.0 | 0.003 |
| Neutrophils | 999.3 ± 186.1 | 2536.7 ± 454.3 | 980.0 ± 192.2 | 1686.7 ± 147.0 | 0.007 |
| Monocytes | 100.0 ± 26.2 | 353.3 ± 103.4 | 290.0 ± 70.4 | 386.7 ± 112.5 | 0.063 |

Data are expressed as mean ± s.e.m.

TABLE 3

Effect of GM-CSF administration on number leukocytes in peripheral blood (14 days).

| | Wild type mice | | | | |
|---|---|---|---|---|---|
| | Sham | | CaCl$_2$ + AngII | | |
| #/mL | PBS (n = 3) | GM-CSF (n = 3) | PBS (n = 3) | GM-CSF (n = 3) | P value |
| Lymphocytes | 2784.2 ± 128.6 | 3052.0 ± 420.3 | 2255.0 ± 227.7 | 1667.2 ± 371.3 | 0.846 |
| Neutrophils | 777.8 ± 118.7 | 976.2 ± 116.7 | 866.2 ± 75.0 | 1052.2 ± 259.2 | 0.523 |
| Monocytes | 139.6 ± 19.2 | 295.3 ± 66.2 | 294.6 ± 7.4 | 310.0 ± 45.9 | 0.018 |

Data are expressed as mean ± s.e.m.

TABLE 4

Effect of GM-CSF blockade by neutralizing antibody on number leukocytes in peripheral blood.

| | KLF6$^{fl/fl}$;LysM Cre mice | | | | |
|---|---|---|---|---|---|
| | Sham | | CaCl$_2$ + AngII | | |
| #/mL | anti-CTL IgG (n = 3) | anti-GM-CSF (n = 3) | nti-CTL IgG (n = 3) | GM-CSF (n = 3) | P value |
| Lymphocytes | 3830.0 ± 107.1 | 2138.7 ± 384.4 | 2286.7 ± 996.7 | 1843.3 ± 311.1 | 0.225 |
| Neutrophils | 1340.0 ± 238.0 | 2849.3 ± 437.2 | 1308.3 ± 639.6 | 785.5 ± 117.5 | 0.069 |
| Monocytes | 20.2 ± 9.4 | 48.0 ± 11.7 | 361.0 ± 81.5 | 82.5 ± 12.5 | 0.001 |

Data are expressed as mean ± s.e.m.

TABLE 5

| The primers for real-time PCR. | | | |
|---|---|---|---|
| Primer | | Sequence (5' to 3') | |
| IL-6 | forward | AGTTGCCTTCTTGGGACTGA | SEQ ID NO: 6 |
| | reverse | TCCACGATTTCCCAGAGAAC | SEQ ID NO: 7 |
| F4/80 | forward | TTGGCCAAGATTCTCTTCCT | SEQ ID NO: 8 |
| | reverse | TCACTGCCTCCACTAGCATC | SEQ ID NO: 9 |
| MMP9 | forward | ATCTCTTCTAGAGACTGGGAAGGAG | SEQ ID NO: 10 |
| | reverse | AATAAAAGGTCAGAATCCACCCTAC | SEQ ID NO: 11 |
| CCR2 | forward | AGAGAGCTGCAGCAAAAAGG | SEQ ID NO: 12 |
| | reverse | GGAAAGAGGCAGTTGCAAAG | SEQ ID NO: 13 |
| TNFα | forward | CATCTTCTCAAAATTCGAGTGACAA | SEQ ID NO: 14 |
| | reverse | TGGGAGTAGACAAGGTACAACCC | SEQ ID NO: 15 |

TABLE 5-continued

The primers for real-time PCR.

| Primer | | Sequence (5' to 3') | |
|---|---|---|---|
| IL-1β | forward | CAACCAACAAGTGATATTCTCCATG | SEQ ID NO: 16 |
| | reverse | GATCCACACTCTCCAGCTGCA | SEQ ID NO: 17 |
| INO5 | forward | ACCTTGTTCAGCTACGCCTT | SEQ ID NO: 18 |
| | reverse | CATTCCCAAATGTGCTTGTC | SEQ ID NO: 19 |
| MCP-1 | forward | GGCTGGAGAGCTACAAGAGG | SEQ ID NO: 20 |
| | reverse | ATGTCTGGACCCATTCCTTC | SEQ ID NO: 21 |
| GM-CSF | forward | GGCCTTGGAAGCATGTAGAG | SEQ ID NO: 22 |
| | reverse | GGGGGCAGTATGTCTGGTAG | SEQ ID NO: 23 |
| GM-CSFRα | forward | CACCGCGTCCTGTAACTCTT | SEQ ID NO: 2 |
| | reverse | GCACCTTGACCTTGTGACCT | SEQ ID NO: 25 |
| TGFβ1 | forward | TGGCGTTACCTTGGTAACC | SEQ ID NO: 26 |
| | reverse | GGTGTTGAGCCCTTTCCAG | SEQ ID NO: 27 |
| IL-8 | forward | CATCTTCGTCCGTCCCTGTG | SEQ ID NO: 28 |
| | reverse | CTGCTATCACTTCCTTTCTGTTGC | SEQ ID NO: 29 |
| GAPDH | forward | AACTTTGGCATTGTGGAAGG | SEQ ID NO: 30 |
| | reverse | ACACATTGGGGGTAGGAACA | SEQ ID NO: 31 |

TABLE 6

Characterization of human subjects.

| Characteristics | Healthy control | AAA & CAD | Aortic dissection |
|---|---|---|---|
| n (Male) | 12 (6) | 14 (14) | 10 (9) |
| Age, y | 37.8 ± 5.5 | 69.0 ± 15.7 | 66.8 ± 16.2 |

Baseline demographics for patients with aortic dissection

| | M/F | Age | |
|---|---|---|---|
| patient 1 | M | 73 | Stanford B |
| patient 2 | M | 87 | Stanford B |
| patient 3 | M | 50 | Stanford B |
| patient 4 | M | 66 | Stanford A |
| patient 5 | M | 41 | Stanford A |
| patient 6 | M | 45 | Stanford A |
| patient 7 | M | 63 | Stanford B |
| patient 8 | M | 87 | Stanford B |
| patient 9 | M | 84 | Stanford B |
| patient 10 | F | 72 | Stanford B |

AAA: abdominal aortic aneurysms,
CAD: coronary artery disease,
Data are expressed as number or mean ± standard deviation.

REFERENCES

1 Nienaber, C. A. & Powell, J. T. Management of acute aortic syndromes. Eur Heart J 33, 26-35b (2012).
2 Tsai, T. T., Nienaber, C. A. & Eagle, K. A. Acute aortic syndromes. Circulation 112, 3802-3813 (2005).
3 Hiratzka, L. F. et al. 2010 ACCF/AHA/AATS/ACR/ASA/SCA/SCAI/SIR/STS/SVM Guidelines for the diagnosis and management of patients with thoracic aortic disease. A Report of the American College of Cardiology Foundation/American Heart Association Task Force on Practice Guidelines, American Association for Thoracic Surgery, American College of Radiology, American Stroke Association, Society of Cardiovascular Anesthesiologists, Society for Cardiovascular Angiography and Interventions, Society of Interventional Radiology, Society of Thoracic Surgeons, and Society for Vascular Medicine. J Am Coll Cardiol 55, e27-e129 (2010).
4 Hagan, P. G. et al. The International Registry of Acute Aortic Dissection (IRAD): new insights into an old disease. JAMA 283, 897-903 (2000).
5 Suzuki, T. et al. Biomarkers of aortic diseases. Am Heart J 165, 15-25 (2013).
6 Suzuki, T., Distante, A. & Eagle, K. Biomarker-assisted diagnosis of acute aortic dissection: how far we have come and what to expect. Curr Opin Cardiol 25, 541-545 (2010).
7 Clough, R. E. & Nienaber, C. A. Management of acute aortic syndrome. Nature reviews. Cardiology doi:10.1038 (2014).
8 Song, J. K. Aortic intramural hematoma: aspects of pathogenesis 2011. Herz 36, 488-497 (2011).
9 von Kodolitsch, Y. et al. Intramural hematoma of the aorta: predictors of progression to dissection and rupture. Circulation 107, 1158-1163 (2003).
10 Milewicz, D. M., Regalado, E. S. & Guo, D. C. Treatment guidelines for thoracic aortic aneurysms and dissections based on the underlying causative gene. J Thorac Cardiovasc Surg 140, S2-4; discussion S45-51 (2010).
11 Milewicz, D. M. et al. Genetic basis of thoracic aortic aneurysms and dissections: focus on smooth muscle cell contractile dysfunction. Annu Rev Genomics Hum Genet 9, 283-302 (2008).
12 Holm, T. M. et al. Noncanonical TGFbeta signaling contributes to aortic aneurysm progression in Marfan syndrome mice. Science 332, 358-361 (2011).

13 Li, W. et al. Tgfbr2 disruption in postnatal smooth muscle impairs aortic wall homeostasis. *J Clin Invest* 124, 755-767 (2014).
14 Dietz, H. C. TGF-beta in the pathogenesis and prevention of disease: a matter of aneurysmic proportions. *J Clin Invest* 120, 403-407 (2010).
15 Ju, X. et al. Interleukin-6-signal transducer and activator of transcription-3 signaling mediates aortic dissections induced by angiotensin II via the T-helper lymphocyte 17-interleukin 17 axis in C57BL/6 mice. *Arterioscler Thromb Vasc Biol* 33, 1612-1621 (2013).
16 Tieu, B. C. et al. An adventitial IL-6/MCP1 amplification loop accelerates macrophage-mediated vascular inflammation leading to aortic dissection in mice. *J Clin Invest* 119, 3637-3651 (2009).
17 Date, D. et al. Kruppel-like transcription factor 6 regulates inflammatory macrophage polarization. *J Biol Chem* 289, 10318-10329 (2014).
18 Starkel, P. et al. Oxidative stress, KLF6 and transforming growth factor-beta up-regulation differentiate non-alcoholic steatohepatitis progressing to fibrosis from uncomplicated steatosis in rats. *J Hepatol* 39, 538-546 (2003).
19 Holian, J. et al. Role of Kruppel-like factor 6 in transforming growth factor-betas-induced epithelial-mesenchymal transition of proximal tubule cells. *Am J Physiol Renal Physiol* 295, F1388-1396 (2008).
20 Hamilton, J. A. & Anderson, G. P. GM-CSF Biology. *Growth Factors* 22, 225-231 (2004).
21 Daugherty, A., Manning, M. W. & Cassis, L. A. Angiotensin II promotes atherosclerotic lesions and aneurysms in apolipoprotein E-deficient mice. *J Clin Invest* 105, 1605-1612 (2000).
22 Johnston, K. W. et al. Suggested standards for reporting on arterial aneurysms. Subcommittee on Reporting Standards for Arterial Aneurysms, Ad Hoc Committee on Reporting Standards, Society for Vascular Surgery and North American Chapter, International Society for Cardiovascular Surgery. *J Vasc Surg* 13, 452-458 (1991).
23 Nagasawa, A. et al. Important role of the angiotensin II pathway in producing matrix metalloproteinase-9 in human thoracic aortic aneurysms. *J Surg Res* 183, 472-477 (2013).
24 Ezekowitz, R. A. & Gordon, S. Down-regulation of mannosyl receptor-mediated endocytosis and antigen F4/80 in bacillus Calmette-Guerin-activated mouse macrophages. Role of T lymphocytes and lymphokines. *J Exp Med* 155, 1623-1637 (1982).
25 Ezekowitz, R. A., Austyn, J., Stahl, P. D. & Gordon, S. Surface properties of bacillus Calmette-Guerin-activated mouse macrophages. Reduced expression of mannose-specific endocytosis, Fc receptors, and antigen F4/80 accompanies induction of Ia. *J Exp Med* 154, 60-76 (1981).
26 Atreya, R. et al. Blockade of interleukin 6 trans signaling suppresses T-cell resistance against apoptosis in chronic intestinal inflammation: evidence in crohn disease and experimental colitis in vivo. *Nat Med* 6, 583-588 (2000).
27 Cheuk, B. L. & Cheng, S. W. Can local secretion of prostaglandin E2, thromboxane B2, and interleukin-6 play a role in ruptured abdominal aortic aneurysm? *World J Surg* 32, 55-61 (2008).
28 Dawson, J. et al. Aortic aneurysms secrete interleukin-6 into the circulation. *J Vasc Surg* 45, 350-356 (2007).
29 Dawson, J., Cockerill, G., Choke, E., Loftus, I. & Thompson, M. M. Aortic aneurysms as a source of circulating interleukin-6. *Ann N Y Acad Sci* 1085, 320-323 (2006).
30 Treska, V., Topolcan, O. & Pecen, L. Cytokines as plasma markers of abdominal aortic aneurysm. *Clin Chem Lab Med* 38, 1161-1164 (2000).
31 Wright, H. L., Moots, R. J., Bucknall, R. C. & Edwards, S. W. Neutrophil function in inflammation and inflammatory diseases. *Rheumatology* 49, 1618-1631 (2010).
32 Habashi, J. P. et al. Angiotensin II type 2 receptor signaling attenuates aortic aneurysm in mice through ERK antagonism. *Science* 332, 361-365 (2011).
33 Lindsay, M. E. et al. Loss-of-function mutations in TGFB2 cause a syndromic presentation of thoracic aortic aneurysm. *Nat Genet* 44, 922-927 (2012).
34 Sawaki, D. & Suzuki, T. Targeting transforming growth factor-beta signaling in aortopathies in Marfan syndrome. *Circ J* 77, 898-899 (2013).
35 Feng, X. H. & Derynck, R. Specificity and versatility in tgf-beta signaling through Smads. *Annu Rev Cell Dev Biol* 21, 659-693 (2005).
36 Shindo, J. et al. Granulocyte-macrophage colony-stimulating factor prevents the progression of atherosclerosis via changes in the cellular and extracellular composition of atherosclerotic lesions in watanabe heritable hyperlipidemic rabbits. *Circulation* 99, 2150-2156 (1999).
37 Zhu, S. N., Chen, M., Jongstra-Bilen, J. & Cybulsky, M. I. GM-CSF regulates intimal cell proliferation in nascent atherosclerotic lesions. *J Exp Med* 206, 2141-2149 (2009).
38 Haghighat, A., Weiss, D., Whalin, M. K., Cowan, D. P. & Taylor, W. R. Granulocyte colony-stimulating factor and granulocyte macrophage colony-stimulating factor exacerbate atherosclerosis in apolipoprotein E-deficient mice. *Circulation* 115, 2049-2054 (2007).
39 Ye, P. et al. GM-CSF contributes to aortic aneurysms resulting from SMAD3 deficiency. *J Clin Invest* 123, 2317-2331 (2013).
40 Kimura, T. et al. Tenascin C protects aorta from acute dissection in mice. *Sci Rep* 4, 4051 (2014).
41 Weissen-Plenz, G. et al. Aortic dissection associated with Cogans's syndrome: deleterious loss of vascular structural integrity is associated with GM-CSF overstimulation in macrophages and smooth muscle cells. *J Cardiothorac Surg* 5, 66 (2010).
42 Kessel, A., Vadasz, Z. & Toubi, E. Cogan syndrome—Pathogenesis, clinical variants and treatment approaches. *Autoimmun Rev* 13, 351-354 (2014).
43 Babamusta, F. et al. Angiotensin II infusion induces site-specific intra-laminar hemorrhage in macrophage colony-stimulating factor-deficient mice. *Atherosclerosis* 186, 282-290 (2006).
44 Brocheriou, I. et al. Antagonistic regulation of macrophage phenotype by M-CSF and GM-CSF: implication in atherosclerosis. *Atherosclerosis* 214, 316-324 (2011).
45 Filonzi, E. L., Zoellner, H., Stanton, H. & Hamilton, J. A. Cytokine regulation of granulocyte-macrophage colony stimulating factor and macrophage colony-stimulating factor production in human arterial smooth muscle cells. *Atherosclerosis* 99, 241-252 (1993).
46 Sakai, M. et al. Glucocorticoid inhibits oxidized LDL-induced macrophage growth by suppressing the expression of granulocyte/macrophage colony-stimulating factor. *Arterioscler Thromb Vasc Biol* 19, 1726-1733 (1999).
47 Plenz, G., Koenig, C., Severs, N. J. & Robenek, H. Smooth muscle cells express granulocyte-macrophage colony-stimulating factor in the undiseased and atherosclerotic human coronary artery. *Arterioscler Thromb Vasc Biol* 17, 2489-2499 (1997).

48 Saraff, K., Babamusta, F., Cassis, L. A. & Daugherty, A. Aortic dissection precedes formation of aneurysms and atherosclerosis in angiotensin II-infused, apolipoprotein E-deficient mice. *Arterioscler Thromb Vasc Biol* 23, 1621-1626 (2003).

49 Cavalcante, J. L., Lima, J. A., Redheuil, A. & Al-Mallah, M. H. Aortic stiffness: current understanding and future directions. *J Am Coll Cardiol* 57, 1511-1522 (2011).

50 Tarocchi, M. et al. Carcinogen-induced hepatic tumors in KLF6+/− mice recapitulate aggressive human hepatocellular carcinoma associated with p53 pathway deregulation. *Hepatology* 54, 522-531 (2011).

51 Clausen, B. E., Burkhardt, C., Reith, W., Renkawitz, R. & Forster, I. Conditional gene targeting in macrophages and granulocytes using LysMcre mice. *Transgenic Res* 8, 265-277 (1999).

The invention claimed is:

1. A method of treating or ameliorating aortic intramural hematoma progression or recurrence in a subject in need of such treatment, the method comprising administering, to the subject, a therapeutically effective amount of a granulocyte macrophage colony-stimulating factor (GM-CSF) negative modulator.

2. A method according to claim 1, wherein the negative modulator comprises an anti-GM-CSF antibody or antigen-binding fragment thereof.

3. A method according to claim 2, wherein the anti-GM-CSF antibody or antigen-binding fragment thereof specifically binds to SEQ ID No:2, or a variant or fragment thereof.

4. A method according to claim 3, wherein the antibody is the antibody derived from hybridoma clone MP1-22E9 or the antibody designated as sc-377039, clone number A-6.

5. A method according to claim 2, wherein the antibody or antigen-binding fragment thereof comprises a monoclonal antibody or an antigen-binding fragment thereof, or wherein the antibody is a human or humanised antibody.

6. A method according to claim 2, wherein the antibody is the antibody designated as sc-377039, and is derived from hybridoma clone number A-6.

* * * * *

SEQUENCE LISTING

<160> NUMBER OF SEQ ID NOS: 31

<210> SEQ ID NO 1
<211> LENGTH: 2379
<212> TYPE: DNA
<213> ORGANISM: Homo sapiens

<400> SEQUENCE: 1

```
acacagagag aaaggctaaa gttctctgga ggatgtggct gcagagcctg ctgctcttgg      60
gcactgtggc ctgcagcatc tctgcacccg cccgctcgcc cagccccagc acgcagccct     120
gggagcatgt gaatgccatc caggaggccc ggcgtctcct gaacctgagt agagacactg     180
ctgctgagat ggtaagtgag agaatgtggg cctgtgccta ggccacccag ctggcccctg     240
actggccacg cctgtcagct tgataacatg acattttcct tttctacaga atgaaacagt     300
agaagtcatc tcagaaatgt ttgacctcca ggtaagatgc ttctctctga catagctttc     360
cagaagcccc tgccctgggg tggaggtggg gactccattt tagatggcac cacacagggg     420
tgtccacttt ctctccagtc agctggctgc aggaggaggg ggtagcaact gggtgctcaa     480
gaggctgctg gccgtgcccc tatggcagtc acatgagctc ctttatcagc tgagcggcca     540
tgggcagacc tagcattcaa tggccaggag tcaccagggg acaggtggta aagtgggggt     600
cacttcatga gacaggagct gtgggtttgg ggcgctcact gtgccccgag accaagtcct     660
gttgagacag tgctgactac agagaggcac agaggggttt caggaacaac ccttgcccac     720
ccagcaggtc caggtgaggc cccaccccc tctccctgaa tgatggggtg agagtcacct     780
ccttccctaa ggctgggctc ctctccaggt gccgctgagg gtggcctggg cggggcagtg     840
agaagggcag gttcgtgcct gccatggaca gggcagggtc tatgactgga cccagcctgt     900
gcccctccca agccctactc ctggggggctg ggggcagcag caaaaaggag tggtggagag     960
ttcttgtacc actgtgggca cttggccact gctcaccgac gaacgacatt ttccacagga    1020
gccgacctgc ctacagaccc gcctggagct gtacaagcag ggcctgcggg gcagcctcac    1080
caagctcaag ggcccccttga ccatgatggc cagccactac aagcagcact gccctccaac    1140
cccggtgagt gcctacggca gggcctccag caggaatgtc ttaatctagg gggtggggtc    1200
gacatgggga gagatctatg gctgtggctg ttcaggaccc caggggggttt ctgtgccaac    1260 agttatgtaa tgattagccc tccagagagg aggcagacag cccatttcat cccaaggagt    1320
cagagccaca gagcgctgaa gcccacagtg ctccccagca ggagctgctc ctatcctggt    1380
cattattgtc attatggtta atgaggtcag aggtgagggc aaacccaagg aaacttgggg    1440
cctgcccaag gcccagagga agtgcccagg cccaagtgcc accttctggc aggactttcc    1500
tctggcccca catgggtgc ttgaattgca gaggatcaag gaagggaggc tacttggaat    1560
ggacaaggac ctcaggcact ccttcctgcg ggaagggagc aaagtttgtg gccttgactc    1620
cactccttct gggtgcccag agacgacctc agcccagctg ccctgctctg ccctgggacc    1680
aaaaaggcag gcgtttgact gcccagaagg ccaacctcag gctggcactt aagtcaggcc    1740
```

```
cttgactctg gctgccactg gcagagctat gcactccttg gggaacacgt gggtggcagc    1800
agcgtcacct gacccaggtc agtgggtgtg tcctggagtg ggcctcctgg cctctgagtt    1860
ctaagaggca gtagagaaac atgctggtgc ttccttcccc cacgttaccc acttgcctgg    1920
actcaagtgt ttttattttt cttttttta aaggaaactt cctgtgcaac ccagattatc    1980
acctttgaaa gtttcaaaga gaacctgaag gactttctgc ttgtcatccc ctttgactgc    2040
tgggagccag tccaggagtg agaccggcca gatgaggctg gccaagccgg ggagctgctc    2100
tctcatgaaa caagagctag aaactcagga tggtcatctt ggagggacca aggggtgggc    2160
cacagccatg gtgggagtgg cctggacctg ccctgggcca cactgaccct gatacaggca    2220
tggcagaaga atgggaatat tttatactga cagaaatcag taatatttat atatttatat    2280
ttttaaaata tttatttatt tatttattta agttcatatt ccatatttat tcaagatgtt    2340
ttaccgtaat aattattatt aaaaatatgc ttctacttg                           2379
```

<210> SEQ ID NO 2
<211> LENGTH: 144
<212> TYPE: PRT
<213> ORGANISM: Homo sapiens

<400> SEQUENCE: 2

```
Met Trp Leu Gln Ser Leu Leu Leu Gly Thr Val Ala Cys Ser Ile
1               5                   10                  15

Ser Ala Pro Ala Arg Ser Pro Ser Thr Gln Pro Trp Glu His
            20                  25                  30

Val Asn Ala Ile Gln Glu Ala Arg Arg Leu Leu Asn Leu Ser Arg Asp
            35                  40                  45

Thr Ala Ala Glu Met Asn Glu Thr Val Glu Val Ile Ser Glu Met Phe
    50                  55                  60

Asp Leu Gln Glu Pro Thr Cys Leu Gln Thr Arg Leu Glu Leu Tyr Lys
65                  70                  75                  80

Gln Gly Leu Arg Gly Ser Leu Thr Lys Leu Lys Gly Pro Leu Thr Met
                85                  90                  95

Met Ala Ser His Tyr Lys Gln His Cys Pro Pro Thr Pro Glu Thr Ser
            100                 105                 110

Cys Ala Thr Gln Ile Ile Thr Phe Glu Ser Phe Lys Glu Asn Leu Lys
        115                 120                 125

Asp Phe Leu Leu Val Ile Pro Phe Asp Cys Trp Glu Pro Val Gln Glu
    130                 135                 140
```

<210> SEQ ID NO 3
<211> LENGTH: 30
<212> TYPE: PRT
<213> ORGANISM: Homo sapiens

<400> SEQUENCE: 3

```
Thr Gln Ile Ile Thr Phe Glu Ser Phe Lys Glu Asn Leu Lys Asp Phe
1               5                   10                  15

Leu Leu Val Ile Pro Phe Asp Cys Trp Glu Pro Val Gln Glu
            20                  25                  30
```

<210> SEQ ID NO 4
<211> LENGTH: 20
<212> TYPE: DNA
<213> ORGANISM: Artificial Sequence
<220> FEATURE:
<223> OTHER INFORMATION: Primer Sequence

<400> SEQUENCE: 4
aagcccttcc aagaactggc                                                    20

<210> SEQ ID NO 5
<211> LENGTH: 20
<212> TYPE: DNA
<213> ORGANISM: Artificial Sequence
<220> FEATURE:
<223> OTHER INFORMATION: Primer Sequence

<400> SEQUENCE: 5
ggcccctcaa aaggagagg                                                     20

<210> SEQ ID NO 6
<211> LENGTH: 20
<212> TYPE: DNA
<213> ORGANISM: Artificial Sequence
<220> FEATURE:
<223> OTHER INFORMATION: Primer Sequence

<400> SEQUENCE: 6
agttgccttc ttgggactga                                                    20

<210> SEQ ID NO 7
<211> LENGTH: 20
<212> TYPE: DNA
<213> ORGANISM: Artificial Sequence
<220> FEATURE:
<223> OTHER INFORMATION: Primer Sequence

<400> SEQUENCE: 7
tccacgattt cccagagaac                                                    20

<210> SEQ ID NO 8
<211> LENGTH: 20
<212> TYPE: DNA
<213> ORGANISM: Artificial Sequence
<220> FEATURE:
<223> OTHER INFORMATION: Primer Sequence

<400> SEQUENCE: 8
ttggccaaga ttctcttcct                                                    20

<210> SEQ ID NO 9
<211> LENGTH: 20
<212> TYPE: DNA
<213> ORGANISM: Artificial Sequence
<220> FEATURE:
<223> OTHER INFORMATION: Primer Sequence

<400> SEQUENCE: 9
tcactgcctc cactagcatc                                                    20

<210> SEQ ID NO 10
<211> LENGTH: 25
<212> TYPE: DNA
<213> ORGANISM: Artificial Sequence
<220> FEATURE:
<223> OTHER INFORMATION: Primer Sequence

<400> SEQUENCE: 10
atctcttcta gagactggga aggag                                              25

<210> SEQ ID NO 11
<211> LENGTH: 25

```
<212> TYPE: DNA
<213> ORGANISM: Artificial Sequence
<220> FEATURE:
<223> OTHER INFORMATION: Primer Sequence

<400> SEQUENCE: 11
aataaaaggt cagaatccac cctac                                         25

<210> SEQ ID NO 12
<211> LENGTH: 20
<212> TYPE: DNA
<213> ORGANISM: Artificial Sequence
<220> FEATURE:
<223> OTHER INFORMATION: Primer Sequence

<400> SEQUENCE: 12
agagagctgc agcaaaaagg                                               20

<210> SEQ ID NO 13
<211> LENGTH: 20
<212> TYPE: DNA
<213> ORGANISM: Artificial Sequence
<220> FEATURE:
<223> OTHER INFORMATION: Primer Sequence

<400> SEQUENCE: 13
ggaaagaggc agttgcaaag                                               20

<210> SEQ ID NO 14
<211> LENGTH: 25
<212> TYPE: DNA
<213> ORGANISM: Artificial Sequence
<220> FEATURE:
<223> OTHER INFORMATION: Primer Sequence

<400> SEQUENCE: 14
catcttctca aaattcgagt gacaa                                         25

<210> SEQ ID NO 15
<211> LENGTH: 23
<212> TYPE: DNA
<213> ORGANISM: Artificial Sequence
<220> FEATURE:
<223> OTHER INFORMATION: Primer Sequence

<400> SEQUENCE: 15
tgggagtaga caaggtacaa ccc                                           23

<210> SEQ ID NO 16
<211> LENGTH: 25
<212> TYPE: DNA
<213> ORGANISM: Artificial Sequence
<220> FEATURE:
<223> OTHER INFORMATION: Primer Sequence

<400> SEQUENCE: 16
caaccaacaa gtgatattct ccatg                                         25

<210> SEQ ID NO 17
<211> LENGTH: 21
<212> TYPE: DNA
<213> ORGANISM: Artificial Sequence
<220> FEATURE:
<223> OTHER INFORMATION: Primer Sequence

<400> SEQUENCE: 17
```
gatccacact ctccagctgc a            21

<210> SEQ ID NO 18
<211> LENGTH: 20
<212> TYPE: DNA
<213> ORGANISM: Artificial Sequence
<220> FEATURE:
<223> OTHER INFORMATION: Primer Sequence

<400> SEQUENCE: 18
accttgttca gctacgcctt            20

<210> SEQ ID NO 19
<211> LENGTH: 20
<212> TYPE: DNA
<213> ORGANISM: Artificial Sequence
<220> FEATURE:
<223> OTHER INFORMATION: Primer Sequence

<400> SEQUENCE: 19
cattcccaaa tgtgcttgtc            20

<210> SEQ ID NO 20
<211> LENGTH: 20
<212> TYPE: DNA
<213> ORGANISM: Artificial Sequence
<220> FEATURE:
<223> OTHER INFORMATION: Primer Sequence

<400> SEQUENCE: 20
ggctggagag ctacaagagg            20

<210> SEQ ID NO 21
<211> LENGTH: 20
<212> TYPE: DNA
<213> ORGANISM: Artificial Sequence
<220> FEATURE:
<223> OTHER INFORMATION: Primer Sequence

<400> SEQUENCE: 21
atgtctggac ccattccttc            20

<210> SEQ ID NO 22
<211> LENGTH: 20
<212> TYPE: DNA
<213> ORGANISM: Artificial Sequence
<220> FEATURE:
<223> OTHER INFORMATION: Primer Sequence

<400> SEQUENCE: 22
ggccttggaa gcatgtagag            20

<210> SEQ ID NO 23
<211> LENGTH: 20
<212> TYPE: DNA
<213> ORGANISM: Artificial Sequence
<220> FEATURE:
<223> OTHER INFORMATION: Primer Sequence

<400> SEQUENCE: 23
gggggcagta tgtctggtag            20

<210> SEQ ID NO 24
<211> LENGTH: 20
<212> TYPE: DNA
<213> ORGANISM: Artificial Sequence
<220> FEATURE:
<223> OTHER INFORMATION: Primer Sequence

<400> SEQUENCE: 24
caccgcgtcc tgtaactctt         20

<210> SEQ ID NO 25
<211> LENGTH: 20
<212> TYPE: DNA
<213> ORGANISM: Artificial Sequence
<220> FEATURE:
<223> OTHER INFORMATION: Primer Sequence

<400> SEQUENCE: 25
gcaccttgac cttgtgacct         20

<210> SEQ ID NO 26
<211> LENGTH: 19
<212> TYPE: DNA
<213> ORGANISM: Artificial Sequence
<220> FEATURE:
<223> OTHER INFORMATION: Primer Sequence

<400> SEQUENCE: 26
tggcgttacc ttggtaacc          19

<210> SEQ ID NO 27
<211> LENGTH: 19
<212> TYPE: DNA
<213> ORGANISM: Artificial Sequence
<220> FEATURE:
<223> OTHER INFORMATION: Primer Sequence

<400> SEQUENCE: 27
ggtgttgagc cctttccag          19

<210> SEQ ID NO 28
<211> LENGTH: 20
<212> TYPE: DNA
<213> ORGANISM: Artificial Sequence
<220> FEATURE:
<223> OTHER INFORMATION: Primer Sequence

<400> SEQUENCE: 28
catcttcgtc cgtccctgtg         20

<210> SEQ ID NO 29
<211> LENGTH: 24
<212> TYPE: DNA
<213> ORGANISM: Artificial Sequence
<220> FEATURE:
<223> OTHER INFORMATION: Primer Sequence

<400> SEQUENCE: 29
ctgctatcac ttcctttctg ttgc    24

<210> SEQ ID NO 30
<211> LENGTH: 20
<212> TYPE: DNA
<213> ORGANISM: Artificial Sequence
<220> FEATURE:
<223> OTHER INFORMATION: Primer Sequence

<400> SEQUENCE: 30
aactttggca ttgtggaagg         20

```
<210> SEQ ID NO 31
<211> LENGTH: 20
<212> TYPE: DNA
<213> ORGANISM: Artificial Sequence
<220> FEATURE:
<223> OTHER INFORMATION: Primer Sequence

<400> SEQUENCE: 31
acacattggg ggtaggaaca                                              20
```